US008338484B2

(12) United States Patent
Hutchinson et al.

(10) Patent No.: US 8,338,484 B2
(45) Date of Patent: Dec. 25, 2012

(54) N,N-DISUBSTITUTED AMINOALKYLBIPHENYL ANTAGONISTS OF PROSTAGLANDIN D2 RECEPTORS

(75) Inventors: John Howard Hutchinson, La Jolla, CA (US); Brian Andrew Stearns, San Diego, CA (US); Yen Pham Truong, San Diego, CA (US)

(73) Assignee: Panmira Pharmaceuticals, LLC, San Diego, CA (US)

( * ) Notice: Subject to any disclaimer, the term of this patent is extended or adjusted under 35 U.S.C. 154(b) by 0 days.

(21) Appl. No.: 13/297,160

(22) Filed: Nov. 15, 2011

(65) Prior Publication Data

US 2012/0059055 A1     Mar. 8, 2012

Related U.S. Application Data

(63) Continuation of application No. 12/362,439, filed on Jan. 29, 2009, now Pat. No. 8,168,678.

(60) Provisional application No. 61/110,496, filed on Oct. 31, 2008, provisional application No. 61/025,597, filed on Feb. 1, 2008.

(51) Int. Cl.
A01N 37/12 (2006.01)
(52) U.S. Cl. ........ 514/564; 514/858; 514/859; 514/860; 514/861; 514/914
(58) Field of Classification Search .................. 514/564, 514/858–861, 914
See application file for complete search history.

(56) References Cited

U.S. PATENT DOCUMENTS

| | | | |
|---|---|---|---|
| 5,239,084 A | 8/1993 | Guerry et al. |
| 5,334,598 A | 8/1994 | Bagley et al. |
| 5,668,176 A | 9/1997 | Bagley et al. |
| 5,827,868 A | 10/1998 | Misra et al. |
| 6,617,351 B1 | 9/2003 | Arnold et al. |
| 6,884,593 B1 | 4/2005 | Hirai et al. |
| 7,005,440 B1 | 2/2006 | Jayyosi et al. |
| 7,144,913 B2 | 12/2006 | Wang et al. |
| 7,205,329 B2 | 4/2007 | Chien et al. |
| 8,067,445 B2 | 11/2011 | Hutchinson et al. |
| 8,168,678 B2 | 5/2012 | Hutchinson et al. |
| 2001/0047027 A1 | 11/2001 | Labelle et al. |
| 2002/0198251 A1 | 12/2002 | Sundermann et al. |
| 2004/0214888 A1 | 10/2004 | Matsura et al. |
| 2004/0220237 A1 | 11/2004 | Fu et al. |
| 2005/0154044 A1 | 7/2005 | Beaulieu et al. |
| 2005/0171143 A1 | 8/2005 | Tanimoto et al. |
| 2005/0272756 A1 | 12/2005 | Leblanc et al. |
| 2006/0040999 A1 | 2/2006 | Ali et al. |
| 2006/0100425 A1 | 5/2006 | Bennani et al. |
| 2006/0106081 A1 | 5/2006 | Bennani et al. |
| 2007/0155726 A1 | 7/2007 | Arnaiz et al. |
| 2008/0167378 A1 | 7/2008 | Fukatsu et al. |
| 2008/0306109 A1 | 12/2008 | Hynd et al. |
| 2009/0186923 A1 | 7/2009 | Armer et al. |
| 2010/0004331 A1 | 1/2010 | Hutchinson et al. |
| 2010/0081673 A1 | 4/2010 | Hutchinson et al. |
| 2010/0113503 A1 | 5/2010 | Hutchinson et al. |
| 2010/0173313 A1 | 7/2010 | Bain et al. |
| 2010/0280049 A1 | 11/2010 | Stearns et al. |
| 2010/0298368 A1 | 11/2010 | Stearns et al. |
| 2011/0021573 A1 | 1/2011 | Hutchinson et al. |
| 2011/0034558 A1 | 2/2011 | Brittain et al. |
| 2011/0098352 A1 | 4/2011 | Hutchinson et al. |
| 2011/0245303 A1 | 10/2011 | Hutchinson et al. |
| 2012/0058123 A1 | 3/2012 | Hutchinson et al. |

FOREIGN PATENT DOCUMENTS

| | | |
|---|---|---|
| EP | 1170594 A2 | 1/2002 |
| GB | 2460597 B | 4/2010 |
| GB | 2461629 B | 5/2010 |
| GB | 2463788 B | 12/2010 |
| JP | 2004-182657 A | 7/2004 |
| WO | WO-95-03044 | 2/1995 |
| WO | WO-99-11605 A1 | 3/1999 |
| WO | WO-03-006011 A1 | 1/2003 |
| WO | WO-2004-035543 A1 | 4/2004 |
| WO | WO-2004-058164 A2 | 7/2004 |
| WO | WO-2004-094372 | 11/2004 |
| WO | WO-2004-096777 A1 | 11/2004 |
| WO | WO-2005-040114 A1 | 5/2005 |
| WO | WO-2005-044260 A1 | 5/2005 |
| WO | WO-2005-051373 A1 | 6/2005 |
| WO | WO-2005-100298 A1 | 10/2005 |
| WO | WO-2005-105727 A1 | 10/2005 |
| WO | WO-2006-002099 | 1/2006 |
| WO | WO-2006-005909 A1 | 1/2006 |
| WO | WO-2006-014357 A1 | 2/2006 |
| WO | WO-2006-018325 A1 | 2/2006 |
| WO | WO-2006-037982 A2 | 4/2006 |
| WO | WO-2006-052798 A2 | 5/2006 |
| WO | WO-2006-056854 A1 | 6/2006 |
| WO | WO-2006-070325 A2 | 7/2006 |
| WO | WO-2006-125596 A1 | 11/2006 |

(Continued)

OTHER PUBLICATIONS

Arima, M., and Fukuda, T., "Prostaglandin $D_2$ receptors DP and CRTH2 in the pathogenesis of asthma," Curr. Mol. Med. 8, 365-375 (2008).

(Continued)

Primary Examiner — Jafar Parsa
(74) Attorney, Agent, or Firm — Wilson, Sonsini, Goodrich & Rosati

(57) ABSTRACT

Described herein are compounds that are antagonists of $PGD_2$ receptors. Also described are pharmaceutical compositions that include the compounds described herein, and methods of using such antagonists of $PGD_2$ receptors, alone or in combination with other compounds, for treating respiratory, cardiovascular, and other $PGD_2$-dependent or $PGD_2$-mediated conditions or diseases.

10 Claims, 7 Drawing Sheets

FOREIGN PATENT DOCUMENTS

| | | |
|---|---|---|
| WO | WO-2007-037187 A1 | 4/2007 |
| WO | WO-2007-039736 A1 | 4/2007 |
| WO | WO-2007-041494 | 4/2007 |
| WO | WO-2007-047378 | 4/2007 |
| WO | WO-2007-068894 A2 | 6/2007 |
| WO | WO-2007-088996 A1 | 8/2007 |
| WO | WO-2007-107772 A1 | 9/2007 |
| WO | WO-2007-144127 A1 | 12/2007 |
| WO | WO-2008-017989 A1 | 2/2008 |
| WO | WO-2008-024746 A1 | 2/2008 |
| WO | WO-2008-082567 A1 | 7/2008 |
| WO | WO-2008-137027 A2 | 11/2008 |
| WO | WO-2008-156780 A1 | 12/2008 |
| WO | WO-2009-004379 A1 | 1/2009 |
| WO | WO-2009-044147 A1 | 4/2009 |
| WO | WO-2009-063202 | 5/2009 |
| WO | WO-2009-063215 | 5/2009 |
| WO | WO-2009-089192 A1 | 7/2009 |
| WO | WO-2009-099901 A1 | 8/2009 |
| WO | WO-2009-099902 A1 | 8/2009 |
| WO | WO-2009-102893 A2 | 8/2009 |
| WO | WO-2009-108720 A2 | 9/2009 |
| WO | WO-2009-145989 A2 | 12/2009 |
| WO | WO-2010-003120 A2 | 1/2010 |
| WO | WO-2010-037054 A2 | 4/2010 |
| WO | WO-2010-037059 A2 | 4/2010 |
| WO | WO-2010-039977 A2 | 4/2010 |
| WO | WO-2010-042652 A2 | 4/2010 |
| WO | WO-2010-057118 A2 | 5/2010 |
| WO | WO-2011-014587 A2 | 2/2011 |
| WO | WO-2011-014588 A2 | 2/2011 |
| WO | WO-2011-017201 A2 | 2/2011 |

OTHER PUBLICATIONS

Brannan et al., "Inhibition of Mast Cell PGD2 Release Protects Against Mannitol-Induced Airway Narrowing," Eur Respir J, 2006, vol. 27, No. 5, pp. 944-950, ERS Journals Ltd.

Cossette et al., "Agonist and Antagonist Effects of 15R-Prostaglandin (PG) $D_2$ and 11-Methylene-$PGD_2$ on Human Eosinophils and Basophils," Journal of Pharmacology and Experimental Therapeutics, 2007, pp. 173-179, vol. 320, No. 1, American Society for Pharmacology and Experimental Therapeutics, USA.

Crosignani et al., "Discovery of a new class of potent, selective, and orally bioavailable CRTH2(DP2) receptor antagonists for the treatment of allergic inflammatory diseases" J Med Chem 51:2227-2243 (2008).

EP09709954.3 Search Report mailed Feb. 21, 2011.

Evans et al., "Seeing the future of bioactive lipid drug targets," Nature Chem Biol 6:476-479 (2010).

Golub et al., "Molecular Classification of Cancer: Class Discovery and Class Prediction by Gene Expression Monitoring," Science (1999), vol. 286, 531-537.

Hata, A.N. and Breyer, R.M., "Pharmacology and signaling of prostaglandin receptors: multiple roles in inflammation and immune modulation," Pharmacol Ther. Aug;103(2):147-66 (2004).

Jatakanon et al., "Neutrophilic Inflammation in Severe Persistent Asthma," Am J Respir Crit Care Med 1999, pp. 1532-1539, vol. 160, National Heart and Lung Institute, London, UK.

Johnston et al., "Prostaglandin $D_2$-Induced Bronchoconstriction Is Mediated Only in Part by the Thromboxane Prostanoid Receptor," Eur Respir J, 1995, 8, pp. 411-415, ERS Journals Ltd, UK.

Kim et al., "Regulation of Immune Cells by Eicosanoid Receptors," TheScientificWorld Journal 7:1307-1328 (2007).

Kostenis, E. and Ulven, T., "Emerging roles of DP and CRTH2 in allergic inflammation," Trends Mol Med. Apr;12(4):148-58 (2008).

Lala et al., "Role of Nitric Oxide in Tumor Progression: Lessons from Experimental Tumors," Cancer and Metastasis Reviews (1998), 17, 91-106.

Ly and Bacon, "Small-molecule CRTH2 antagonists for the treatment of allergic inflammation: an overview," Exp Opin Invest Drugs 14:769 (2005).

Medina, J. C. and Liu, J., "PGD2 Antagonists" Annual Reports in Medicinal Chemistry, vol. 41, 2006, pp. 221-235.

PCT/US09/32495 IPRP dated Aug. 3, 2010.
PCT/US09/32495 Written Opinion and Search Report dated Jun. 29, 2009.
PCT/US09/32499 IPRP dated Aug. 3, 2010.
PCT/US09/32499 Written Opinion and Search Report dated Jun. 29, 2009.
PCT/US09/33961 IPER and Written Opinion mailed Aug. 26, 2010.
PCT/US09/33961 Search Report mailed Aug. 11, 2009.
PCT/US09/35174 IPER and Written Opinion mailed Sep. 10, 2010.
PCT/US09/38291 Search Report and Written Opinion mailed Nov. 27, 2009.
PCT/US09/49621 Search Report and Written Opinion mailed Mar. 15, 2010.
PCT/US09/49631 Search Report and Written Opinion mailed Feb. 24, 2010.
PCT/US09/58655 Search Report and Written Opinion mailed May 10, 2010.
PCT/US09/58663 Search Report and Written Opinion mailed May 14, 2010.
PCT/US09/59256 Search Report and Written Opinion mailed Jun. 21, 2010.
PCT/US09/59891 Search Report and Written Opinion mailed May 24, 2010.
PCT/US09/64630 Search Report and Written Opinion mailed Jul. 19, 2010.
PCT/US10/43598 Search Report and Written Opinion mailed Apr. 22, 2011.
PCT/US10/43599 Search Report and Written Opinion mailed Apr. 28, 2011.
PCT/US10/43783 Search Report and Written Opinion mailed Apr. 22, 2011.

Pettipher et al., "Antagonists of the prostaglandin D2 receptor CRTH2," Drug News Perspect 21:317-322 (2008).

Pettipher et al., "The roles of the prostaglandin D(2) receptors DP(1) and CRTH2 in promoting allergic responses," Br J Pharmacol 153:S191 (2008).

Pettipher, R. et al., "Antagonism of the prostaglandin D2 receptors DP1 and CRTH2 as an approach to treat allergic diseases," Nature Drug Discovery 6:313-325 (2007).

Prieto et al., "Racemization in Suzuki couplings: a quantitative study using 4-hydroxyphenylglycine and tyrosine derivatives as probe molecules," J Org Chem 72(3):1047-1049 (2007).

Sagel et al., "Sputum Biomarkers of Inflammation in Cystic Fibrosis Lung Disease," Proc Am Thorac Soc, 2007, vol. 4, pp. 406-417, www.atsjournals.org.

Sandham et al., "7-Azaindole-3-acetic acid derivatives: potent and selective CRTH2 receptor antagonists," Bioorg Med Chem Lett 19:4794-4798 (2009).

Sandig et al., "Contrary prostaglandins: the opposing roles of PGD2 and its metabolites in leukocyte function," J Leukocyte Biology 81:372-382 (2007).

Science IP Structure Search dated Nov. 6, 2007 (2 parts).

Scott et al., "Discovery and optimization of a biphenylacetic acid series of prostaglandin D2 receptor DP2 antagonists with efficacy in a murine model of allergic rhinitis," Bioorg Med Chem Ltrs (2011), doi: 10.1016fj.bmc1.2011.01.024.

Shrader et al., "Factor VIIa inhibitors: Gaining selectivity within the trypsin family," Bioorg Med Chem Ltrs 16(6):1596-1600 (2006).

Srinivas et al., "Biaryl amino acid templates in place of D-Pro-L-Pro in cyclic beta-hairpin cationic antimicrobial peptidomimetics," Organic & Biomolecular Chemistry 5(19):3100-3105 (2007).

Stearns et al., "Novel tricyclic antagonists of the prostaglandin D2 receptor DP2 with efficacy in a murine model of allergic rhinitis," Bioorg Med Chem Ltrs 19:4647-4651 (2009).

Stebbins et al., "DP2 Receptor Antagonists: Novel Therapeutic Target for COPD," Mol Cell Pharmacol 2(3):89-96 (2010).

Stebbins et al., "Pharmacological Blockade of the DP2 Receptor Inhibits Cigarette Smoke-Induced Inflammation, Mucus Cell Metaplasia, and Epithelial Hyperplasia in the Mouse Lung," J Pharmacol Exp Ther 332(3):764-775 (2010).

Stebbins et al., "Therapeutic efficacy of AM156, a novel prostanoid DP2 receptor antagonist, in murine models of allergic rhinitis and house dust mite-induced pulmonary inflammation," Eur J Pharmacol 638:142-149 (2010).

Stock et al., "Sodium [2'-[(cyclopropanecarbonyl-ethyl-amino)-methyl]-4'-(6-ethoxy-pyridin-3-yl)-6-methoxy-biphenyl-3-yl]acetate (AM432): A potent, selective prostaglandin D2 receptor antagonist," Bioorg Med Chem Ltrs 21:1036-1040 (2011).

Sugimoto et al., "An Orally Bioavailable Small Molecule Antagonist of CRTH2, Ramatroban (BAY u3405), Inhibits Prostaglandin $D_2$-Induced Eosinophil Migration in Vitro," Journal of Pharmacology and Experimental Therapeutics, 2003, pp. 347-352, vol. 305, No. 1, American Society for Pharmacology and Experimental Therapeutics, USA.

Takeshita et al., "CRTH2 is a prominent effector in contact hypersensitivity-induced neutrophil inflammation," Intl Immunol 16(7):947-959 (2004).

Tirouvanziam, R., et al., "Profound functional and signaling changes in viable inflammatory neutrophils homing to cystic fibrosis airways," *Proc. Nat. Acad. Sci. USA* 105:4335-4339 (2008).

Ulven et al., "Minor Structural Modifications Cover the Dual TP/CRTH2," J Med Chem 48(4):897-900 (2005).

Ulven T et al,. "Targeting the prostaglandin D2 receptors DP and CRTH2 for treatment of inflammation", *Curr. Top. Med. Chem.* 2006;6(13):1427-44.

Wardlaw et al., "New Insights into the Relationship Between Airway Inflammation and Asthma," Clinical Science, 2002, pp. 201-211, vol. 103, The Biochemical Society and the Medical Research Society, GB.

Torisu et al. "Discovery of new chemical leads for prostaglandin $D_2$ receptor antagonists." *Bioorganic & Medicinal Chemistry Letters*, 2004, 14:4557-4562.

N,N-DISUBSTITUTED AMINOALKYLBIPHENYL ANTAGONISTS OF PROSTAGLANDIN D2 RECEPTORS

RELATED APPLICATIONS

This application is a continuation of U.S. application Ser. No. 12/362,439 entitled "N,N-disubstituted aminoalkylbiphenyl antagonists of prostaglandin D2 receptors" filed on Jan. 29, 2009, which claims the benefit of U.S. provisional patent application No. 61/025,597 entitled "N,N-disubstituted aminoalkylbiphenyl antagonists of prostaglandin D2 receptors" filed on Feb. 1, 2008 and U.S provisional patent application No. 61/110,496 entitled "N,N-disubstituted aminoalkylbiphenyl antagonists of prostaglandin D2 receptors" filed on Oct. 31, 2008, all of which are incorporated by reference in their entirety.

FIELD OF THE INVENTION

Described herein are compounds, methods of making such compounds, pharmaceutical compositions comprising such compounds, and methods of using such compounds to treat, prevent or diagnose diseases or conditions associated with prostaglandin $D_2$.

BACKGROUND OF THE INVENTION

Prostaglandins have a diverse range of activities and have a well recognized role in pain and inflammation. Prostaglandin $D_2$ ($PGD_2$) is produced by mast cells, macrophages and $T_H2$ lymphocytes in response to local tissue damage as well as allergic inflammation in diseases such as asthma, rhinitis, and atopic dermatitis. $PGD_2$ binds to a number of receptors, which include the thromboxane-type prostanoid (TP) receptor, $PGD_2$ receptor (DP, also known as $DP_1$) and chemoattractant receptor-homologous molecule expressed on Th2 cells (CRTH2; also known as $DP_2$).

SUMMARY OF THE INVENTION

Presented herein are compounds, pharmaceutical compositions, and methods, for (a) diagnosing, preventing, or treating allergic and non-allergic inflammation, (b) mitigating adverse signs and symptoms that are associated with inflammation, and/or (c) controlling immunological, proliferative disorders. These disorders may arise from one or more of a genetic, iatrogenic, immunological, infectious, oncological, toxic, surgical, and/or traumatic etiology. In one aspect, the methods, compounds, pharmaceutical compositions, and medicaments described herein comprise antagonists of $PGD_2$ receptors. In one aspect, the methods, compounds, pharmaceutical compositions, described herein comprise antagonists of $DP_2$.

In one aspect provided herein are compounds of Formula (I), pharmaceutically acceptable salts, pharmaceutically acceptable prodrugs, and pharmaceutically acceptable solvates thereof, which are antagonists of $DP_2$, and are used to treat mammals suffering from one or more $PGD_2$-dependent conditions or diseases, including, but not limited to, asthma, rhinitis, allergic conjuctivitis, atopic dermatitis, chronic obstructive pulmonary disease (COPD), pulmonary hypertension, interstitial lung fibrosis, arthritis, allergy, psoriasis, inflammatory bowel disease, adult respiratory distress syndrome, myocardial infarction, aneurysm, stroke, cancer, wound healing, endotoxic shock, pain, inflammatory conditions, eosinophilic esophagitis, eosinophil-associated gastrointestinal disorders (EGID), idiopathic hypereosinophilic syndrome, otitis, airway constriction, mucus secretion, nasal congestion, increased microvascular permeability and recruitment of eosinophils, urticaria, sinusitis, angioedema, anaphylaxia, chronic cough and Churg Strauss syndrome.

In one aspect, provided is a compound having the structure of Formula (I) or pharmaceutically acceptable salt thereof:

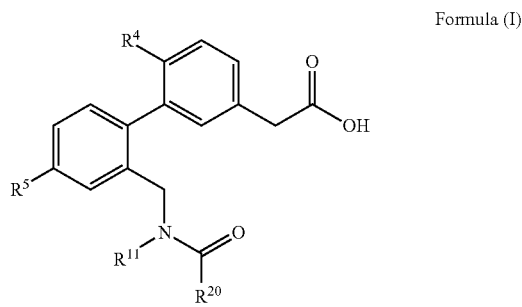

Formula (I)

wherein, $R^4$ is H, halogen, —CN, —OH, $C_1$-$C_4$alkyl, $C_1$-$C_4$alkoxy, $C_1$-$C_4$fluoroalkyl, $C_1$-$C_4$fluoroalkoxy, or $C_1$-$C_4$heteroalkyl;

$R^5$ is H, halogen, —CN, —NO$_2$, —OH, —S(=O)$_2$R$^{12}$, —NHS(=O)$_2$R$^{12}$, —C(=O)R$^{12}$, —OC(=O)R$^{12}$, —CO$_2$R$^{13}$, —N(R$^{13}$)$_2$, —C(=O)N(R$^{13}$)$_2$, —NHC(=O)R$^{12}$, —C(OH)(R$^{13}$)$_2$, $C_1$-$C_4$alkyl, $C_1$-$C_4$fluoroalkyl, $C_1$-$C_4$fluoroalkoxy, $C_1$-$C_4$alkoxy, $C_1$-$C_4$heteroalkyl, or —S—R$^{12}$;

$R^{20}$ is $C_1$-$C_4$alkyl, $C_3$-$C_6$cycloalkyl, —CH$_2$O—C$_1$-C$_4$alkyl, —CH$_2$O-(substituted or unsubstituted phenyl), —CH(CH$_3$)—O-(substituted or unsubstituted phenyl), —C(CH$_3$)$_2$—O-(substituted or unsubstituted phenyl), —CH$_2$OCH$_2$-(substituted or unsubstituted phenyl), —OC$_1$-C$_4$alkyl, —O—CH$_2$-(substituted or unsubstituted phenyl), —O—CH(CH$_3$)-(substituted or unsubstituted phenyl), —NR$^{16}$C$_1$-C$_4$alkyl, —NR$^{16}$—CH$_2$-(substituted or unsubstituted phenyl), or —NR$^{16}$—CH(CH$_3$)-(substituted or unsubstituted phenyl), wherein if the phenyl of R$^{20}$ is substituted, then the phenyl is substituted with 0, 1, or 2 R$^{21}$ groups;

each R$^{21}$ is independently selected from halogen, —OH, —OCH$_3$, $C_1$-$C_4$alkyl, and —CF$_3$;

R$^{16}$ is H or $C_1$-$C_4$alkyl;

R$^{11}$ is —CH$_3$, —CH$_2$CH$_3$, —CF$_3$, —CH$_2$CF$_3$, cyclopropyl, cyclobutyl, or cyclopentyl R$^{12}$ is $C_1$-$C_4$alkyl, $C_1$-$C_4$heteroalkyl, or $C_1$-$C_4$fluoroalkyl;

each R$^{13}$ is independently selected from H, $C_1$-$C_4$alkyl, $C_1$-$C_4$heteroalkyl, and $C_1$-$C_4$fluoroalkyl.

In one aspect, presented herein are the compounds of Formula (I) presented in Table 1, or pharmaceutically acceptable salts, pharmaceutically active metabolites, pharmaceutically acceptable prodrugs, and pharmaceutically acceptable solvates thereof.

Compounds of Formula (I) are antagonists of $DP_2$.

In one aspect, provided herein are pharmaceutical compositions comprising a therapeutically effective amount of a compound of Formula (I). In some embodiments, the pharmaceutical compositions comprise at least one inactive pharmaceutically acceptable inactive ingredient selected from excipients, diluents, and carriers.

In certain embodiments, presented herein are methods for treating a $PGD_2$-dependent condition or disease in a mammal comprising administering to the mammal a therapeutically effective amount of a compound of Formula (I).

In another aspect, compounds of Formula (I) are used to treat or prevent inflammatory diseases or conditions. Inflammatory conditions include, but are not limited to, asthma, rhinitis, chronic obstructive pulmonary disease, pulmonary hypertension, interstitial lung fibrosis, atherosclerosis, aortic aneurysm, myocardial infarction, and stroke.

In a specific aspect, provided herein is a method for treating asthma in a mammal comprising administering a therapeutically effective amount of a compound provided herein to the mammal in need.

In another aspect, compounds of Formula (I) are used to treat or prevent immunological disorders, including, but are not limited to, allergy or to excessive or inappropriate response to an endogenous or exogenous antigen. In certain embodiments, the immunological disorder that is characterized by immune dysregulation that is not accompanied by inflammation.

In additional aspects, such diseases or conditions are iatrogenic and increases in, or abnormal localization of, $PGD_2$ is induced by other therapies or medical or surgical procedures. In other embodiments, the $PGD_2$-dependent or $PGD_2$ mediated condition or disease is caused by surgery.

In another aspect are methods for treating respiratory diseases or conditions in a mammal comprising administering to the mammal at least once an effective amount of at least one compound of Formula (I). In a further embodiment of this aspect, the respiratory disease is asthma. In a further embodiment of this aspect, the respiratory disease includes, but is not limited to, asthma, adult respiratory distress syndrome, allergic (extrinsic) asthma, non-allergic (intrinsic) asthma, acute severe asthma, chronic asthma, clinical asthma, nocturnal asthma, allergen-induced asthma, aspirin-sensitive asthma, exercise-induced asthma, neutrophillic asthma, isocapnic hyperventilation, child-onset asthma, adult-onset asthma, cough-variant asthma, occupational asthma, steroid-resistant asthma, seasonal asthma, seasonal allergic rhinitis, perennial allergic rhinitis, chronic obstructive pulmonary disease, including chronic bronchitis or emphysema, pulmonary hypertension, interstitial lung fibrosis and/or airway inflammation and cystic fibrosis, and hypoxia.

In another aspect compounds described herein are used for treating rhinitis in a mammal. In a further embodiment of this aspect, compounds described herein are used for treating allergic (extrinsic) rhinitis, non-allergic (intrinsic) rhinitis, chronic rhinitis, allergen-induced rhinitis, aspirin-sensitive rhinitis, child-onset rhinitis, adult-onset rhinitis, occupational rhinitis, steroid-resistant rhinitis, seasonal rhinitis, perennial rhinitis, rhinosinusitis, and rhinopolyposis.

In another aspect are methods for treating chronic obstructive pulmonary disease comprising administering to the mammal at least once an effective amount of a compound of Formula (I). In a further embodiment of this aspect, chronic obstructive pulmonary disease includes, but is not limited to, chronic bronchitis and/or emphysema, pulmonary hypertension, interstitial lung fibrosis and/or airway inflammation and cystic fibrosis.

In another aspect are methods for preventing increased mucosal secretion and/or edema in mammals comprising administering to the mammal at least once an effective amount of a compound of Formula (I).

In another aspect are methods for preventing eosinophil and/or basophil and/or dendritic cell and/or neutrophil and/or monocyte or TH2 cell recruitment comprising administering to the mammal an effective amount of a compound of Formula (I).

In another aspect are methods for treating or preventing ocular inflammation, conjunctivitis, retinitis, scleritis, uveitis, allergic conjunctivitis, vernal keratoconjunctivitis, and papillary conjunctivitis comprising administering to the mammal at least once an effective amount of a compound of Formula (I).

In another aspect, compounds of Formula (I) are used to treat or prevent pain.

In another aspect are methods for preventing or treating acute or chronic disorders involving recruitment or activation of eosinophils comprising administering to the mammal at least once an effective amount of a compound of Formula (I).

In another aspect are methods for treating inflammatory responses of the skin comprising administering to the mammal at least once an effective amount of at least one compound of Formula (I). Such inflammatory responses of the skin include, by way of example, psoriasis, dermatitis, atopic dermatitis, contact dermatitis, eczema, urticaria, rosacea, bullous disorders, collagenoses, Kawasaki Disease, Sjogren-Larsso Syndrome, urticaria, wound healing and scarring. In another aspect are methods for reducing psoriatic lesions in the skin, joints, or other tissues or organs, comprising administering to the mammal an effective amount of a compound of Formula (I). In another aspect are methods for reducing psoriatic lesions in the skin, joints, or other tissues or organs, comprising administering at least once to the mammal an effective amount of a compound of Formula (I).

In a further aspect are methods to modulate the immune response to endogenous or exogenous antigens. In a further aspect are methods to treat acute or chronic allergic responses to exogenous substances that have been ingested such as foods (e.g., peanuts) or drugs (e.g., penicillin, non-steroidal anti-inflammatory drugs or the like).

In another aspect is the use of a compound of Formula (I) in the manufacture of a medicament for treating an inflammatory disease or condition in a mammal in which the activity of at least one $PGD_2$-associated protein contributes to the pathology and/or symptoms of the disease or condition. In one embodiment of this aspect, the $PGD_2$ pathway protein is DP2. In another or further embodiment of this aspect, the inflammatory disease or conditions are respiratory, cardiovascular, or proliferative diseases.

"Cardiovascular disease or conditions," refers to diseases affecting the heart or blood vessels or both, including but not limited to: arrhythmia (atrial or ventricular or both); atherosclerosis and its sequelae; angina; cardiac rhythm disturbances; myocardial ischemia; myocardial infarction; cardiac or vascular aneurysm; vasculitis, stroke; peripheral obstructive arteriopathy of a limb, an organ, or a tissue; reperfusion injury following ischemia of the brain, heart or other organ or tissue; endotoxic, surgical, or traumatic shock; hypertension, valvular heart disease, heart failure, abnormal blood pressure; shock; vasoconstriction (including that associated with migraines); vascular abnormality, inflammation, insufficiency limited to a single organ or tissue.

In any of the aforementioned aspects are further embodiments in which: (a) the effective amount of the compound is systemically administered to the mammal; and/or (b) the effective amount of the compound is administered orally to the mammal; and/or (c) the effective amount of the compound is intravenously administered to the mammal; and/or (d) the effective amount of the compound administered by inhalation; and/or (e) the effective amount of the compound is administered by nasal administration; or and/or (f) the effective amount of the compound is administered by injection to the mammal; and/or (g) the effective amount of the compound is administered topically (dermal) to the mammal;

and/or (h) the effective amount of the compound is administered by ophthalmic administration; and/or (i) the effective amount of the compound is administered rectally to the mammal.

In any of the aforementioned aspects are further embodiments comprising single administrations of the effective amount of the compound, including further embodiments in which (i) the compound is administered once; (ii) the compound is administered to the mammal multiple times over the span of one day; (iii) continually; or (iv) continuously.

In any of the aforementioned aspects involving the treatment of $PGD_2$ dependent diseases or conditions are further embodiments comprising administering at least one additional agent in addition to the administartion of a compound having the structure of Formula (I).

In any of the aforementioned aspects involving the prevention or treatment of inflammation are further embodiments comprising: (a) monitoring inflammation in a mammal; (b) measuring bronchoconstriction in a mammal; (c) measuring eosinophil and/or basophil and/or dendritic cell and/or neutrophil and/or monocyte and/or lymphocyte recruitment in a mammal; (d) monitoring mucosal secretion in a mammal; (e) measuring mucosal edema in a mammal.

Other objects, features and advantages of the compounds, methods and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description.

DETAILED DESCRIPTION OF THE INVENTION

Figure 1:
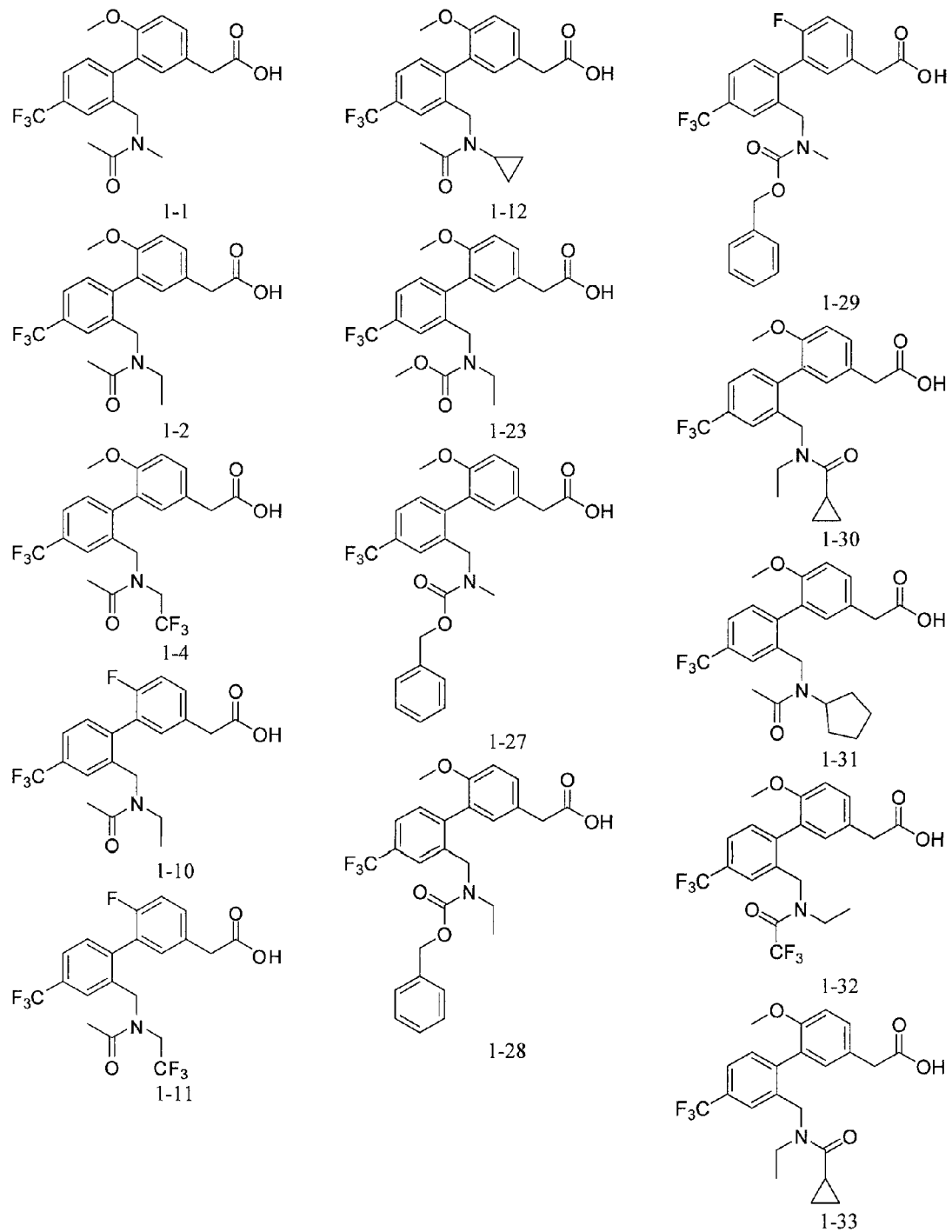
FIG. 1. Illustrative examples of compounds described herein.
Figure 2:
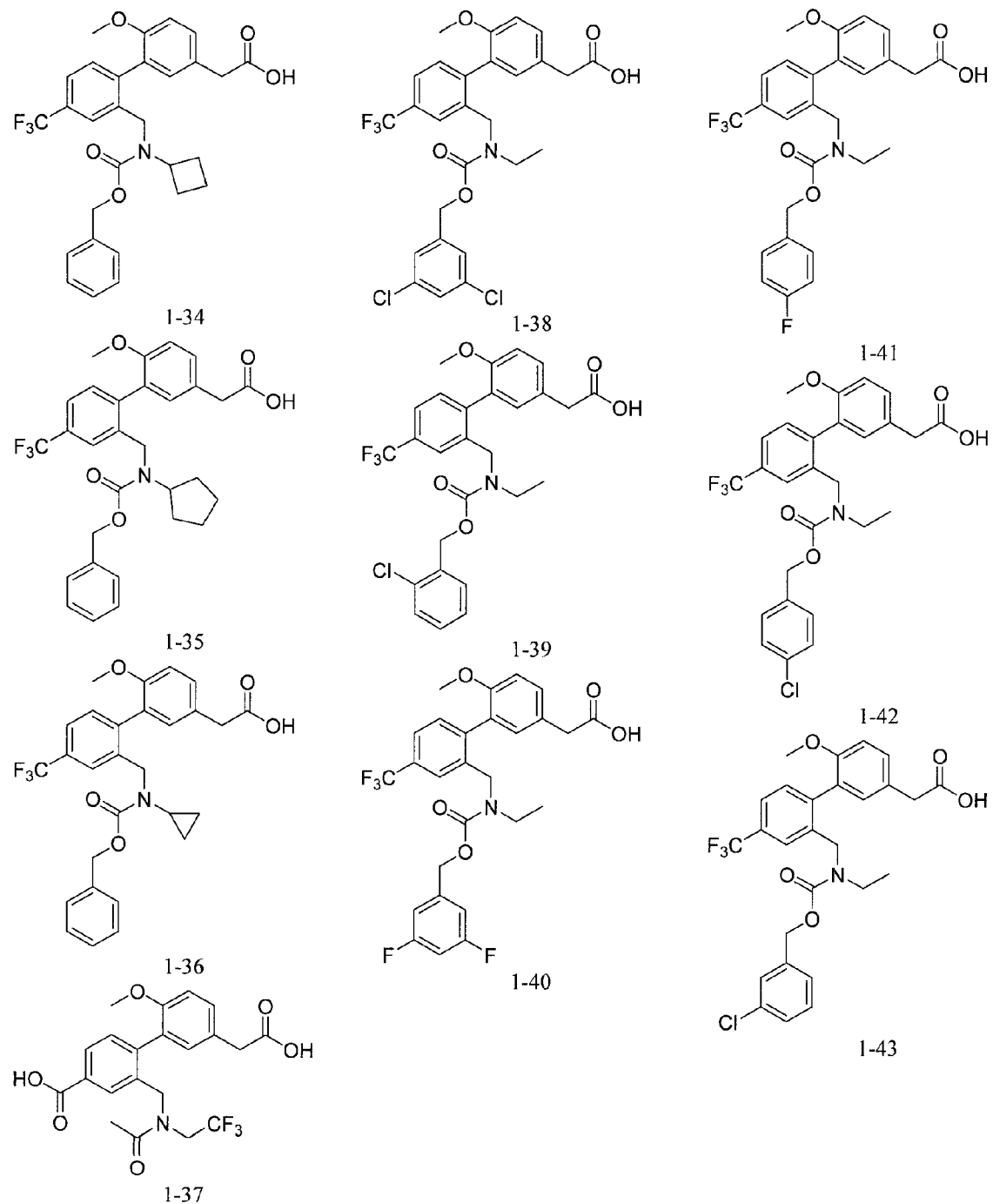
FIG. 2. Illustrative examples of compounds described herein.
Figure 3:
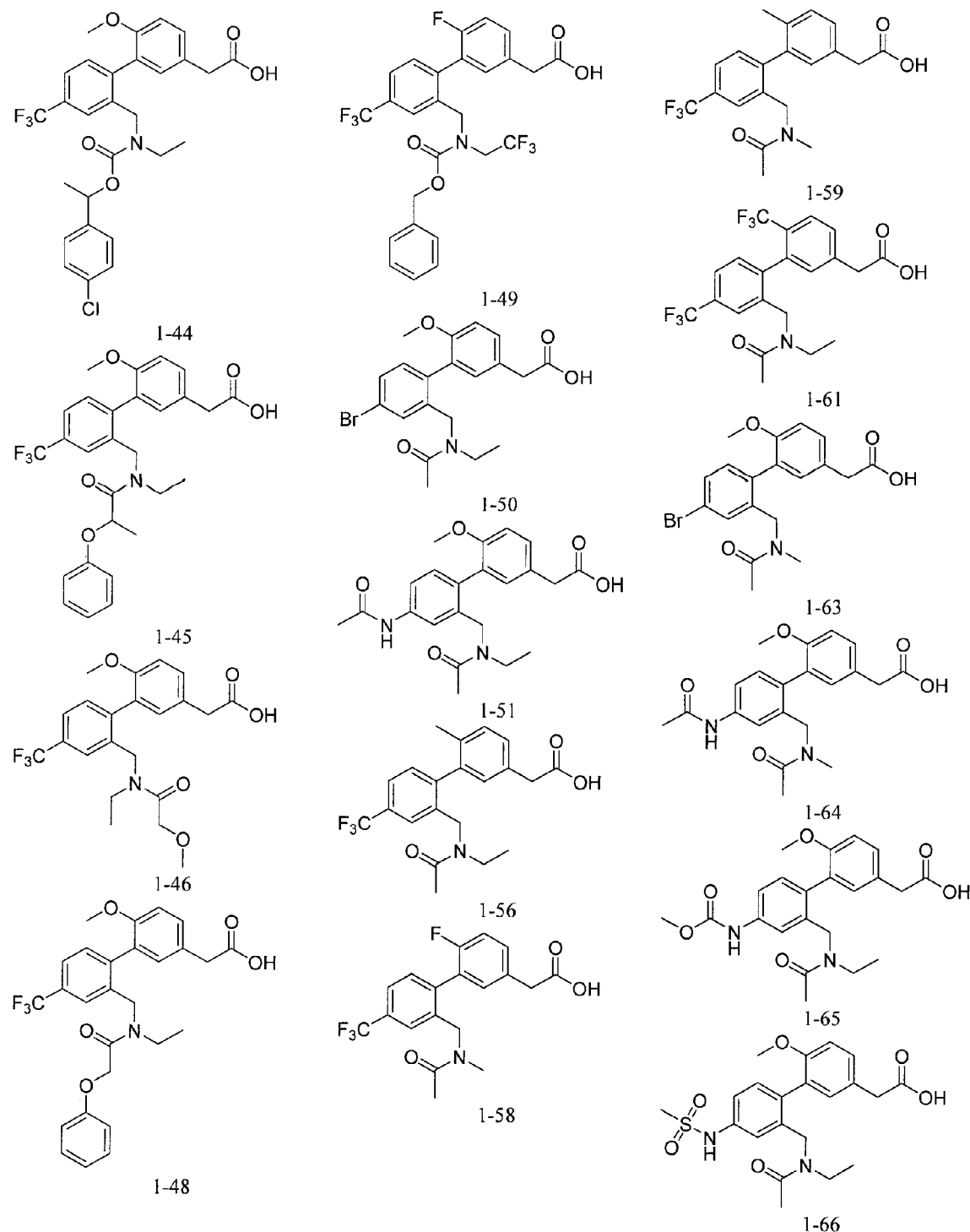
FIG. 3. Illustrative examples of compounds described herein.
Figure 4:
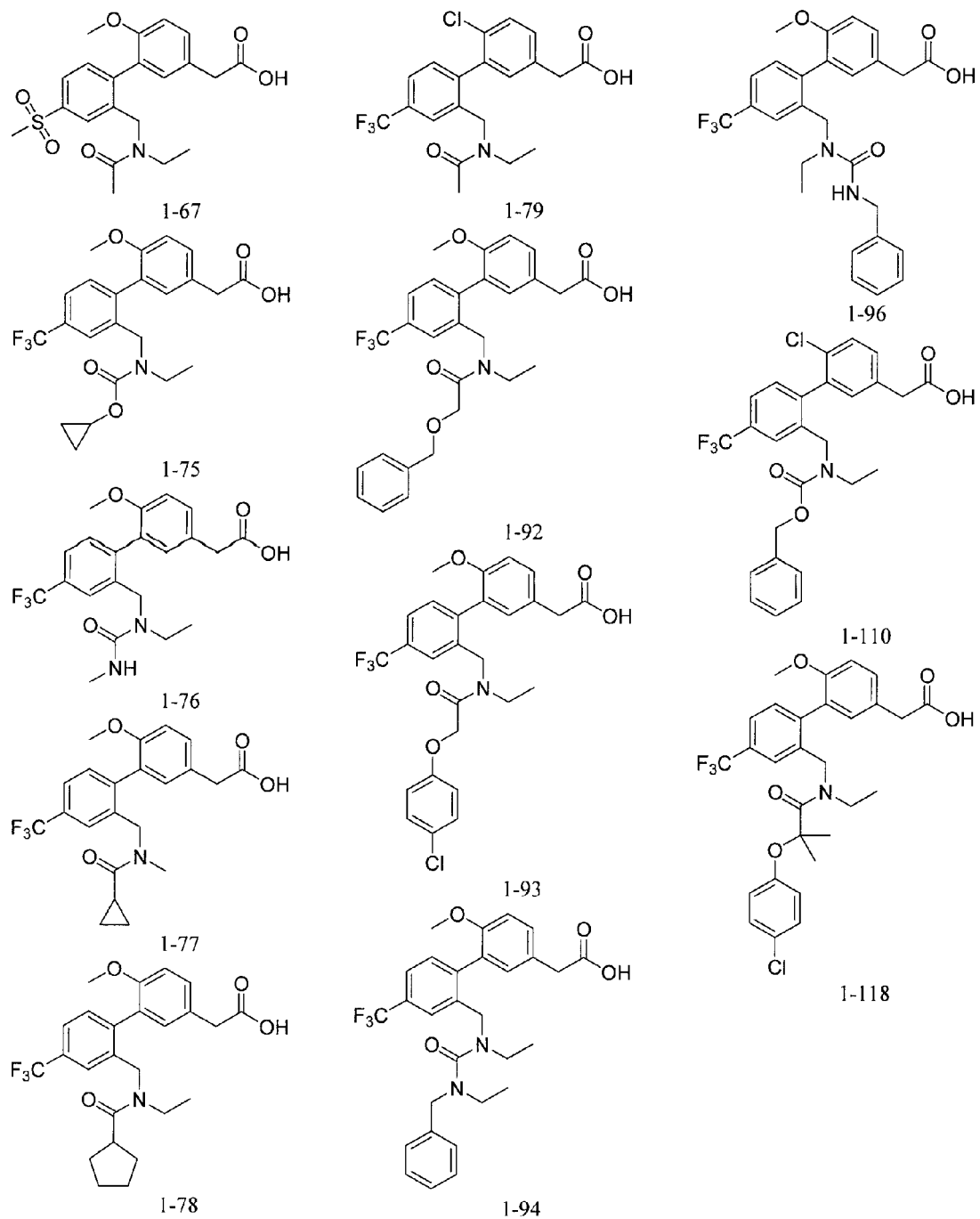
FIG. 4. Illustrative examples of compounds described herein.
Figure 5:
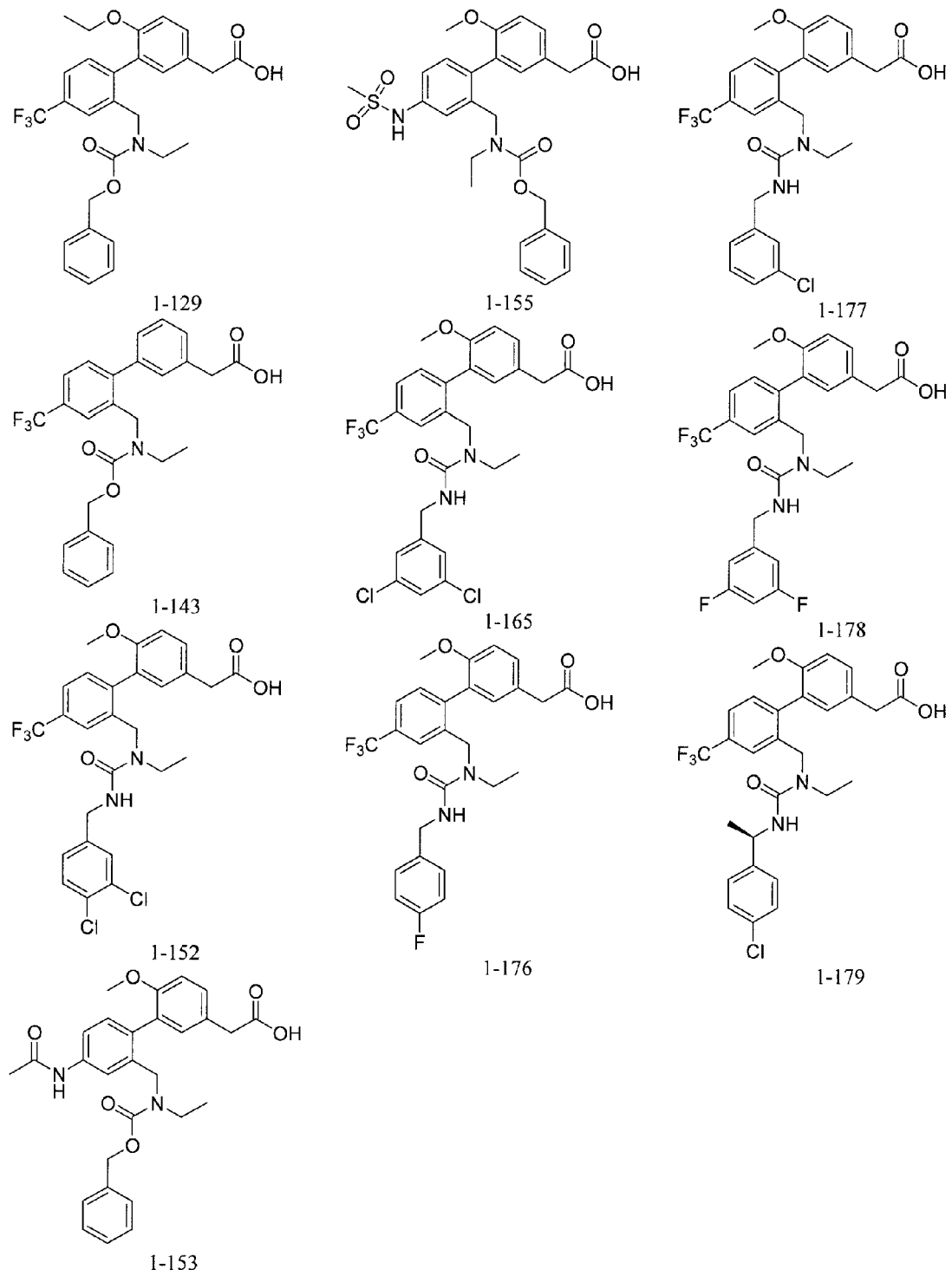
FIG. 5. Illustrative examples of compounds described herein.
Figure 6:
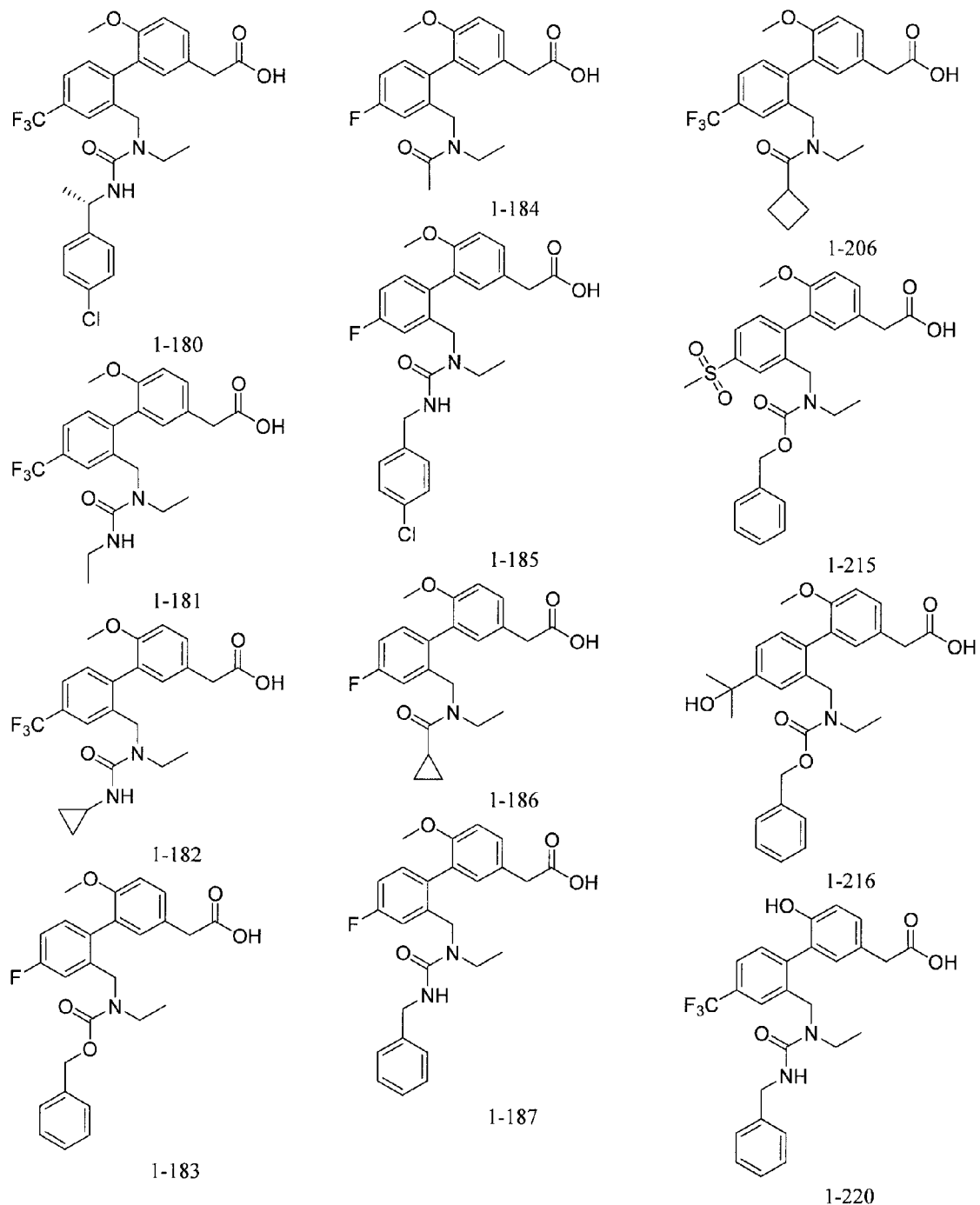
FIG. 6. Illustrative examples of compounds described herein.
Figure 7:
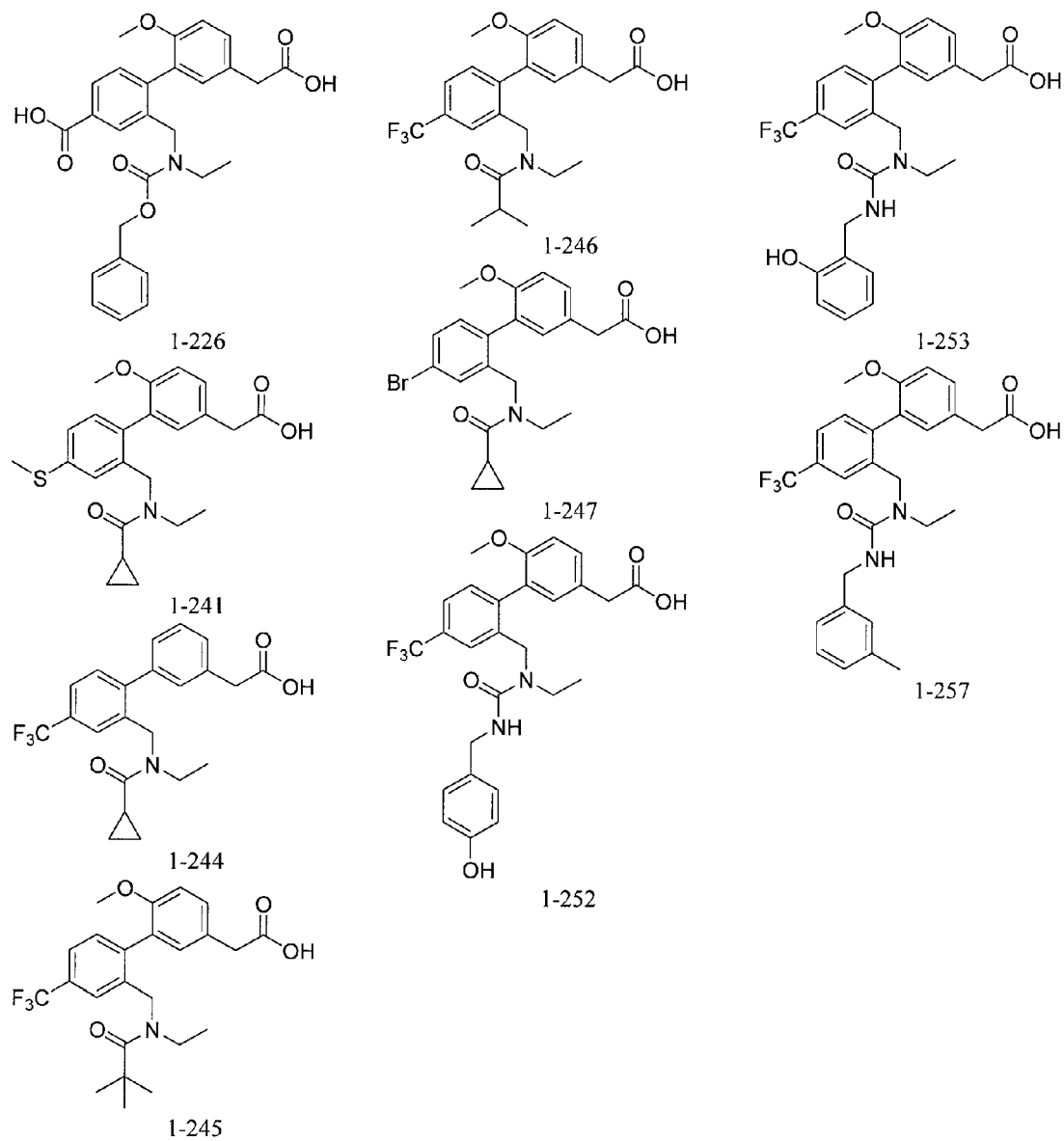
FIG. 7. Illustrative examples of compounds described herein.

Prostaglandin $D_2$ ($PGD_2$) is an acidic lipid derived from the metabolism of arachidonic acid by cyclooxygenases and $PGD_2$ synthases. $PGD_2$ is produced by mast cells, macrophages and $T_H2$ lymphocytes in response to local tissue damage as well as in response allergic inflammation observed in diseases such as asthma, rhinitis, and atopic dermatitis. Exogenous $PGD_2$ applied to bronchial airways elicits many responses that are characteristic of acute asthma.

Activation of $DP_2$ is associated with chemotaxis and activation of $T_H2$ lymphocytes, eosinophils and basophils. $PGD_2$ binds to $DP_2$ and mediates many of its effects through a $G_i$-dependent elevation of intracellular calcium levels and reduction of cyclic AMP. In $T_H2$ lymphocytes, IL4, IL5 and IL13 cytokine production are also stimulated by $DP_2$ activation. These cytokines have been implicated in numerous biological actions including, by way of example only, immunoglobulin E production, airway response, mucous secretion, and eosinophil recruitment.

In the brain and central nervous system, $PGD_2$ is produced and thought to function in pain perception and sleep regulation. In other tissues, $PGD_2$ is produced primarily in immunoglobulin E (IgE) activated mast cells and to a lesser extent, in macrophages, dendritic cells, T helper 2 ($T_H2$) lymphocytes and other leukocytes. In the cell, $PGD_2$ is rapidly metabolized and converted to other downstream effectors including $\Delta^{12}PGJ_2$, $9\alpha11\beta PGF_2$, 13,14-dihydro-15-keto-$PGD_2$, and 15-deoxy-$\Delta^{12,14}PGD_2$.

Mast-cell-derived $PGD_2$ is produced in high concentrations in response to an allergen challenge. Studies in preclinical species have observed the following features when $PGD_2$ is applied to in vivo preparations, or its overproduction is engineered by genetic manipulation:

Vasodilatation leading to erythema (flare) and -potentiation of oedema (wheal).

Recruitment of eosinophils and TH2 lymphocytes.

Modulation of TH2-cytokine production.

Bronchoconstriction.

Injection of $PGD_2$ into human skin has been shown to produce a long lasting erythema, to potentiate the effects of other mediators on induration and leukocyte infiltration in human skin and to enhance oedema formation in rat skin. It is most likely that these effects of $PGD_2$, like those of other vasodilator prostaglandins, are due to an increased blood flow to the inflamed lesion and are, therefore, most likely to be mediated predominantly by the $DP_1$ receptor. Although these observations make it clear that $DP_1$ mediates the vascular effects of $PGD_2$, the capacity of $PGD_2$ to promote the cellular changes associated with inflammation is not due to an action on $DP_1$.

Much of $PGD_2$'s pro-inflammatory activity is through interaction with $DP_2$. $DP_2$ is a G-protein coupled receptor and is typically highly expressed in $T_H2$ lymphocytes, eosinophils and basophils. $DP_2$ activation functions to directly activate and recruit $T_H2$ lymphocytes and eosinophils. Activated $T_H2$ lymphocytes produce and secrete inflammatory cytokines including IL4, IL5, and IL13. Despite binding $PGD_2$ with a similar affinity as $DP_1$, $DP_2$ is not structurally related to $DP_1$ and signals through a different mechanism- the effects of $DP_2$ are mediated through Gi-dependent elevation in intracellular calcium levels and reduction in intracellular levels of cyclic AMP. $DP_2$ activation is important in eosinophil recruitment in response to allergic challenge in such tissues as nasal mucosa, bronchial airways, and skin. The application of either $PGD_2$ or selective $DP_2$ agonists both exacerbate and enhance allergic responses in lung and skin. $DP_2$ activation appears to have a crucial role in mediating allergic responses. The use of antagonists of $PGD_2$ activation of the $DP_2$ receptor is an approach to treat the inflammatory component of inflammatory diseases or conditions, respiratory diseases or conditions, allergic diseases or conditions, such as asthma, rhinitis, and dermatitis, among others.

Compounds

Compounds of Formula (I) have the following structure:

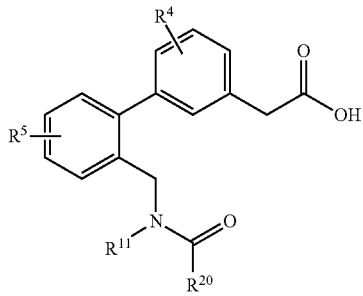

Formula (I)

wherein, $R^4$ is selected from H, halogen, —CN, —OH, $C_1$-$C_4$alkyl, $C_1$-$C_4$alkoxy, $C_1$-$C_4$fluoroalkyl, $C_1$-$C_4$fluoroalkoxy, and $C_1$-$C_4$heteroalkyl;

$R^5$ is H, halogen, —CN, —NO$_2$, —OH, —S(=O)$_2$R$^{12}$, —NHS(=O)$_2$R$^{12}$, —C(=O)R$^{12}$, —OC(=O)R$^{12}$, —CO$_2$R$^{13}$, —N(R$^{13}$)$_2$, —C(=O)N(R$^{13}$)$_2$, —NHC(=O)R$^{12}$, —C(OH)(R$^{13}$)$_2$, $C_1$-$C_4$alkyl, $C_1$-$C_4$fluoroalkyl, $C_1$-$C_4$fluoroalkoxy, $C_1$-$C_4$alkoxy, $C_1$-$C_4$heteroalkyl or —SR$^{12}$;

$R^{20}$ is $C_1$-$C_4$alkyl, $C_3$-$C_6$cycloalkyl, —CH$_2$O—$C_1$-$C_4$alkyl, —CH$_2$O-(substituted or unsubstituted phenyl), —CH(CH$_3$)—O-(substituted or unsubstituted phenyl), —C(CH$_3$)$_2$—O-(substituted or unsubstituted phenyl), —CH$_2$OCH$_2$-(substituted or unsubstituted phenyl), —OC$_1$-$C_4$alkyl, —O—CH$_2$-(substituted or unsubstituted phenyl), —O—CH(CH$_3$)-(substituted or unsubstituted phenyl), —NR$^{16}$C$_1$-$C_4$alkyl, —NR$^{16}$—CH$_2$-(substituted or unsubstituted phenyl), or —NR$^{16}$—CH(CH$_3$)-(substituted or unsubstituted phenyl), wherein if the phenyl of R$^{20}$ is substituted, then the phenyl is substituted with 0, 1, or 2 R$^{21}$ groups;

$R^{21}$ is selected from halogen, —OH, —OCH$_3$, $C_1$-$C_4$alkyl, and —CF$_3$;

$R^{16}$ is H or $C_1$-$C_4$alkyl;

$R^{11}$ is $C_1$-$C_4$alkyl, $C_1$-$C_4$fluoroalkyl, or $C_3$-$C_6$cycloalkyl;

$R^{12}$ is $C_1$-$C_4$alkyl, $C_1$-$C_4$heteroalkyl, or $C_1$-$C_4$fluoroalkyl;

each $R^{13}$ is independently selected from H, $C_1$-$C_4$alkyl, $C_1$-$C_4$heteroalkyl, and $C_1$-$C_4$fluoroalkyl.

In one aspect, the compound of Formula (I) has the following structure:

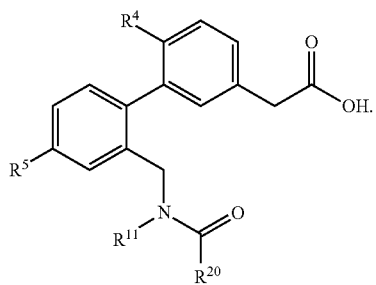

For any and all of the embodiments, substituents can be selected from among from a subset of the listed alternatives.

For example, in some embodiments, $R^{11}$ is —CH$_3$, —CH$_2$CH$_3$, —CF$_3$, —CH$_2$CF$_3$, cyclopropyl, cyclobutyl, or cyclopentyl. In other embodiments, $R^{11}$ is —CH$_3$, —CH$_2$CH$_3$, —CF$_3$, or —CH$_2$CF$_3$. In other embodiments, $R^{11}$ is —CH$_3$, —CH$_2$CH$_3$, or —CH$_2$CF$_3$. In yet other embodiments, $R^{11}$ is cyclopropyl, cyclobutyl, or cyclopentyl. In some embodiments, $R^{11}$ is —CH$_3$, or —CH$_2$CH$_3$. In yet other embodiments, $R^{11}$ is —CH$_2$CH$_3$.

In some embodiments, $R^4$ is H, F, Cl, Br, —OH, —CH$_3$, —OCH$_3$, —CF$_3$, or —OCF$_3$. In some other embodiments, $R^4$ is —OCH$_3$.

In some embodiments, $R^5$ is H, halogen, —CN, —NO$_2$, —OH, —S(=O)$_2$CH$_3$, —NHS(=O)$_2$CH$_3$, —C(=O)CH$_3$, —OC(=O)CH$_3$, —CO$_2$H, —CO$_2$CH$_3$, —CO$_2$CH$_2$CH$_3$, —NH$_2$, —C(=O)NH$_2$, —NHC(=O)CH$_3$, —CH$_3$, —CF$_3$, —OCF$_3$, —OCH$_3$, —CH$_2$OH, or —C(CH$_3$)$_2$OH. In some other embodiments, $R^5$ is H, F, Cl, Br, —CH$_3$, —CF$_3$, —OCF$_3$, or —OCH$_3$. In some other embodiments, $R^5$ is —CH$_3$ or —CF$_3$. In some embodiments, $R^5$ is —CF$_3$.

In some embodiments, $R^{20}$ is $C_1$-$C_4$alkyl, $C_3$-$C_6$cycloalkyl, —CH$_2$O—$C_1$-$C_4$alkyl, —CH$_2$O-phenyl, —CH(CH$_3$)—O-phenyl, —C(CH$_3$)$_2$—O-phenyl, —CH$_2$OCH$_2$-phenyl, —OC$_1$-$C_4$alkyl, —O—CH$_2$-phenyl, —O—CH(CH$_3$)-phenyl, —NR$^{16}$C$_1$-$C_4$alkyl, —NR$^{16}$—CH$_2$-phenyl, or —NR$^{16}$—CH(CH$_3$)-phenyl. In one aspect, the phenyl group of $R^{20}$ is substituted with one or two $R^{21}$ groups.

In some embodiments, $R^{20}$ is —CH$_3$, —CH$_2$CH$_3$, —CH(CH$_3$)$_2$, —C(CH$_3$)$_3$, cyclopropyl, cyclobutyl, cyclopentyl, cyclohexyl, —CH$_2$OCH$_3$, —CH$_2$O-(substituted or unsubstituted phenyl), —CH(CH$_3$)—O-(substituted or unsubstituted phenyl), —C(CH$_3$)$_2$—O-(substituted or unsubstituted phenyl), —CH$_2$OCH$_2$-(substituted or unsubstituted phenyl), wherein if the phenyl of R$^{20}$ is substituted, then the phenyl is substituted with 0, 1, or 2 R$^{21}$ groups; each R$^{21}$ is independently selected from F, Cl, Br, —OH, —OCH$_3$, —CH$_3$, and —CF$_3$.

In some embodiments, $R^{20}$ is —CH$_3$, —CH$_2$CH$_3$, cyclopropyl, cyclobutyl, cyclopentyl, cyclohexyl, —CH$_2$OCH$_3$, —CH$_2$O-(substituted or unsubstituted phenyl), —CH(CH$_3$)—O-(substituted or unsubstituted phenyl), —C(CH$_3$)$_2$—O-(substituted or unsubstituted phenyl), —CH$_2$OCH$_2$-(substituted or unsubstituted phenyl), wherein if the phenyl of R$^{20}$ is substituted, then the phenyl is substituted with 0, 1, or 2 R$^{21}$ groups; each R$^{21}$ is independently selected from F, Cl, Br, —OH, —OCH$_3$, —CH$_3$, and —CF$_3$.

In other embodiments, $R^{20}$ is —CH$_3$, cyclopropyl, —CH$_2$OCH$_3$, —CH$_2$O-(substituted or unsubstituted phenyl), —CH$_2$OCH$_2$-(substituted or unsubstituted phenyl), wherein if the phenyl of R$^{20}$ is substituted, then the phenyl is substituted with 0, 1, or 2 R$^{21}$ groups; each R$^{20}$ is independently selected from F, Cl, Br, —OH, —OCH$_3$, —CH$_3$, and —CF$_3$.

In other embodiments, $R^{20}$ is $C_1$-$C_4$alkyl, $C_3$-$C_6$cycloalkyl, or —CH$_2$O—$C_1$-$C_4$alkyl. In other embodiments, $R^{20}$ is $C_1$-$C_4$alkyl. In other embodiments, $R^{20}$ is —CH$_3$. In some other embodiments, $R^{20}$ is $C_3$-$C_6$cycloalkyl. In other embodiments, $R^{20}$ is cyclopropyl.

In some embodiments, $R^{20}$ is —CH$_2$O—C$_1$-C$_4$alkyl, —CH$_2$O-(substituted or unsubstituted phenyl), —CH(CH$_3$)—O-(substituted or unsubstituted phenyl), —C(CH$_3$)$_2$—O-(substituted or unsubstituted phenyl), or —CH$_2$OCH$_2$-(substituted or unsubstituted phenyl), wherein if the phenyl of $R^{20}$ is substituted, then the phenyl is substituted with 0, 1, or 2 $R^{21}$ groups.

In yet other embodiments, $R^{20}$ is —OC$_1$-C$_4$alkyl, —O—CH$_2$-(substituted or unsubstituted phenyl), or —O—CH(CH$_3$)-(substituted or unsubstituted phenyl); wherein if the phenyl of $R^{20}$ is substituted, then the phenyl is substituted with 0, 1, or 2 $R^{21}$ groups; each $R^{21}$ is independently selected from F, Cl, Br, —OH, —OCH$_3$, —CH$_3$, and —CF$_3$.

In yet other embodiments, $R^{20}$ is —OC$_1$-C$_4$alkyl. In some embodiments, $R^{20}$ is —O—CH$_2$-(substituted or unsubstituted phenyl), wherein if the phenyl of $R^{20}$ is substituted, then the phenyl is substituted with 0, 1, or 2 $R^{21}$ groups.

In some embodiments, each $R^{21}$ is independently selected from F, Cl, and Br.

In one aspect, the compound of Formula (I) has the following structure:

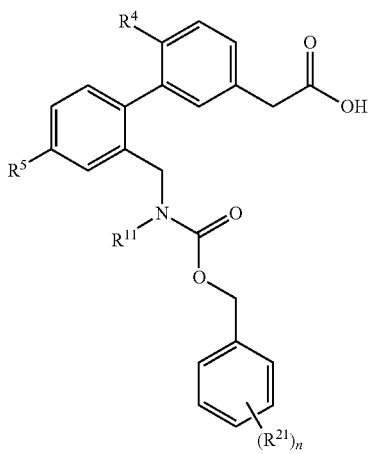

wherein, n is 0, 1, or 2;

In one aspect, $R^4$ is F, Cl, Br, —CH$_3$, —OCH$_3$, —CF$_3$, or —OCF$_3$. In one aspect, $R^5$ is F, Cl, Br, —CH$_3$, —CF$_3$, —OCF$_3$, or —OCH$_3$. In one aspect, $R^{11}$ is —CH$_3$, —CH$_2$CH$_3$, or —CH$_2$CF$_3$.

In one aspect, n is 0. In another aspect, n is 1. In yet another aspect, n is 2.

In some embodiments, $R^{20}$ is —NR$^{16}$C$_1$-C$_4$alkyl, —NR$^{16}$—CH$_2$-(substituted or unsubstituted phenyl), or —NR$^{16}$—CH(CH$_3$)-(substituted or unsubstituted phenyl), wherein if the phenyl of $R^{20}$ is substituted, then the phenyl is substituted with 0, 1, or 2 $R^{21}$ groups; each $R^{21}$ is independently selected from F, Cl, Br, —OH, —OCH$_3$, —CH$_3$, and —CF$_3$; $R^{16}$ is H, —CH$_3$, or —CH$_2$CH$_3$.

In some embodiments, $R^{16}$ is H, —CH$_3$, or —CH$_2$CH$_3$. In other embodiments, $R^{16}$ is H.

In some embodiments, $R^{20}$ is —NR$^{16}$C$_1$-C$_4$alkyl.

In some embodiments, $R^{20}$ is —NR$^{16}$—CH$_2$-(substituted or unsubstituted phenyl), or —NR$^{16}$—CH(CH$_3$)-(substituted or unsubstituted phenyl), wherein if the phenyl of $R^{20}$ is substituted, then the phenyl is substituted with 0, 1, or 2 $R^{21}$ groups.

In some embodiments, $R^{20}$ is —NH—CH$_2$-(substituted or unsubstituted phenyl), wherein if the phenyl of $R^{20}$ is substituted, then the phenyl is substituted with 0, 1, or 2 $R^{21}$ groups.

In some embodiments, each $R^{21}$ is independently selected from F, Cl, Br, —OH, —OCH$_3$, —CH$_3$, and —CF$_3$. In other embodiments, each $R^{21}$ is independently selected from F, Cl, and Br.

In one aspect, the compound of Formula (I) has the following structure:

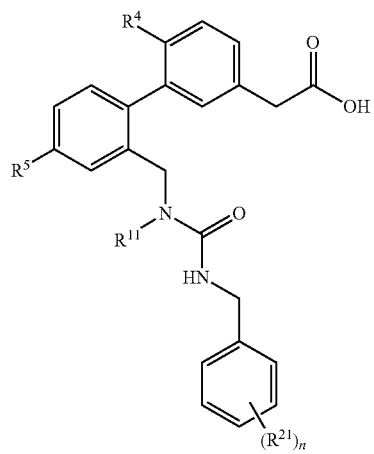

wherein, n is 0, 1, or 2.

each $R^{21}$ is independently selected from F, Cl, Br, —OH, —OCH$_3$, —CH$_3$, and —CF$_3$.

In one aspect, $R^4$ is F, Cl, Br, —CH$_3$, —OCH$_3$, —CF$_3$, or —OCF$_3$. In one aspect, $R^5$ is F, Cl, Br, —CH$_3$, —CF$_3$, —OCF$_3$, or —OCH$_3$.

In one aspect, $R^{11}$ is —CH$_3$, —CH$_2$CH$_3$, or —CH$_2$CF$_3$.

In some embodiments, wherein, n is 0, 1, or 2; $R^4$ is —OCH$_3$; $R^5$ is —CF$_3$; $R^{11}$ is —CH$_3$, or —CH$_2$CH$_3$; each $R^{21}$ is independently selected from F, Cl, and Br.

In one aspect, n is 0. In another aspect, n is 1. In yet another aspect, n is 2.

In one aspect, $R^4$ is —OCH$_3$. In one aspect, $R^5$ is —CF$_3$. In one aspect, $R^{11}$ is —CH$_3$, or —CH$_2$CH$_3$. In one aspect, $R^{11}$ is —CH$_2$CH$_3$.

In one aspect, $R^{12}$ is C$_1$-C$_4$alkyl or C$_1$-C$_4$fluoroalkyl. In one aspect, $R^{12}$ is C$_1$-C$_4$alkyl.

In one aspect, each $R^{13}$ is independently selected from H, C$_1$-C$_4$alkyl, and C$_1$-C$_4$fluoroalkyl. In one aspect, each $R^{13}$ is independently selected from H and C$_1$-C$_4$alkyl.

In one aspect, $R^4$ is as defined in Table 1. In one aspect, $R^5$ is as defined in Table 1. In one aspect, $R^{20}$ is as defined in Table 1. In one aspect, $R^{11}$ is as defined in Table 1.

Any combination of the groups described above for the various variables is contemplated herein. Throughout the specification, groups and substituents thereof are chosen by one skilled in the field to provide stable moieties and compounds.

In one aspect, compounds of Formula (I) include, but are not limited to, those described in Table 1:

TABLE 1

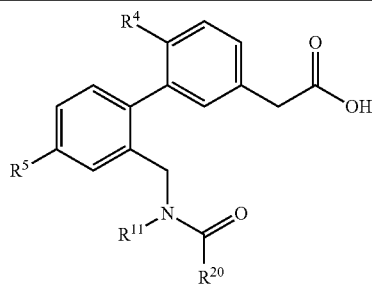

| Cmpd # | R⁴ | R⁵ | R¹¹ | R²⁰ | M + H |
|---|---|---|---|---|---|
| 1-1 | OCH₃ | CF₃ | CH₃ | —CH₃ | 396 |
| 1-2 | OCH₃ | CF₃ | CH₂CH₃ | —CH₃ | 410 |
| 1-3 | OCH₃ | CF₃ | CH₂C(CH₃)₃ | —CH₃ | 452 |
| 1-4 | OCH₃ | CF₃ | CH₂CF₃ | —CH₃ | 464 |
| 1-10 | F | CF₃ | CH₂CH₃ | —CH₃ | 398 |
| 1-11 | F | CF₃ | CH₂CF₃ | —CH₃ | 452 |
| 1-12 | OCH₃ | CF₃ | Cyclopropyl | —CH₃ | 422 |
| 1-23 | OCH₃ | CF₃ | CH₂CH₃ | —OCH₃ | 426 |
| 1-27 | OCH₃ | CF₃ | CH₃ | —OCH₂Ph | 488 |
| 1-28 | OCH₃ | CF₃ | CH₂CH₃ | —OCH₂Ph | 502 |
| 1-29 | F | CF₃ | CH₃ | —OCH₂Ph | 476 |
| 1-30 | OCH₃ | CF₃ | Cyclobutyl | —CH₃ | 436 |
| 1-31 | OCH₃ | CF₃ | Cyclopentyl | —CH₃ | 450 |
| 1-32 | OCH₃ | CF₃ | CH₂CH₃ | —CF₃ | 464 |
| 1-33 | OCH₃ | CF₃ | CH₂CH₃ | -(cyclopropyl) | 436 |
| 1-34 | OCH₃ | CF₃ | Cyclobutyl | —OCH₂Ph | 528 |
| 1-35 | OCH₃ | CF₃ | Cyclopentyl | —OCH₂Ph | 542 |
| 1-36 | OCH₃ | CF₃ | Cyclopropyl | —OCH₂Ph | 514 |
| 1-37 | OCH₃ | CO₂H | CH₂CF₃ | —CH₃ | 440 |
| 1-38 | OCH₃ | CF₃ | CH₂CH₃ | —OCH₂-(3,5-dichlorophenyl) | 571 |
| 1-39 | OCH₃ | CF₃ | CH₂CH₃ | —OCH₂-(2-chlorophenyl) | 536 |
| 1-40 | OCH₃ | CF₃ | CH₂CH₃ | —OCH₂-(3,5-difluorophenyl) | 538 |
| 1-41 | OCH₃ | CF₃ | CH₂CH₃ | —OCH₂-(4-fluorophenyl) | 520 |
| 1-42 | OCH₃ | CF₃ | CH₂CH₃ | —OCH₂-(4-chlorophenyl) | 536 |
| 1-43 | OCH₃ | CF₃ | CH₂CH₃ | —OCH₂-(3-chlorophenyl) | 536 |
| 1-44 | OCH₃ | CF₃ | CH₂CH₃ | —O—CH(CH₃)(4-chlorophenyl) | 550 |
| 1-45 | OCH₃ | CF₃ | CH₂CH₃ | —CH(CH₃)(OPh) | 516 |
| 1-46 | OCH₃ | CF₃ | CH₂CH₃ | —CH₂OCH₃ | 440 |
| 1-48 | OCH₃ | CF₃ | CH₂CH₃ | —CH₂OPh | 502 |
| 1-49 | F | CF₃ | CH₂CF₃ | —OCH₂Ph | 544 |
| 1-50 | OCH₃ | Br | CH₂CH₃ | —CH₃ | |
| 1-51 | OCH₃ | NH—C(=O)—CH₃ | CH₂CH₃ | —CH₃ | |
| 1-56 | CH₃ | CF₃ | CH₂CH₃ | —CH₃ | |
| 1-58 | F | CF₃ | CH₃ | —CH₃ | |
| 1-59 | CH₃ | CF₃ | CH₃ | —CH₃ | |
| 1-60 | Cyclo-propyl | CF₃ | CH₂CH₃ | —CH₃ | |
| 1-61 | CF₃ | CF₃ | CH₂CH₃ | —CH₃ | |
| 1-63 | OCH₃ | Br | CH₃ | —CH₃ | |
| 1-64 | OCH₃ | NH—C(=O)—CH₃ | CH₃ | —CH₃ | |
| 1-65 | OCH₃ | NH—C(=O)—OCH₃ | CH₂CH₃ | —CH₃ | |
| 1-66 | OCH₃ | NH—SO₂CH₃ | CH₂CH₃ | —CH₃ | |
| 1-67 | OCH₃ | SO₂CH₃ | CH₂CH₃ | —CH₃ | |
| 1-75 | OCH₃ | CF₃ | CH₂CH₃ | —O-(cyclopropyl) | |
| 1-76 | OCH₃ | CF₃ | CH₂CH₃ | —NHCH₃ | |
| 1-77 | OCH₃ | CF₃ | CH₃ | -(cyclopropyl) | |
| 1-78 | OCH₃ | CF₃ | CH₂CH₃ | -(cyclopentyl) | |
| 1-79 | Cl | CF₃ | CH₂CH₃ | —CH₃ | |
| 1-92 | OCH₃ | CF₃ | CH₂CH₃ | —CH₂OCH₂Ph | |
| 1-93 | OCH₃ | CF₃ | CH₂CH₃ | —CH₂O-(4-chlorophenyl) | |
| 1-94 | OCH₃ | CF₃ | CH₂CH₃ | —N(CH₂CH₃)(CH₂Ph) | |
| 1-96 | OCH₃ | CF₃ | CH₂CH₃ | —NHCH₂Ph | 501 |
| 1-110 | Cl | CF₃ | CH₂CH₃ | —OCH₂Ph | 506 |
| 1-118 | OCH₃ | CF₃ | CH₂CH₃ | —C(CH₃)₂—O-(4-chlorophenyl) | 565 |
| 1-128 | OCH₂—Ph | CF₃ | CH₂CH₃ | —OCH₂Ph | 578 |
| 1-129 | OCH₂—CH₃ | CF₃ | CH₂CH₃ | —OCH₂Ph | 516 |
| 1-130 | OCH₂-(cyclo-propyl) | CF₃ | CH₂CH₃ | —OCH₂Ph | 542 |
| 1-143 | H | H | CH₂CH₃ | —OCH₂Ph | 472 |
| 1-152 | OCH₃ | CF₃ | CH₂CH₃ | —NHCH₂-(3,4-dichlorophenyl) | 569 |
| 1-153 | OCH₃ | NH—(C=O)—CH₃ | CH₂CH₃ | —OCH₂Ph | |
| 1-155 | OCH₃ | NH—SO₂—CH₃ | CH₂CH₃ | —OCH₂Ph | |
| 1-165 | OCH₃ | CF₃ | CH₂CH₃ | —NHCH₂-(3,5-dichlorophenyl) | 570 |
| 1-176 | OCH₃ | CF₃ | CH₂CH₃ | —NHCH₂-(4-fluorophenyl) | 519 |

TABLE 1-continued

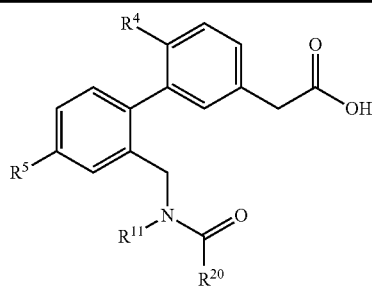

| Cmpd # | $R^4$ | $R^5$ | $R^{11}$ | $R^{20}$ | M + H |
|---|---|---|---|---|---|
| 1-177 | OCH₃ | CF₃ | CH₂CH₃ | —NHCH₂-(3-chlorophenyl) | 535 |
| 1-178 | OCH₃ | CF₃ | CH₂CH₃ | —NHCH₂-(3,5-difluorophenyl) | 537 |
| 1-179 | OCH₃ | CF₃ | CH₂CH₃ | (R)—NH—CH(CH₃)(4-chlorophenyl) | 549 |
| 1-180 | OCH₃ | CF₃ | CH₂CH₃ | (S)—NH—CH(CH₃)(4-chlorophenyl) | 549 |
| 1-181 | OCH₃ | CF₃ | CH₂CH₃ | —NHCH₂CH₃ | 439 |
| 1-182 | OCH₃ | CF₃ | CH₂CH₃ | —NH-(cyclopropyl) | 451 |
| 1-183 | OCH₃ | F | CH₂CH₃ | —OCH₂Ph | 452 |
| 1-184 | OCH₃ | F | CH₂CH₃ | —CH₃ | 360 |
| 1-185 | OCH₃ | F | CH₂CH₃ | —NHCH₂-(4-chlorophenyl) | 486 |
| 1-186 | OCH₃ | F | CH₂CH₃ | -(cyclopropyl) | 386 |
| 1-187 | OCH₃ | F | CH₂CH₃ | —NHCH₂Ph | 451 |
| 1-206 | OCH₃ | CF₃ | CH₂CH₃ | -(cyclobutyl) | 450 |
| 1-215 | OCH₃ | SO₂—CH₃ | CH₂CH₃ | —OCH₂Ph | 512 |
| 1-216 | OCH₃ | C(CH₃)₂—(OH) | CH₂CH₃ | —OCH₂Ph | 492 |
| 1-220 | OH | CF₃ | CH₂CH₃ | —NHCH₂Ph | 487 |
| 1-226 | OCH₃ | COOH | CH₂CH₃ | —OCH₂Ph | 478 |
| 1-241 | OCH₃ | SCH₃ | CH₂CH₃ | -(cyclopropyl) | 414 |
| 1-244 | H | CF₃ | CH₂CH₃ | -(cyclopropyl) | 406 |
| 1-245 | OCH₃ | CF₃ | CH₂CH₃ | —C(CH₃)₃ | 452 |
| 1-246 | OCH₃ | CF₃ | CH₂CH₃ | —CH(CH₃)₂ | 438 |
| 1-247 | OCH₃ | Br | CH₂CH₃ | -(cyclopropyl) | 446 |
| 1-252 | OCH₃ | CF₃ | CH₂CH₃ | —NHCH₂-(4-hydroxyphenyl) | 517 |
| 1-253 | OCH₃ | CF₃ | CH₂CH₃ | —NHCH₂-(2-hydroxyphenyl) | 517 |
| 1-257 | OCH₃ | CF₃ | CH₂CH₃ | —NHCH₂-(3-hydroxyphenyl) | 517 |

M + H refers to mass spectrometric data, where M represents the molecular ion peak.

Further Forms of Compounds

In certain embodiments, compounds of Formula (I) are prepared as pharmaceutically acceptable salts by reacting the free base form of the compound with a pharmaceutically acceptable inorganic or organic acid, including, but not limited to, inorganic acids such as hydrochloric acid, hydrobromic acid, sulfuric acid, nitric acid, phosphoric acid metaphosphoric acid, and the like; and organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, p-toluenesulfonic acid, tartaric acid, trifluoroacetic acid, citric acid, benzoic acid, 3-(4-hydroxybenzoyl)benzoic acid, cinnamic acid, mandelic acid, arylsulfonic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, and muconic acid.

Pharmaceutically acceptable salts are also obtained by reacting a compound of Formula (I) with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, and salts with amino acids such as arginine, lysine, and the like.

In other embodiments, compounds of Formula (I) are prepared as a pharmaceutically acceptable salts by reacting the free acid form of the compound with a pharmaceutically acceptable inorganic or organic base, including, but not limited to organic bases such as ethanolamine, diethanolamine, triethanolamine, tromethamine, N-methylglucamine, and the like, or with an inorganic base such as aluminum hydroxide, calcium hydroxide, potassium hydroxide, sodium carbonate, sodium hydroxide, and the like.

Reference to a pharmaceutically acceptable salt includes the solvent addition forms or crystal forms thereof, particularly solvates or polymorphs. Solvates contain either stoichiometric or non-stoichiometric amounts of a solvent, and are optionally formed during the process of crystallization with pharmaceutically acceptable solvents such as water, ethanol, and the like. Hydrates are formed when the solvent is water, and alcoholates are formed when the solvent is alcohol. Solvates of compounds of Formula (I) are conveniently prepared or formed during the processes described herein. By way of example only, hydrates of compounds of Formula (I) are conveniently prepared by recrystallization from an aqueous/organic solvent mixture, using organic solvents including, but not limited to, dioxane, tetrahydrofuran, ethanol, or methanol. In addition, the compounds provided herein can exist in unsolvated as well as solvated forms. In general, the solvated forms are considered equivalent to the unsolvated forms for the purposes of the compounds and methods provided herein.

In some embodiments, compounds of Formula (I) are prepared as prodrugs. A "prodrug" refers to an agent that is converted into the parent drug in vivo.

In yet another embodiment, the compounds of Formula (I) possess one or more stereocenters and each center exists independently in either the R or S configuration. The compounds presented herein include all diastereomeric, enantiomeric, and epimeric forms as well as the appropriate mixtures thereof. Stereoisomers are obtained, if desired, by methods such as, the separation of stereoisomers by chiral chromatographic columns or stereoselective synthesis.

The methods and formulations described herein include the use of N-oxides (if appropriate), crystalline forms (also known as polymorphs), or pharmaceutically acceptable salts of compounds having the structure of Formula (I), as well as active metabolites of these compounds having the same type of activity. In some situations, compounds exist as tautomers.

In some embodiments, the compounds described herein exist as tautomers. All tautomers are intended to be within the scope of the molecular formulas described herein.

Definitions

Unless otherwise stated, the following terms used in this application, including the specification and claims, have the definitions given below. It must be noted that, as used in the specification and the appended claims, the singular forms "a," "an" and "the" include plural referents unless the context clearly dictates otherwise. In this application, the use of "or" or "and" means "and/or" unless stated otherwise. Furthermore, use of the term "including" as well as other forms, such as "include", "includes," and "included," is not limiting.

"Alkoxy" refers to (alkyl)O—, where alkyl is as defined herein.

"Alkyl" refers to an aliphatic hydrocarbon group. The alkyl may be saturated or unsaturated. In one aspect, alkyl groups are selected from methyl, ethyl, propyl, iso-propyl, n-butyl, iso-butyl, sec-butyl, and t-butyl.

"Cycloalkyl" refers to a monocyclic aliphatic, non-aromatic radical, wherein each of the atoms forming the ring (i.e. skeletal atoms) is a carbon atom. In some embodiments, cycloalkyl groups are selected from among cyclopropyl, cyclobutyl, cyclopentyl, and cyclohexyl.

"Halo", "halogen" or "halide" means fluoro, chloro, bromo or iodo.

"Fluoroalkyl" refers to an alkyl in which one or more hydrogen atoms are replaced by a fluorine atom. In one aspect, a fluoroalkyl is selected from —$CF_3$, —$CHF_2$, —$CH_2F$, —$CH_2CF_3$ and —$CF_2CF_3$.

"Fluoroalkoxy" refers to (fluoroalkyl)O—, where fluoroalkyl is as defined herein.

"Heteroalkyl" refers to an alkyl group in which one or more skeletal atoms of the alkyl are selected from an atom other than carbon, e.g., oxygen, nitrogen, sulfur, phosphorus or combinations thereof. In one aspect, heteroalkyl refers to an alkyl group in which one of the skeletal atoms of the alkyl is oxygen, nitrogen, or sulfur. In another aspect, heteroalkyl refers to an alkyl group in which one of the skeletal atoms of the alkyl is oxygen.

The term "optionally substituted" or "substituted" means that the referenced group may be substituted with one or more additional group(s) individually and independently selected from halogen, —OH, —CN, $C_1$-$C_4$alkyl, $C_1$-$C_4$fluoroalkyl, $C_1$-$C_4$alkoxy, $C_1$-$C_4$fluoroalkoxy, and $C_1$-$C_4$heteroalkyl.

A "metabolite" of a compound disclosed herein is a derivative of that compound that is formed when the compound is metabolized. The term "active metabolite" refers to a biologically active derivative of a compound that is formed when the compound is metabolized.

"$PGD_2$-dependent" refers to conditions or disorders that would not occur, or would not occur to the same extent, in the absence of $PGD_2$. "$PGD_2$-mediated" refers to refers to conditions or disorders that might occur in the absence of $PGD_2$ but can occur in the presence of $PGD_2$.

"Effective amount" or "therapeutically effective amount," as used herein, refer to a sufficient amount of an agent or a compound being administered which will relieve to some extent one or more of the symptoms of the disease or condition being treated. An appropriate effective amount in any individual case may be determined using techniques, such as a dose escalation study.

The terms "treat," "treating" or "treatment," as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

The term "subject" or "patient" encompasses mammals and non-mammals. In one aspect, the "subject" or "patient" is a mammal. In one embodiment, the mammal is a human.

Pharmaceutical Composition/Formulation

Suitable routes of administration include, but are not limited to, oral, intravenous, rectal, aerosol, parenteral, ophthalmic, pulmonary, transmucosal, transdermal, vaginal, otic, nasal, intramuscular injection, subcutaneous injection, and topical administration. In addition, by way of example only, parenteral delivery includes intramuscular, subcutaneous, intravenous, intramedullary injections, as well as intrathecal, direct intraventricular, intraperitoneal, intralymphatic, and intranasal injections.

In certain embodiments, a compound as described herein is administered in a local rather than systemic manner. In other embodiments, the compound as described herein is provided in the form of a rapid release formulation, in the form of an extended release formulation, or in the form of an intermediate release formulation. In yet other embodiments, the compound described herein is administered topically.

In some embodiments, the compounds described herein are formulated into pharmaceutical compositions. In specific embodiments, pharmaceutical compositions are formulated in a conventional manner using one or more physiologically acceptable carriers comprising excipients and auxiliaries which facilitate processing of the active compounds into preparations which can be used pharmaceutically. Proper formulation is dependent upon the route of administration chosen. Any pharmaceutically acceptable techniques, carriers, and excipients are used as suitable to formulate the pharmaceutical compositions described herein: *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms* and Drug Delivery Systems, Seventh Ed. (Lippincott Williams & Wilkins 1999).

A pharmaceutical composition refers to a mixture of a compound of Formula (I) with other chemical components, such as carriers, stabilizers, diluents, dispersing agents, suspending agents, thickening agents, and/or excipients. In certain embodiments, the pharmaceutical composition facilitates administration of the compound to a mammal.

In one embodiment, compounds of Formula (I) are formulated in an aqueous solution. In specific embodiments, the aqueous solution is selected from, by way of example only, a physiologically compatible buffer, such as Hank's solution, Ringer's solution, or physiological saline buffer. In other embodiments, compounds of Formula (I) are formulated for transmucosal administration. In specific embodiments, transmucosal formulations include penetrants that are appropriate to the barrier to be permeated. In still other embodiments wherein the compounds described herein are formulated for other parenteral injections, appropriate formulations include aqueous or nonaqueous solutions.

In another embodiment, compounds described herein are formulated for oral administration. The compounds described herein are formulated in oral dosage forms that include, by way of example only, tablets, powders, pills, dragees, capsules, liquids, gels, syrups, elixirs, slurries, suspensions and the like.

In certain embodiments, pharmaceutical preparations for oral use are obtained by mixing one or more solid excipient with one or more of the compounds described herein, optionally grinding the resulting mixture, and processing the mixture of granules, after adding suitable auxiliaries, if desired, to obtain tablets or pills. Suitable excipients are, in particular, fillers such as sugars, including lactose, sucrose, mannitol, or sorbitol; cellulose preparations such as: for example, maize starch, wheat starch, rice starch, potato starch, gelatin, gum tragacanth, methylcellulose, microcrystalline cellulose, hydroxypropylmethylcellulose, sodium carboxymethylcellulose; or others such as: polyvinylpyrrolidone (PVP or povidone) or calcium phosphate. In specific embodiments, disintegrating agents are optionally added. Disintegrating agents include, by way of example only, cross-linked croscarmellose sodium, polyvinylpyrrolidone, agar, or alginic acid or a salt thereof such as sodium alginate.

Oral dosage forms also include push-fit capsules made of gelatin, as well as soft, sealed capsules made of gelatin and a plasticizer, such as glycerol or sorbitol. In specific embodiments, push-fit capsules contain the active ingredients in admixture with one or more filler. Fillers include, by way of example only, lactose, binders such as starches, and/or lubricants such as talc or magnesium stearate and, optionally, stabilizers. In other embodiments, soft capsules contain one or more active compound that is dissolved or suspended in a suitable liquid. Suitable liquids include, by way of example only, one or more fatty oil, liquid paraffin, or liquid polyethylene glycol. In addition, stabilizers are optionally added.

In still other embodiments, the compounds of Formula (I) are administered topically. Topically administrable compositions include solutions, suspensions, lotions, gels, pastes, medicated sticks, balms, creams or ointments.

In other embodiments, the compounds of Formula (I) are formulated for administration by inhalation. Various forms suitable for administration by inhalation include, but are not limited to, aerosols, mists or powders.

The active ingredient in the pharmaceutical compositions is in free-acid or free-base form, or in a pharmaceutically acceptable salt form. In addition, the methods and pharmaceutical compositions described herein include the use of N-oxides, crystalline forms (also known as polymorphs), as well as active metabolites of these compounds having the same type of activity. All tautomers of the compounds described herein are included within the scope of the compounds presented herein. Additionally, the compounds described herein encompass unsolvated as well as solvated forms with pharmaceutically acceptable solvents such as water, ethanol, and the like. The solvated forms of the compounds presented herein are also considered to be disclosed herein. In addition, the pharmaceutical compositions optionally include other medicinal or pharmaceutical agents, carriers, adjuvants, such as preserving, stabilizing, wetting or emulsifying agents, solution promoters, salts for regulating the osmotic pressure, buffers, and/or other therapeutically valuable substances.

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation clinical trial.

In prophylactic applications, compositions comprising the compounds described herein are administered to a patient susceptible to or otherwise at risk of a particular disease, disorder or condition. In this use, the precise amounts also depend on the patient's state of health, weight, and the like.

The amount of a given agent that corresponds to such an amount varies depending upon factors such as the particular compound, disease or condition and its severity, the identity (e.g., weight) of the mammal in need of treatment, but can nevertheless be determined according to the particular circumstances surrounding the case, including, e.g., the specific agent being administered, the route of administration, the condition being treated, and the mammal being treated. Doses employed for adult human treatment are typically in the range of 0.02-5000 mg per day, 1-1500 mg per day, 1-500 mg per day or 1-100 mg per day. In one embodiment, the dose is presented in a single dose or in divided doses administered at appropriate intervals, for example as two, three, four or more sub-doses per day.

In one embodiment, the daily dosages appropriate for the compound of Formula (I) are from about 0.01 to about 10 mg/kg per body weight. hi certain embodiments, suitable unit dosage forms for oral administration comprise from about 1 to 500 mg active ingredient. In other embodiments, the daily dosage or the amount of active in the dosage form are lower or higher than the ranges indicated herein.

In one aspect, compounds of Formula (I) are used in the treatment of $PGD_2$-dependent or $PGD_2$-mediated diseases, disorders or conditions as disclosed herein. In one aspect, compounds of Formula (I) are $DP_2$ antagonists. In one aspect, the compounds of Formula (I) exhibit negligible modulatory activty on CETP and/or PPAR receptors. CETP assays are known (Epps et al. *Chem. Phys. Lipids*. 77, 51-63, 1995). PPAR assays are known (Example 48 of US 2006/0058301).

In certain instances, it is appropriate to administer at least one compound of Formula (I) in combination with another therapeutic agent. In combination therapies, the multiple therapeutic agents (one of which is one of the compounds described herein) are administered in any order or even simultaneously. If administration is simultaneous, the multiple therapeutic agents are, by way of example only, provided in a single, unified form, or in multiple forms (e.g., as a single pill or as two separate pills).

EXAMPLES

These examples are provided for illustrative purposes only and not to limit the scope of the claims provided herein.

Example 1

Synthesis of {2'-[(Acetyl-methyl-amino)-methyl]-6-methoxy-4'-trifluoromethyl-biphenyl-3-yl}-acetic acid (Compound 1-1)

Step 1: (3-Bromo-4-methoxy-phenyl)-acetic acid methyl ester

To (3-bromo-4-methoxy-phenyl)-acetic acid (5.226 g, 21.32 mmol) in MeOH (52 mL) was added thionyl chloride (3.1 mL, 42.65 mmol), and the reaction was stirred at room temperature for 2 hours. Once no starting material was seen by analytical LCMS, the mixture was concentrated and then diluted with $CH_2Cl_2$ and aqueous 1N NaOH. The aqueous layer was separated and extracted with $CH_2Cl_2$, and the combined organic layers were washed with $H_2O$, dried over $MgSO_4$, filtered, and concentrated to give the title compound.

Step 2: [4-Methoxy-3-(4,4,5,5-tetramethyl-[1,3,2]dioxaborolan-2-yl)-phenyl]-acetic acid methyl ester (3-Bromo-4-methoxy-phenyl)-acetic acid methyl ester (5.1 g, 19.68 mmol), bis(pinacolato)diboron (6.54 g, 25.59 mmol), and potassium acetate (5.80 g, 59.05 mmol) were combined in DMF (100 mL) under $N_2$. The solution was purged with $N_2$, and then (1,1'-bis(diphenylphosphino)ferrocene)-dichloropalladium(II) (0.805 g, 0.98 mmol) was added and the reaction was heated to 85° C. overnight. Starting material was still observed after 16 hours, so additional (1,1'-bis(diphenylphosphino)ferrocene)-dichloropalladium (II) (0.808 g, 0.98 mmol) was added, and the reaction was stirred at 85° C. overnight. Once no starting material was seen by analytical LCMS, the mixture was cooled to room temperature and concentrated. The residue was partitioned between EtOAc and $H_2O$ and filtered through Celite. The aqueous layer was separated and extracted with EtOAc, and the combined organic layers were washed with brine, dried over $MgSO_4$, filtered, and concentrated. The residue was purified by silica gel chromatography (0-100% EtOAc in hexanes) to give the title compound.

Step 3: 2-Bromo-5-trifluoromethyl-benzaldehyde

To (2-bromo-5-trifluoromethyl-phenyl)-methanol (2.216 g, 8.69 mmol) and N-methylmorpholine N-oxide (2.051 g, 17.38 mmol) in $CH_2Cl_2$ (44 mL) and MeCN (2.2 mL) was added tetrapropylammonium perruthenate (0.311 g, 0.87 mmol), and the reaction was stirred at room temperature for 20 minutes. Once no starting material was seen by analytical tlc, the mixture was concentrated and purified by silica gel chromatography to give the title compound.

Step 4: (2'-Formyl-6-methoxy-4'-trifluoromethyl-biphenyl-3-yl)-acetic acid methyl ester 2-Bromo-5-trifluoromethyl-benzaldehyde (4.152 g, 16.41 mmol), [4-methoxy-3-(4,4,5,5-tetramethyl-[1,3,2]dioxaborolan-2-yl)-phenyl]-acetic acid methyl ester (4.988 g, 16.41 mmol), and potassium carbonate (5.67 g, 41.03 mmol) were combined in DME (40 mL) and $H_2O$ (20 mL) under $N_2$. The mixture was purged with $N_2$, and then tetrakis(triphenylphosphine)palladium(0) (1.9 g, 1.64 mmol) was added, and the reaction was heated to 90° C. for 10 hours. Once no starting material was seen by analytical LCMS, the mixture was cooled to room temperature and diluted with $CH_2Cl_2$ and $H_2O$. The aqueous layer was separated and extracted with $CH_2Cl_2$, and the combined organic layers were dried over $MgSO_4$, filtered, and concentrated. The residue was purified by silica gel chromatography (0-100% EtOAc in hexanes) to give the title compound.

Step 5: (6-Methoxy-2'-methylaminomethyl-4'-trifluoromethyl-biphenyl-3-yl)-acetic acid methyl ester To (2'-formyl-6-methoxy-4'-trifluoromethyl-biphenyl-3-yl)-acetic acid methyl ester (0.228 g, 0.65 mmol) and methylamine (2M in THF; 0.5 mL, 0.84 mmol) in $CH_2Cl_2$ (3.4 mL) was added sodium cyanoborohydride (0.061 g, 0.97 mmol), followed by acetic acid (1 drop). The reaction was stirred at room temperature overnight, until no starting material was seen by analytical LCMS. The solution was neutralized with saturated aqueous $NaHCO_3$ and extracted with $CH_2Cl_2$, and the combined organic layers were dried over $MgSO_4$, filtered, and concentrated to give the title compound.

Step 6: {2'-[(Acetyl-methyl-amino)-methyl]-6-methoxy-4'-trifluoromethyl-biphenyl-3-yl}-acetic acid methyl ester To (6-methoxy-2'-methylaminomethyl-4'-trifluoromethyl-biphenyl-3-yl)-acetic acid methyl ester (0.114 g, 0.31 mmol) and triethylamine (0.05 mL, 0.34 mmol) in $CH_2Cl_2$ (1.2 mL) was added acetyl chloride (0.02 mL, 0.34 mmol), and the reaction was stirred at room temperature for 1 hour. Once no starting material was seen by analytical LCMS, the mixture was diluted with $CH_2Cl_2$ and $H_2O$, and the aqueous layer was extracted with $CH_2Cl_2$. The combined organic layers were dried over $MgSO_4$, filtered, and concentrated, and the residue was purified by silica gel chromatography (0-100% EtOAc in hexanes) to give the title compound.

Step 7: {2'-[(Acetyl-methyl-amino)-methyl]-6-methoxy-4'-trifluoromethyl-biphenyl-3-yl}-acetic acid {2'-[(Acetyl-methyl-amino)-methyl]-6-methoxy-4'-trifluoromethyl-biphenyl-3-yl}-acetic acid methyl ester (0.038 g, 0.09 mmol) was dissolved in THF (0.38 mL), MeOH (0.3 mL), and aqueous 1N NaOH (0.2 mL), and the mixture was stirred at room temperature for 1 hour. Once no starting material was seen by analytical LCMS, the mixture was diluted with $CH_2Cl_2$ and $H_2O$, and the aqueous layer was extracted with $CH_2Cl_2$. The combined organic layers were dried over $MgSO_4$, filtered, and concentrated, and the residue was purified by preparative HPLC. The desired fractions were combined, concentrated, and the isolated material was diluted with $CH_2Cl_2$ and neutralized with saturated aqueous $NaHCO_3$. The organic layer was separated, dried over $MgSO_4$, filtered, and concentrated to give the title compound. The aqueous layer was acidified and extracted with EtOAc, and the organic layer was concentrated to give additional product.

{2'-[(Acetyl-cyclopropyl-amino)-methyl]-6-methoxy-4'-trifluoromethyl-biphenyl-3-yl}-acetic acid (Compound 1-12) was prepared following the procedures of Example 1 and using (2'-formyl-6-methoxy-4'-trifluoromethyl-biphenyl-3-yl)-acetic acid methyl ester, cyclopropylamine, and acetyl chloride.

{2'-[(Acetyl-cyclobutyl-amino)-methyl]-6-methoxy-4'-trifluoromethyl-biphenyl-3-yl}-acetic acid (Compound 1-30) was prepared according to the procedures outlined in Example 1 by using the following materials: (2'-formyl-6-methoxy-4'-trifluoromethyl-biphenyl-3-yl)-acetic acid methyl ester, cyclobutylamine and acetyl chloride.

{2'-[(Acetyl-cyclopentyl-amino)-methyl]-6-methoxy-4'-trifluoromethyl-biphenyl-3-yl}-acetic acid (Compound 1-31) was prepared according to the procedures outlined in Example 1 by using the following materials: (2'-formyl-6-methoxy-4'-trifluoromethyl-biphenyl-3-yl)-acetic acid methyl ester, cyclopentylamine and acetyl chloride.

{4'-Bromo-2'-[(cyclopropanecarbonyl-ethyl-amino)-methyl]-6-methoxy-biphenyl-3-yl}-acetic acid (Compound 1-247) was prepared by following the procedures of Example 1 using the following materials: (5-bromo-2-iodo-benzyl)-ethyl-amine, cyclopropanecarbonyl chloride, and [4-methoxy-3-(4,4,5,5-tetramethyl-[1,3,2]dioxaborolan-2-yl)-phenyl]-acetic acid ethyl ester.

{2'-[(Benzyloxycarbonyl-cyclobutyl-amino)-methyl]-6-methoxy-4'-trifluoromethyl-biphenyl-3-yl}-acetic acid (Compound 1-34) was prepared by following the procedures of Example 1 and using the following starting materials: (2'-formyl-6-methoxy-4'-trifluoromethyl-biphenyl-3-yl)-acetic acid methyl ester, cyclobutylamine, and benzyl chloroformate.

{2'-[(Benzyloxycarbonyl-cyclopentyl-amino)-methyl]-6-methoxy-4'-trifluoromethyl-biphenyl-3-yl}-acetic acid (Compound 1-35) was prepared by following the procedures of Example 1 and using the following starting materials: (2'-formyl-6-methoxy-4'-trifluoromethyl-biphenyl-3-yl)-acetic acid methyl ester, cyclopentylamine, and benzyl chloroformate.

{2'-[(Benzyloxycarbonyl-cyclopropyl-amino)-methyl]-6-methoxy-4'-trifluoromethyl-biphenyl-3-yl}-acetic acid (Compound 1-36) was prepared by following the procedures of Example 1 and using the following starting materials: (2'-formyl-6-methoxy-4'-trifluoromethyl-biphenyl-3-yl)-acetic acid methyl ester, cyclopropylamine, and benzyl chloroformate Example 2

Synthesis of {2'-[(Acetyl-ethyl-amino)-methyl]-6-methoxy-4'-trifluoromethyl-biphenyl-3-yl}-acetic acid (Compound 1-2)

Step 1: (2'-Ethylaminomethyl-6-methoxy-4'-trifluoromethyl-biphenyl-3-yl)-acetic acid methyl ester
Prepared according to the procedure described in Example 1, Step 5, using the following starting materials: (2'-formyl-6-methoxy-4'-trifluoromethyl-biphenyl-3-yl)-acetic acid methyl ester and ethylamine (2M in THF).
Step 2: {2'-[(Acetyl-ethyl-amino)-methyl]-6-methoxy-4'-trifluoromethyl-biphenyl-3-yl}-acetic acid methyl ester
Prepared according to the procedure described in Example 1, Step 6, using the following starting materials : (2'-ethylaminomethyl-6-methoxy-4'-trifluoromethyl-biphenyl-3-yl)-acetic acid methyl ester and acetyl chloride.
Step 3: {2'-[(Acetyl-ethyl-amino)-methyl]-6-methoxy-4'-trifluoromethyl-biphenyl-3-yl}-acetic acid
Prepared according to the procedure described in Example 1, Step 7, using the following starting material: {2'-[(acetyl-ethyl-amino)-methyl]-6-methoxy-4'-trifluoromethyl-biphenyl-3-yl}-acetic acid methyl ester.

{2'-[(Cyclopropanecarbonyl-ethyl-amino)-methyl]-6-methoxy-4'-trifluoromethyl-biphenyl-3-yl}-acetic acid (Compound 1-33) was prepared by following the procedures of Example 1 and using (2'-ethylaminomethyl-6-methoxy-4'-trifluoromethyl-biphenyl-3-yl)-acetic acid methyl ester and cyclopropanecarbonyl chloride.

(2'-{[Ethyl-(2-phenoxy-propionyl)-amino]-methyl}-6-methoxy-4'-trifluoromethyl-biphenyl-3-yl)-acetic acid (Compound 1-45) was prepared by following the procedures outlined in Example 1 and using (2'-ethylaminomethyl-6-methoxy-4'-trifluoromethyl-biphenyl-3-yl)-acetic acid methyl ester and 2-phenoxypropionyl chloride.

(2'-{[Ethyl-(2-phenoxy-acetyl)-amino]-methyl}-6-methoxy-4'-trifluoromethyl-biphenyl-3-yl)-acetic acid (Compound 1-48) was prepared by following the procedures outlined in Example 1 and using (2'-ethylaminomethyl-6-methoxy-4'-trifluoromethyl-biphenyl-3-yl)-acetic acid methyl ester and phenoxyacetyl chloride.

(2'-{[(2-Benzyloxy-acetyl)-ethyl-amino]-methyl}-6-methoxy-4'-trifluoromethyl-biphenyl-3-yl)-acetic acid (Compound 1-92) was prepared by following the procedures outlined in Example 1 and using (2'-ethylaminomethyl-6-methoxy-4'-trifluoromethyl-biphenyl-3-yl)-acetic acid methyl ester and benzyloxyacetyl chloride.

[2'-({[2-(4-Chloro-phenoxy)-acetyl]-ethyl-amino}-methyl)-6-methoxy-4'-trifluoromethyl-biphenyl-3-yl]-acetic acid (Compound 1-93) was prepared by following the procedures outlined in Example 1 and using (2'-ethylaminomethyl-6-methoxy-4'-trifluoromethyl-biphenyl-3-yl)-acetic acid methyl ester and 4-chlorophenoxyacetyl chloride.

{2'-[(Cyclobutanecarbonyl-ethyl-amino)-methyl]-6-methoxy-4'-trifluoromethyl-biphenyl-3-yl}-acetic acid (Compound 1-206) was prepared using the procedures of Example 1 and using (2'-ethylaminomethyl-6-methoxy-4'-trifluoromethyl-biphenyl-3-yl)-acetic acid ethyl ester and cyclobutanecarbonyl chloride.

(2'-{[(2,2-Dimethyl-propionyl)-ethyl-amino]-methyl}-6-methoxy-4'-trifluoromethyl-biphenyl-3-yl)-acetic acid (Compound 1-245) was prepared using the procedures of Example 1 and using (2'-ethylaminomethyl-6-methoxy-4'-trifluoromethyl-biphenyl-3-yl)-acetic acid ethyl ester and trimethylacetyl chloride.

{2'-[(Ethyl-isobutyryl-amino)-methyl]-6-methoxy-4'-trifluoromethyl-biphenyl-3-yl}-acetic acid (Compound 1-246) was prepared using the procedures of Example 1 and using (2'-ethylaminomethyl-6-methoxy-4'-trifluoromethyl-biphenyl-3-yl)-acetic acid ethyl ester and isobutyryl chloride.

Example 3

Synthesis of (2'-{[Acetyl-(2,2-dimethyl-propyl)-amino]-methyl}-6-methoxy-4'-trifluoromethyl-biphenyl-3-yl)-acetic acid (Compound 1-3)

Step 1: {2'-[(2,2-Dimethyl-propylamino)-methyl]-6-methoxy-4'-trifluoromethyl-biphenyl-3-yl}-acetic acid methyl ester
Prepared according to the procedure described in Example 1, Step 5, using the following starting materials: (2'-formyl-6-methoxy-4'-trifluoromethyl-biphenyl-3-yl)-acetic acid methyl ester and neopentylamine.
Step 2: (2'-{[Acetyl-(2,2-dimethyl-propyl)-amino]-methyl}-6-methoxy-4'-trifluoromethyl-biphenyl-3-yl)-acetic acid methyl ester
Prepared according to the procedure described in Example 1, Step 6, using the following starting materials: {2'-[(2,2-dimethyl-propylamino)-methyl]-6-methoxy-4'-trifluoromethyl-biphenyl-3-yl}-acetic acid methyl ester and acetyl chloride.
Step 3: (2'-{[Acetyl-(2,2-dimethyl-propyl)-amino]-methyl}-6-methoxy-4'-trifluoromethyl-biphenyl-3-yl)-acetic acid
(2'-{[Acetyl-(2,2-dimethyl-propyl)-amino]-methyl}-6-methoxy-4'-trifluoromethyl-biphenyl-3-yl)-acetic acid methyl ester (0.152 g, 0.33 mmol) was dissolved in THF (1.5 mL), MeOH (1.2 mL), and aqueous 1N NaOH (0.72 mL), and the mixture was stirred at room temperature for 4 hours. Once no starting material was seen by analytical LCMS, the mixture was diluted with $CH_2Cl_2$ and aqueous 1N HCl, and the aqueous layer was extracted with $CH_2Cl_2$. The combined organic layers were dried over $MgSO_4$, filtered, and concentrated to give the title compound.

Example 4

Synthesis of (2'-{[Acetyl-(2,2,2-trifluoro-ethyl)-amino]-methyl}-6-methoxy-4'-trifluoromethyl-biphenyl-3-yl)-acetic acid (Compound 1-4)

Step 1: {6-Methoxy-2'-[(2,2,2-trifluoro-ethylamino)-methyl]-4'-trifluoromethyl-biphenyl-3-yl}-acetic acid methyl ester 2,2,2-Trifluoroethylamine hydrochloride (0.101 g, 0.71 mmol) was treated with sodium acetate (0.061 g, 0.71 mmol) in MeOH (1 mL) with heating and sonication. (2'-Formyl-6-methoxy-4'-trifluoromethyl-biphenyl-3-yl)-acetic acid methyl ester (0.207 g, 0.59 mmol) in MeOH (2 mL) was added, followed by sodium cyanoborohydride (0.069 g, 1.06 mmol), and the reaction was stirred at room temperature for 1 hour. Once no starting material was seen by analytical LCMS, the mixture was quenched with $H_2O$ and extracted twice with $CH_2Cl_2$. The combined organic layers were dried over $MgSO_4$, filtered, and concentrated to give the title compound.

Step 2: (2'-{[Acetyl-(2,2,2-trifluoro-ethyl)-amino]-methyl}-6-methoxy-4'-trifluoromethyl-biphenyl-3-yl)-acetic acid Prepared according to the procedure described in Example 1, Step 6 and Step 7, using the following starting materials: {6-methoxy-2'-[(2,2,2-trifluoro-ethylamino)-methyl]-4'-trifluoromethyl-biphenyl-3-yl}-acetic acid methyl ester and acetyl chloride.

Example 5

Synthesis of {2'-[(Acetyl-ethyl-amino)-methyl]-6-fluoro-4'-trifluoromethyl-biphenyl-3-yl}-acetic acid (Compound 1-10)

Step 1: (3-Bromo-4-fluoro-phenyl)-acetic acid methyl ester

Prepared according to the procedure described in Example 1, Step 1, using the following starting material: (3-bromo-4-fluoro-phenyl)-acetic acid.

Step 2: [4-Fluoro-3-(4,4,5,5-tetramethyl-[1,3,2]fioxaborolan-2-yl)-phenyl]-acetic acid methyl ester Prepared according to the procedure described in Example 1, Step 2, using the following starting materials: (3-bromo-4-fluoro-phenyl)-acetic acid methyl ester and bis(pinacolato)diboron.

Step 3: (6-Fluoro-2'-formyl-4'-trifluoromethyl-biphenyl-3-yl)-acetic acid methyl ester Prepared according to the procedure described in Example 1, Step 4, using the following starting materials: 2-bromo-5-trifluoromethyl-benzaldehyde and [4-fluoro-3-(4,4,5,5-tetramethyl-[1,3,2]dioxaborolan-2-yl)-phenyl]-acetic acid methyl ester; the isolated product was further purified by preparative HPLC.

Step 4: (2'-Ethylaminomethyl-6-fluoro-4'-trifluoromethyl-biphenyl-3-yl)-acetic acid methyl ester Prepared according to the procedure described in Example 1, Step 5, using the following starting materials: (6-fluoro-2'-formyl-4'-trifluoromethyl-biphenyl-3-yl)-acetic acid methyl ester and ethylamine (2M in THF).

Step 5: {2'-[(Acetyl-ethyl-amino)-methyl]-6-fluoro-4'-trifluoromethyl-biphenyl-3-yl}-acetic acid methyl ester Prepared according to the procedure described in Example 1, Step 6, using the following starting materials: (2'-ethylaminomethyl-6-fluoro-4'-trifluoromethyl-biphenyl-3-yl)-acetic acid methyl ester and acetyl chloride.

Step 6: {2'-[(Acetyl-ethyl-amino)-methyl]-6-fluoro-4'-trifluoromethyl-biphenyl-3-yl}-acetic acid The methyl ester in the product of Step 5 was hydrolyzed according to the procedure described in Example 3, Step 3.

Example 6

Synthesis of (2'-{[Acetyl-(2,2,2-trifluoro-ethyl)-amino]-methyl}-6-fluoro-4'-trifluoromethyl-biphenyl-3-yl)-acetic acid (Compound 1-11)

Step 1: {6-Fluoro-2'-[(2,2,2-trifluoro-ethylamino)-methyl]-4'-trifluoromethyl-biphenyl-3-yl}-acetic acid methyl ester Prepared according to the procedure described in Example 4, Step 1, using the following starting materials: (6-fluoro-2'-formyl-4'-trifluoromethyl-biphenyl-3-yl)-acetic acid methyl ester and 2,2,2-trifluoroethylamine hydrochloride.

Step 2: (2'-{[Acetyl-(2,2,2-trifluoro-ethyl)-amino]-methyl}-6-fluoro-4'-trifluoromethyl-biphenyl-3-yl)-acetic acid Prepared according to the procedure described in Example 1, Step 6 and Step 7, using the following starting materials: {6-fluoro-2'-[(2,2,2-trifluoro-ethylamino)-methyl]-4'-trifluoromethyl-biphenyl-3-yl}-acetic acid methyl ester and acetyl chloride.

Example 7

Synthesis of {2'-[(Ethyl-methoxycarbonyl-amino)-methyl]-6-methoxy-4'-trifluoromethyl-biphenyl-3-yl}-acetic acid (Compound 1-23)

Step 1: {2'-[(Ethyl-methoxycarbonyl-mmino)-methyl]-6-methoxy-4'-trifluoromethyl-biphenyl-3-yl}-acetic acid methyl ester To (2'-ethylaminomethyl-6-methoxy-4'-trifluoromethyl-biphenyl-3-yl)-acetic acid methyl ester (0.091 g, 0.24 mmol) and triethylamine (0.05 mL, 0.36 mmol) in $CH_2Cl_2$ (1 mL) was added methyl chloroformate (0.03 mL, 0.36 mmol), and the mixture was stirred at room temperature for 20 minutes. Once no starting material was seen by analytical LCMS, the reaction was quenched with $H_2O$ and diluted with $CH_2Cl_2$ and saturated aqueous $NaHCO_3$. The aqueous layer was separated and extracted with $CH_2Cl_2$, and the combined organic layers were dried over $MgSO_4$, filtered, and concentrated, and the residue was purified by silica gel chromatography (0-100% EtOAc in hexanes) to give the title compound.

Step 2: {2'-[(Ethyl-methoxycarbonyl-amino)-methyl]-6-methoxy-4'-trifluoromethyl-biphenyl-3-yl}-acetic acid Prepared according to the procedure described in Example 3, Step 3, using the following starting material: {2'-[(ethyl-methoxycarbonyl-amino)-methyl]-6-methoxy-4'-trifluoromethyl-biphenyl-3-yl}-acetic acid methyl ester.

{2'-[(Benzyloxycarbonyl-methyl-amino)-methyl]-6-methoxy-4'-trifluoromethyl-biphenyl-3-yl}-acetic acid (Compound 1-27) was prepared by following the procedures of Example 7 and using (6-methoxy-2'-methylaminomethyl-4'-trifluoromethyl-biphenyl-3-yl)-acetic acid methyl ester and benzyl chloroformate.

{2'-[(Benzyloxycarbonyl-ethyl-amino)-methyl]-6-methoxy-4'-trifluoromethyl-biphenyl-3-yl}-acetic acid (Compound 1-28) was prepared by following the procedures of Example 7 and using (2'-ethylaminomethyl-6-methoxy-4'-trifluoromethyl-biphenyl-3-yl)-acetic acid methyl ester and benzyl chloroformate.

Example 8

Synthesis of {2'-[(Benzyloxycarbonyl-methyl-amino)-methyl]-6-fluoro-4'-trifluoromethyl-biphenyl-3-yl}-acetic acid (Compound 1-29)

Step 1: (6-Fluoro-2'-methylaminomethyl-4'-trifluoromethyl-biphenyl-3-yl)-acetic acid methyl ester Prepared according to the procedure described in Example 1, Step 5, using the following starting materials: (6-fluoro-2'-formyl-4'-trifluoromethyl-biphenyl-3-yl)-acetic acid methyl ester and methylamine (2M in THF).

Step 2: {2'-[(Benzyloxycarbonyl-methyl-amino)-methyl]-6-fluoro-4'-trifluoromethyl-biphenyl-3-yl}-acetic acid methyl ester Prepared according to the procedure described in Example 7, Step 1, using the following starting materials: (6-fluoro-2'-methylaminomethyl-4'-trifluoromethyl-biphenyl-3-yl)-acetic acid methyl ester and benzyl chloroformate.

Step 3: {2'-[(Benzyloxycarbonyl-methyl-amino)-methyl]-6-fluoro-4'-trifluoromethyl-biphenyl-3-yl}-acetic acid The methyl ester of the product from Step 2 was hydrolyzed according to the procedure described in Example 1 Step 7.

Example 9

Synthesis of (2'-{[Ethyl-(2-methoxy-acetyl)-amino]-methyl}-6-methoxy-4'-trifluoromethyl-biphenyl-3-yl)-acetic acid (Compound 1-46)

Step 1: (2'-{[Ethyl-(2-methoxy-acetyl)-amino]-methyl}-6-methoxy-4'-trifluoromethyl-biphenyl-3-yl)-aAcetic acid methyl ester Prepared according to the procedure described in Example 1, Step 6, using the following starting materials: (2'-ethylaminomethyl-6-methoxy-4'-trifluoromethyl-biphenyl-3-yl)-acetic acid methyl ester and methoxyacetyl chloride.

Step 2: (2'-{[Ethyl-(2-methoxy-acetyl)-amino]-methyl}-6-methoxy-4'-trifluoromethyl-biphenyl-3-yl)-acetic acid (2'-{[Ethyl-(2-methoxy-acetyl)-amino]-methyl}-6-methoxy-4'-trifluoromethyl-biphenyl-3-yl)-acetic acid methyl ester (0.135 g, 0.31 mmol) in THF (2 mL) was treated with 1N aqueous LiOH (2 mL) for 2 hours at room temperature. The mixture was acidified with 1N aqueous HCl and extracted three times with EtOAc. The combined organic layers were dried and concentrated, and the residue was purified by preparative HPLC to give the title compound.

Example 10

Synthesis of [2'-(3-Benzyl-1-ethyl-ureidomethyl)-6-methoxy-4'-trifluoromethyl-biphenyl-3-yl]-acetic acid (Compound 1-96)

Step 1: [2'-(3-Benzyl-1-ethyl-ureidomethyl)-6-methoxy-4'-trifluoromethyl-biphenyl-3-yl]-acetic acid methyl ester To (2'-ethylaminomethyl-6-methoxy-4'-trifluoromethyl-biphenyl-3-yl)-acetic acid methyl ester (0.207 g, 0.54 mmol) in $CH_2Cl_2$ (2 mL) at 0° C. was added diisopropylethylamine (0.21 mL, 1.19 mmol), followed by phosgene (20% in toluene; 0.34 mL, 0.65 mmol), and the reaction was stirred for 2 hours at 0° C. Benzylamine (0.09 mL, 0.81 mmol) was then added, and the reaction was stirred for 15 minutes. Triethylamine (0.1 mL, 0.72 mmol) was added, and the reaction was stirred for 1 hour. Additional benzylamine (0.09 mL, 0.81 mmol) and diisopropylethylamine (0.21 mL, 1.19 mmol) were added, and the reaction was stirred for 3 hours, until no starting material was seen by analytical LCMS. The mixture was partitioned between $H_2O$ and $CH_2C_2$, and the aqueous layer was separated and extracted twice with $CH_2C_2$. The combined organic layers were dried and concentrated, and the residue was purified by silica gel chromatography (20-40% EtOAc in hexanes) to give the title compound.

Step 2: [2'-(3-Benzyl-1-ethyl-ureidomethyl)-6-methoxy-4'-trifluoromethyl-biphenyl-3-yl]-acetic acid Prepared according to the procedure described in Example 9, Step 2, using the following starting material: [2'-(3-benzyl-1-ethyl-ureidomethyl)-6-methoxy-4'-trifluoromethyl-biphenyl-3-yl]-acetic acid methyl ester.

Alternative synthesis: To (2'-ethylaminomethyl-6-methoxy-4'-trifluoromethyl-biphenyl-3-yl)-acetic acid ethyl ester (prepared as described in Example 1, Step 1 but using EtOH in place of MeOH; 44.9 g, 0.114 mol) in $CH_2Cl_2$ (450 mL) at room temperature was added triethylamine (24 mL, 0.17 mol), followed by benzylisocyanate (16.7 mL, 0.136 mol), and the reaction was stirred for 2 hours until no starting material was seen by analytical LCMS. The mixture was partitioned between $H_2O$ and $CH_2Cl_2$, and the aqueous layer was separated and extracted with $CH_2Cl_2$. The combined organic layers were dried ($MgSO_4$) and concentrated, and the residue was purified by silica gel chromatography (0-60% EtOAc in hexanes) to give the [2'-(3-benzyl-1-ethyl-ureidomethyl)-6-methoxy-4'-trifluoromethyl-biphenyl-3-yl]-acetic acid ethyl ester. Hydrolysis of the ethyl ester according to the procedure described in Example 1, Step 7 provided [2'-(3-benzyl-1-ethyl-ureidomethyl)-6-methoxy-4'-trifluoromethyl-biphenyl-3-yl]-acetic acid.

Example 11

Synthesis of (2'-Ethylaminomethyl-6-methoxy-4'-trifluoromethyl-biphenyl-3-yl)-acetic acid ethyl ester Step 1: (3-Bromo-4-methoxy-phenyl)-acetic acid ethyl ester Prepared according to the procedure described in Example 1, Step 1, using the following starting materials: 3-bromo-4-methoxyphenylacetic acid and ethanol.

Step 2: [4-Methoxy-3-(4,4,5,5-tetramethyl-[1,3,2]dioxaborolan-2-yl)-phenyl]-acetic acid ethyl ester (3-Bromo-4-methoxy-phenyl)-acetic acid ethyl ester (27.4 g, 100.3 mmol), bis(pinacolato)diboron (25.47 g, 100.3 mmol), and potassium acetate (24.6 g, 250.8 mmol) were combined in 1,4-dioxane (250 mL) under $N_2$. The solution was purged with $N_2$, and then (1,1'-bis(diphenylphosphino)ferrocene)-dichloropalladium(II) (4.10 g, 5.02 mmol) was added and the reaction was heated to 110° C. overnight. The mixture was filtered through Celite and partitioned between EtOAc and brine. The aqueous layer was separated and extracted twice with EtOAc, and the combined organic layers were dried and concentrated. The residue was purified by silica gel chromatography (20-60% EtOAc in hexanes) to give the title compound.

Step 3: (2'-Formyl-6-methoxy-4'-trifluoromethyl-biphenyl-3-yl)-acetic acid ethyl ester Prepared according to the procedure described in Example 1, Step 4, using the following starting materials: 2-bromo-5-(trifluoromethyl)benzaldehyde and [4-methoxy-3-(4,4,5,5-tetramethyl-[1,3,2]dioxaborolan-2-yl)-phenyl]-acetic acid ethyl ester.

Step 4: (2'-Ethylaminomethyl-6-methoxy-4'-trifluoromethyl-biphenyl-3-yl)-acetic acid ethyl ester To (2'-formyl-6-methoxy-4'-trifluoromethyl-biphenyl-3-yl)-acetic acid ethyl ester (1.0 g, 2.73 mmol) in MeOH (8 mL)

was added ethylamine (2M in THF; 5 mL, 10 mmol), followed by acetic acid (0.23 mL, 4.09 mmol). Sodium cyanoborohydride (0.260 g, 4.14 mmol) was then added, and the reaction was stirred at room temperature and monitored by analytical LCMS. The reaction never reached completion, so the mixture was concentrated and partitioned between EtOAc and saturated aqueous NaHCO$_3$. The aqueous layer was extracted with EtOAc, and the combined organic layers were dried over MgSO$_4$, filtered, and concentrated. The residue was purified by silica gel chromatography (0-6% MeOH in CH$_2$Cl$_2$) to give the title compound.

Example 12

Synthesis of {2'-[(Benzyloxycarbonyl-ethyl-amino)-methyl]-6-hydroxy-4'-trifluoromethyl-biphenyl-3-yl}-acetic acid ethyl ester Step 1: (3-Bromo-4-hydroxy-phenyl)-acetic acid
3-Bromo-4-methoxyphenylacetic acid (1.3 g, 5.6 mmol) was heated in a solution of hydrogen bromide (3 mL) and acetic acid (3 mL) at 100° C. overnight. The mixture was then partitioned between EtOAc and H$_2$O, and the aqueous layer was separated and extracted with EtOAc. The combined organic layers were washed with brine, dried over MgSO$_4$, filtered, and concentrated to give the title compound.
Step 2: (3-Bromo-4-hydroxy-phenyl)-acetic acid ethyl ester
(3-Bromo-4-hydroxy-phenyl)-acetic acid (5.6 mmol) in EtOH (20 mL) was treated with sulfuric acid (1 mL) and stirred at room temperature over the weekend. The mixture was concentrated to give the title compound.
Step 3: (2-Bromo-5-trifluoromethyl-benzyl)-ethyl-amine
Prepared according to the procedure described in Example 11, Step 4, using the following starting materials: 2-bromo-5-(trifluoromethyl)benzaldehyde and ethylamine (2M in THF).
Step 4: (2-Bromo-5-trifluoromethyl-benzyl)-ethyl-carbamic acid benzyl ester
Prepared according to the procedure described in Example 1, Step 6, using the following starting materials: (2-bromo-5-trifluoromethyl-benzyl)-ethyl-amine and benzyl chloroformate.
Step 5: Ethyl-[2-(4,4,5,5-tetramethyl-[1,3,2]dioxaborolan-2-yl)-5-trifluoromethyl-benzyl]-carbamic acid benzyl ester
Prepared according to the procedure described in Example 11, Step 2, using the following starting materials: (2-bromo-5-trifluoromethyl-benzyl)-ethyl-carbamic acid benzyl ester and bis(pinacolato)diboron.
Step 6: {2'-[(Benzyloxycarbonyl-ethyl-amino)-Methyl]-6-hydroxy-4'-trifluoromethyl-biphenyl-3-yl}-acetic acid ethyl ester
Prepared according to the procedure described in Example 1, Step 4, using the following starting materials: (3-bromo-4-hydroxy-phenyl)-acetic acid ethyl ester and ethyl-[2-(4,4,5,5-tetramethyl-[1,3,2]dioxaborolan-2-yl)-5-trifluoromethyl-benzyl]-carbamic acid benzyl ester.

Example 13

Synthesis of {2'-[(Benzyloxycarbonyl-ethyl-amino)-methyl]-4'-methanesulfonylamino-6-methoxy-biphenyl-3-yl}-acetic acid (Compound 1-155)

Step 1: (2-Bromo-5-nitro-phenyl)-methanol
To 2-bromo-5-nitrobenzoic acid (5 g, 20 mmol) at 0° C. was added borane tetrahydrofuran complex (1M in THF; 200 mL, 200 mmol), and the reaction was stirred at room temperature overnight. The mixture was quenched with 1N aqueous HCl to give the title compound.
Step 2: 2-Bromo-5-nitro-benzaldehyde
Prepared according to the procedure described in Example 1, Step 3, using the following starting material: (2-bromo-5-nitro-phenyl)-methanol.
Step 3: (2'-Formyl-6-methoxy-4'-nitro-biphenyl-3-yl)-acetic acid ethyl ester
Prepared according to the procedure described in Example 1, Step 4, using the following starting materials: 2-bromo-5-nitro-benzaldehyde and [4-methoxy-3-(4,4,5,5-tetramethyl-[1,3,2]dioxaborolan-2-yl)-phenyl]-acetic acid ethyl ester.
Step 4: (2'-Ethylaminomethyl-6-methoxy-4'-nitro-biphenyl-3-yl)-acetic acid ethyl ester
Prepared according to the procedure described in Example 11, Step 4, using the following starting materials: (2'-formyl-6-methoxy-4'-nitro-biphenyl-3-yl)-acetic acid ethyl ester and ethylamine (2M in THF).
Step 5: {2'-[(Benzyloxycarbonyl-ethyl-amino)-methyl]-6-methoxy-4'-nitro-biphenyl-3-yl}-acetic acid ethyl ester
Prepared according to the procedure described in Example 1, Step 6, using the following starting materials: (2'-ethylaminomethyl-6-methoxy-4'-nitro-biphenyl-3-yl)-acetic acid ethyl ester and benzyl chloroformate.
Step 6: {4'-Amino-2'-[(benzyloxycarbonyl-ethyl-amino)-methyl]-6-methoxy-biphenyl-3-yl}-acetic acid ethyl ester
To a solution of {2'-[(benzyloxycarbonyl-ethyl-amino)-methyl]-6-methoxy-4'-nitro-biphenyl-3-yl}-acetic acid ethyl ester (0.70 g, 1.75 mmol) in EtOH (70 mL) was added tin (II) chloride (1.97 g, 8.75 mmol). The reaction was heated to reflux for 5 h, and then the mixture was acidified to pH 1 with concentrated HCl and diluted with EtOAc. The resulting biphasic mixture was filtered through Celite, and the organic layer was separated. The aqueous layer was neutralized to pH 7 with solid NaOH and extracted with EtOAc. The combined organic extracts were dried and filtered, and the residue was purified by silica gel chromatography to give the title compound.
Step 8:
{4'-Amino-2'-[(benzyloxycarbonyl-ethyl-amino)-methyl]-6-methoxy-biphenyl-3-yl}-acetic acid ethyl ester (0.080 g, 0.2 mmol), methanesulfonyl chloride (0.04 mL, 0.3 mmol), and triethylamine were reacted in CH$_2$Cl$_2$ to give {2'-[(benzyloxycarbonyl-ethyl-amino)-methyl]-4'-methanesulfonylamino-6-methoxy-biphenyl-3-yl}-acetic acid ethyl ester. {2'-[(Benzyloxycarbonyl-ethyl-amino)-methyl]-4'-methanesulfonylamino-6-methoxy-biphenyl-3-yl}-acetic acid ethyl ester (0.2 mmol) was hydrolyzed with lithium hydroxide to give the title compound.
{4'-Acetylamino-2'-[(benzyloxycarbonyl-ethyl-amino)-methyl]-6-methoxy-biphenyl-3-yl}-acetic acid (Compound 1-153) was prepared according to the previous procedure using acetyl chloride instead of methanesulfonyl chloride.

Example 14

Synthesis of {4'-Bromo-2'-[(tert-butoxycarbonyl-ethyl-amino)-methyl]-6-methoxy-biphenyl-3-yl}-acetic acid ethyl ester Step 1: 5-Bromo-2-iodo-benzaldehyde
To 5-bromo-2-iodobenzonitrile (7.4 g, 24.2 mmol) in THF (40 mL) at −78° C. was added diisobutylaluminium hydride (1M in hexanes; 24.2 mL, 24.2 mmol) over 5 minutes, and the reaction was allowed to warm to room temperature and monitored by analytical tlc. After stirring overnight at room temperature, starting material was still present, so the mixture was cooled to 0° C. and additional diisobutylaluminium hydride (1M in hexanes; 10.0 mL, 10.0 mmol) was added. After stirring for 2 hours at room temperature, no starting material was seen by analytical tlc, so the mixture was carefully quenched with freshly saturated aqueous $Na_2SO_4$ and diluted with EtOAc. The mixture was stirred vigorously for 1 hour and then filtered through Celite. The filtrate was concentrated, and the resulting oil solidified on standing. The solid was stirred vigorously in $CH_2Cl_2$ and 1N aqueous HCl, and the aqueous layer was separated and extracted with $CH_2Cl_2$. The combined organic layers were dried over $MgSO_4$, filtered, and concentrated to give the title compound.

Step 2: (5-Bromo-2-iodo-benzyl)-ethyl-amine

To 5-bromo-2-iodo-benzaldehyde (5.0 g, 16.1 mmol) in MeOH (20 mL) was added ethylamine (2M in MeOH; 16 mL, 24.0 mmol), followed by acetic acid (1.0 mL, 17.8 mmol), and the mixture was stirred at room temperature for 30 minutes. Sodium cyanoborohydride (2.0 g, 31.8 mmol) was then added over 5 minutes, and the reaction was stirred at room temperature over the weekend. The mixture was concentrated and partitioned between EtOAc and saturated aqueous $NaHCO_3$. The aqueous layer was extracted with EtOAc, and the combined organic layers were dried over $MgSO_4$, filtered, and concentrated. The residue was purified by silica gel chromatography (0-5% MeOH in $CH_2Cl_2$) to give the title compound.

Step 3: (5-Bromo-2-iodo-benzyl)-ethyl-carbamic acid tert-butyl ester (5-Bromo-2-iodo-benzyl)-ethyl-amine (4.05 g, 11.9 mmol) in $CH_2Cl_2$ (30 mL) was treated with di-tert-butyl dicarbonate (3.12 g, 14.3 mmol) at room temperature overnight. The mixture was diluted with $CH_2Cl_2$ and washed with $H_2O$, dried over $MgSO_4$, filtered, and concentrated to give the title compound.

Step 4: {4'-Bromo-2'-[(tert-butoxycarbonyl-ethyl-amino)-methyl]-6-methoxy-biphenyl-3-yl}-acetic acid ethyl ester Prepared according to the procedure described in Example 1, Step 4, using the following starting materials: (5-bromo-2-iodo-benzyl)-ethyl-carbamic acid tert-butyl ester and [4-methoxy-3-(4,4,5,5-tetramethyl-[1,3,2]dioxaborolan-2-yl)-phenyl]-acetic acid ethyl ester.

Example 15

Synthesis of (2'-{[Ethyl-(2,2,2-trifluoro-acetyl)-amino]-methyl}-6-methoxy-4'-trifluoromethyl-biphenyl-3-yl)-acetic acid (Compound 1-32)

A solution of (2'-ethylaminomethyl-6-methoxy-4'-trifluoromethyl-biphenyl-3-yl)-acetic acid methyl ester (0.106 g, 0.28 mmol) and triethylamine (0.06 mL, 0.42 mmol) in $CH_2Cl_2$ (1 mL) was cooled to -78° C. Trifluoroacetic anhydride (0.06 mL, 0.42 mmol) was added, and the reaction was stirred at room temperature for 1 hour. Additional triethylamine and trifluoroacetic anhydride were added. After 2 hours, the mixture was diluted with $CH_2Cl_2$ and $H_2O$, and the aqueous layer was extracted with $CH_2Cl_2$. The combined organic layers were dried over $Na_2SO_4$, filtered, and concentrated, and the residue was purified by silica gel chromatography (0-100% EtOAc in hexanes) to give (2'-{[ethyl-(2,2,2-trifluoro-acetyl)-amino]-methyl}-6-methoxy-4'-trifluoromethyl-biphenyl-3-yl)-acetic acid methyl ester. The methyl ester was hydrolyzed according to the procedure described in Example 3, Step 3.

Example 16

Synthesis of 2-{[Acetyl-(2,2,2-trifluoro-ethyl)-amino]-methyl}-5'-carboxymethyl-2'-methoxy-biphenyl-4-carboxylic acid (Compound 1-37)

Step 1: 2-{[Acetyl-(2,2,2-Trifluoro-Ethyl)-Amino]-Methyl}-5'-Carboxymethyl-2'-Methoxy-Biphenyl-4-Carboxylic Acid (2'-{[Acetyl-(2,2,2-trifluoro-ethyl)-amino]-methyl}-6-methoxy-4'-trifluoromethyl-biphenyl-3-yl)-acetic acid (0.709 g, 1.46 mmol) was dissolved in 1N aqueous NaOH (4 mL, 4 mmol) with heating, and stirred at 100° C. for 1 hour. Ethylene glycol (10 mL) was added, and the reaction was stirred at 150° C. for 3 hours. Sodium hydroxide pellets (0.727 g, 18.2 mmol) was added, and the reaction was stirred at 150° C. overnight. After cooling to room temperature, the mixture was neutralized with 1N aqueous HCl and extracted twice with $CH_2Cl_2$. The combined organic layers were dried over $MgSO_4$, filtered, and concentrated, and the residue was purified by preparative HPLC. The isolated material was repurified by preparative HPLC to give the title compound.

Example 17

Synthesis of (2'-{[(3,5-Dichloro-benzyloxycarbonyl)-ethyl-amino]-methyl}-6-methoxy-4'-trifluoromethyl-biphenyl-3-yl)-acetic acid (Compound 1-38)

Step 1: 3,5-Dichlorobenzyl Chloroformate

To 3,5-dichlorobenzyl alcohol (0.201 g, 1.06 mmol) in $CH_2Cl_2$ (0.5 mL) was added phosgene (20% in toluene; 0.42 mL, 0.79 mmol), and the mixture was stirred at room temperature for 30 minutes to give the title compound, which was used directly in the next step.

Step 2: (2'-{[(3,5-Dichloro-benzyloxycarbonyl)-ethyl-amino]-methyl}-6-methoxy-4'-trifluoromethyl-biphenyl-3-yl)-acetic acid methyl ester To (2'-ethylaminomethyl-6-methoxy-4'-trifluoromethyl-biphenyl-3-yl)-acetic acid methyl ester (0.101 g, 0.26 mmol) and diisopropylethylamine (0.23 mL, 1.32 mmol) in $CH_2Cl_2$ (1 mL) was added 3,5-dichlorobenzyl chloroformate (1.06 mmol) in $CH_2Cl_2$, and the reaction was stirred at room temperature for 5 minutes. The mixture was diluted with $H_2O$ and extracted with $CH_2Cl_2$. The combined organic layers were dried over $Na_2SO_4$, decanted, and concentrated, and the residue was purified by silica gel chromatography to give the title compound.

Step 3: (2'-{[(3,5-Dichloro-benzyloxycarbonyl)-ethyl-amino]-methyl}-6-methoxy-4'-trifluoromethyl-biphenyl-3-yl)-acetic acid (2'-{[(3,5-Dichloro-benzyloxycarbonyl)-ethyl-amino]-methyl}-6-methoxy-4'-trifluoromethyl-biphenyl-3-yl)-acetic acid methyl ester (0.088 g, 0.15 mmol) in THF (1 mL) and MeOH (0.8 mL) was hydrolyzed with 1N aqueous NaOH (0.5 mL) for 2.5 hours. The mixture was acidified with 1N aqueous HCl and extracted with $CH_2Cl_2$. The combined organic layers were dried over $Na_2SO_4$, decanted, and concentrated, and the residue was purified by preparative HPLC to give the title compound.

Example 18

Synthesis of (2'-{[(2-Chloro-benzyloxycarbonyl)-ethyl-amino]-methyl}-6-methoxy-4'-trifluoromethyl-biphenyl-3-yl)-acetic acid (Compound 1-39)

Step 1: (2'-{[(2-Chloro-benzyloxycarbonyl)-ethyl-amino]-methyl}-6-methoxy-4'-trifluoromethyl-biphenyl-3-yl)-acetic acid methyl ester To (2'-ethylaminomethyl-6-methoxy-4'-trifluoromethyl-biphenyl-3-yl)-acetic acid methyl ester (0.103 g, 0.27 mmol) and triethylamine (0.06 mL, 0.40 mmol) in $CH_2Cl_2$ (1 mL) was added 2-chlorobenzyl chloroformate (0.06 mL, 0.40 mmol), and the reaction was stirred at room temperature for 1 hour. The mixture was diluted with $CH_2Cl_2$ and $H_2O$, and the aqueous layer was extracted with $CH_2Cl_2$. The combined organic layers were dried over $Na_2SO_4$, decanted, and concentrated, and the residue was purified by silica gel chromatography (0-100% EtOAc in hexanes) to give the title compound.

Step 2: (2'-{[(2-Chloro-benzyloxycarbonyl)-ethyl-amino]-methyl}-6-methoxy-4'-trifluoromethyl-biphenyl-3-yl)-acetic acid (2'-{[(2-Chloro-benzyloxycarbonyl)-ethyl-amino]-methyl}-6-methoxy-4'-trifluoromethyl-biphenyl-3-yl)-acetic acid methyl ester (0.27 mmol) in THF (1 mL) and MeOH (0.8 mL) was hydrolyzed with 1N aqueous NaOH (0.7 mL) for 1 hour. The mixture was acidified with 1N aqueous HCl and extracted with $CH_2Cl_2$. The combined organic layers were dried over $MgSO_4$, filtered, and concentrated to give the title compound.

(2'-{[(3,5-Difluoro-benzyloxycarbonyl)-ethyl-amino]-methyl}-6-methoxy-4'-trifluoromethyl-biphenyl-3-yl)-acetic acid (Compound 1-40) was prepared by following the procedures outlined in Example 18 and using 3,5-difluorobenzyl alcohol.

(2'-{[Ethyl-(4-fluoro-benzyloxycarbonyl)-amino]-methyl}-6-methoxy-4'-trifluoromethyl-biphenyl-3-yl)-acetic acid (Compound 1-41) was prepared by following the procedures outlined in Example 18 and using 4-fluorobenzyl alcohol.

(2'-{[(4-Chloro-benzyloxycarbonyl)-ethyl-amino]-methyl}-6-methoxy-4'-trifluoromethyl-biphenyl-3-yl)-acetic acid (Compound 1-42) was prepared by following the procedures outlined in Example 18 and using 4-chlorobenzyl alcohol.

(2'-{[(3-Chloro-benzyloxycarbonyl)-ethyl-amino]-methyl}-6-methoxy-4'-trifluoromethyl-biphenyl-3-yl)-acetic acid (Compound 1-43) was prepared by following the procedures outlined in Example 18 and using 3-chlorobenzyl alcohol.

[2'-({[1-(4-Chloro-phenyl)-ethoxycarbonyl]-ethyl-amino}-methyl)-6-methoxy-4'-trifluoromethyl-biphenyl-3-yl]-acetic acid (Compound 1-44) was prepared by following the procedures outlined in Example 18 and using 1-(4-chlorophenyl)ethanol.

Example 19

Synthesis of (2'-{[Benzyloxycarbonyl-(2,2,2-trifluoro-ethyl)-amino]-methyl}-6-fluoro-4'-trifluoromethyl-biphenyl-3-yl)-acetic acid (Compound 1-49)

{6-Fluoro-2'-[(2,2,2-trifluoro-ethylamino)-methyl]-4'-trifluoromethyl-biphenyl-3-yl}-acetic acid methyl ester (0.26 g, 0.62 mmol), benzyl chloroformate (0.13 mL, 0.93 mmol), and triethylamine (0.13 mL, 0.93 mmol) were combined in $CH_2Cl_2$ (2.1 mL), and the reaction was stirred at room temperature for 2 hours. Additional benzyl chloroformate (0.13 mL, 0.93 mmol), and triethylamine (0.13 mL, 0.93 mmol) were added, and the reaction was stirred for 1 hour. Starting material was still present, so an aqueous work-up was performed, and the residue was dissolved in DMF and cooled to 0° C. Sodium hydride (60% in mineral oil; 0.030 g, 0.75 mmol) was added, followed by benzyl chloroformate (0.13 mL, 0.93 mmol), and the reaction was stirred for 20 minutes. The mixture was worked up with $CH_2Cl_2$ and $H_2O$, and the organic layer was dried over $MgSO_4$, filtered, and concentrated. The residue was purified by silica gel chromatography to give (2'-{[benzyloxycarbonyl-(2,2,2-trifluoro-ethyl)-amino]-methyl}-6-fluoro-4'-trifluoromethyl-biphenyl-3-yl)-acetic acid methyl ester. The ester was hydrolyzed according to the procedure described in Example 17, Step 3.

Example 20

Synthesis of {2'-[(Benzyloxycarbonyl-ethyl-amino)-methyl]-4'-trifluoromethyl-biphenyl-3-yl}-acetic acid (Compound 1-143)

Step 1: (3-Bromo-phenyl)-acetic acid methyl ester

To 3-bromophenylacetic acid (5.03 g, 23.4 mmol) in MeOH (50 mL) was added thionyl chloride (3.4 mL, 46.8 mmol), and the reaction was stirred at 65° C. for 5 hours. The mixture was concentrated, and the residue was partitioned between $CH_2Cl_2$ and saturated aqueous $NaHCO_3$. The mixture was basified with 1N aqueous NaOH, and the aqueous layer was extracted with $CH_2Cl_2$. The combined organic layers were washed with $H_2O$, dried over $MgSO_4$, filtered, and concentrated to give the title compound.

Step 2: [3-(4,4,5,5-Tetramethyl-[1,3,2]dioxaborolan-2-yl)-phenyl]-acetic acid methyl ester Prepared according to the procedure described in Example 1, Step 2, using the following starting materials: (3-bromophenyl)-acetic acid methyl ester and bis(pinacolato)diboron.

Step 3: (2'-Formyl-4'-trifluoromethyl-biphenyl-3-yl)-acetic acid methyl ester

Prepared according to the procedure described in Example 1, Step 4, using the following starting materials: [3-(4,4,5,5-tetramethyl-[1,3,2]dioxaborolan-2-yl)-phenyl]-acetic acid methyl ester and 2-bromo-5-(trifluoromethy)benzaldehyde.

Step 4: (2'-Ethylaminomethyl-4'-trifluoromethyl-biphenyl-3-yl)-acetic acid methyl ester Prepared according to the procedure described in Example 1, Step 5, using the following starting materials: (2'-formyl-4'-trifluoromethyl-biphenyl-3-yl)-acetic acid methyl ester and ethylamine (2M in THF).

Step 5: {2'-[(Benzyloxycarbonyl-ethyl-amino)-methyl]-4'-trifluoromethyl-biphenyl-3-yl}-acetic acid methyl ester Prepared according to the procedure described in Example 1, Step 6, using the following starting materials: (2'-ethylaminomethyl-4'-trifluoromethyl-biphenyl-3-yl)-acetic acid methyl ester and benzyl chloroformate.

Step 6: {2'-[(Benzyloxycarbonyl-ethyl-amino)-methyl]-4'-trifluoromethyl-biphenyl-3-yl}-acetic acid Prepared according to the procedure described in Example 3, Step 3, using the following starting material: {2'-[(benzyloxycarbonyl-ethyl-amino)-methyl]-4'-trifluoromethyl-biphenyl-3-yl}-acetic acid methyl ester.

Example 21

Synthesis of {2'-[1-Ethyl-3-(4-hydroxy-benzyl)-ureidomethyl]-6-methoxy-4'-trifluoromethyl-biphenyl-3-yl}-acetic acid (Compound 1-252)

Step 1: {2'-[1-Ethyl-3-(4-hydroxy-benzyl)-ureidomethyl]-6-methoxy-4'-trifluoromethyl-biphenyl-3-yl}-acetic acid ethyl ester To (2'-ethylaminomethyl-6-methoxy-4'-trifluoromethyl-biphenyl-3-yl)-acetic acid ethyl ester (0.59 g, 1.49 mmol) and diisopropylethylamine (0.65 mL, 3.73 mmol) in $CH_2Cl_2$ (6 mL) at 0° C. was added phosgene (20% in toluene; 1.2 mL, 2.24 mmol), and the reaction was stirred for 1 hour. 4-Hydroxybenzylamine (0.278 g, 2.24 mmol) and triethylamine (1 mL, 7.47 mmol) were then added, and the reaction was stirred for 2 hours. Additional 4-hydroxybenzylamine (0.184 g, 1.49 mmol) was added, and the reaction was stirred for another 30 minutes. The mixture was partitioned between $CH_2Cl_2$ and $H_2O$, and the organic layer was dried over $MgSO_4$, filtered, and concentrated. The residue was purified by silica gel chromatography (0-100% EtOAc in hexanes) to give the title compound.

Step 2: {2'-[1-Ethyl-3-(4-hydroxy-benzyl)-ureidomethyl]-6-methoxy-4'-trifluoromethyl-biphenyl-3-yl}-acetic acid {2'-[1-Ethyl-3-(4-hydroxy-benzyl)-ureidomethyl]-6-methoxy-4'-trifluoromethyl-biphenyl-3-yl}-acetic acid ethyl ester (0.535 g, 0.98 mmol) in THF (5 mL) and EtOH (4 mL) was treated with 1N aqueous NaOH (3 mL), and the reaction was stirred for 2.5 hours. Analytical LCMS indicated that starting material was still present, so additional 1N aqueous NaOH was added, and the reaction was heated with a heat gun. Once no starting material was seen by analytical LCMS, the mixture was worked-up with $CH_2Cl_2$ and 1N aqueous HCl, and the organic layer was dried over $MgSO_4$, filtered, and concentrated to give the title compound.

{2'-[1-Ethyl-3 -(2-hydroxy-benzyl)-ureidomethyl]-6-methoxy-4'-trifluoromethyl-biphenyl-3 -yl}-acetic acid (Compound 1-253) was prepared by following the procedures outlined in Example 21 and using (2'-ethylaminomethyl-6-methoxy-4'-trifluoromethyl-biphenyl-3-yl)-acetic acid ethyl ester and 2-hydroxybenzylamine.

{2'-[1-Ethyl-3 -(3 -hydroxy-benzyl)-ureidomethyl]-6-methoxy-4'-trifluoromethyl-biphenyl-3-yl}-acetic acid (Compound 1-257) was prepared by following the procedures outlined in Example 21 and using (2'-ethylaminomethyl-6-methoxy-4'-trifluoromethyl-biphenyl-3-yl)-acetic acid ethyl ester and 3-(aminomethyl)phenol.

Example 22

Synthesis of [2'-({[2-(4-Chloro-phenoxy)-2-methyl-propionyl]-ethyl-amino}-methyl)-6-methoxy-4'-trifluoromethyl-biphenyl-3-yl]-acetic acid (Compound 1-118)

Step 1: 2-(4-Chloro-phenoxy)-2-methyl-propionic acid

A solution of 2-(4-chlorophenoxy)isobutyric acid ethyl ester (1.0 g, 4.12 mmol) in THF (10 mL) was treated with 1N aqueous LiOH (10 mL) and stirred overnight at room temperature. The mixture was acidified with 1N aqueous HCl to pH 3-4 and extracted three times with EtOAc. The combined organic layers were dried and concentrated to give the title compound.

Step 2: 2-(4-Chloro-phenoxy)-2-methyl-propionyl chloride 2-(4-Chloro-phenoxy)-2-methyl-propionic acid (0.124 g, 0.58 mmol) and triethylamine (0.09 mL, 0.62 mmol) were combined in CH2Cl2 (2 mL) and cooled to 0° C. Oxalyl chloride (0.05 mL, 0.62 mmol) was added, followed by DMF (3 drops), and the mixture was slowly warmed to room temperature and stirred for 2 hours to give the title compound, which was used directly in the next step.

Step 3: [2'-({[2-(4-Chloro-phenoxy)-2-methyl-propionyl]-ethyl-amino}-Methyl)-6-Methoxy-4'-trifluoromethyl-biphenyl-3-yl]-acetic acid To a solution of 2-(4-chloro-phenoxy)-2-methyl-propionyl chloride (0.58 mmol) in $CH_2Cl_2$ was added (2'-ethylaminomethyl-6-methoxy-4'-trifluoromethyl-biphenyl-3-yl)-acetic acid methyl ester (0.200 g, 0.52 mmol) in triethylamine (0.17 mL, 1.23 mmol), and the reaction was stirred at room temperature for 30 minutes. The mixture was concentrated and purified by silica gel chromatography (10-30% EtOAc in hexanes) to give [2'-({[2-(4-chloro-phenoxy)-2-methyl-propionyl]-ethyl-amino}-methyl)-6-methoxy-4'-trifluoromethyl-biphenyl-3-yl]-acetic acid methyl ester. The ester was hydrolyzed according to the procedure described in Example 9, Step 2.

Example 23

Synthesis of {2'-[3-(4-Chloro-benzyl)-1-ethyl-ureidomethyl]-6-methoxy-4'-trifluoromethyl-biphenyl-3-yl}-acetic acid (Compound 1-140)

Step 1: {2'-[3-(4-Chloro-benzyl)-1-ethyl-ureidomethyl]-6-methoxy-4'-trifluoromethyl-biphenyl-3-yl}-acetic acid ethyl ester To (2'-ethylaminomethyl-6-methoxy-4'-trifluoromethyl-biphenyl-3-yl)-acetic acid ethyl ester (0.196 g, 0.50 mmol) in $CH_2Cl_2$ (2 mL) at 0° C. was added diisopropylethylamine (0.21 mL, 1.24 mmol), followed by phosgene (20% in toluene, 0.39 mL, 0.75 mmol), and the mixture was stirred for 3 hours. 4-Chlorobenzylamine (0.09 mL, 0.75 mmol) was added, followed by triethylamine (0.14 mL, 1.0 mmol), and the reaction was stirred at room temperature for 20 minutes. Additional triethylamine (0.07 mL, 0.5 mmol) was added, and the reaction was stirred for 1 hour and then worked-up with $CH_2Cl_2$ and $H_2O$. The organic layer was dried and concentrated, and the residue was purified by silica gel chromatography (0-50% EtOAc in hexanes) to give the title compound.

Step 2: {2'-[3-(4-Chloro-benzyl)-1-ethyl-ureidomethyl]-6-methoxy-4'-trifluoromethyl-biphenyl-3-yl}-acetic acid To {2'-[3-(4-chloro-benzyl)-1-ethyl-ureidomethyl]-6-methoxy-4'-trifluoromethyl-biphenyl-3-yl}-acetic acid ethyl ester (0.196 g, 0.35 mmol) in THF (2 mL) and MeOH (2 mL) was added 1N aqueous LiOH (2 mL), and the reaction was stirred at room temperature for 2 hours. The mixture was acidified with 1N aqueous HCl and extracted three times with EtOAc, and the combined organic layers were dried and concentrated. The residue was purified by preparative HPLC to give the title compound.

Example 24

Synthesis of {2'-[3-(3,4-Dichloro-benzyl)-1-ethyl-ureidomethyl]-6-methoxy-4'-trifluoromethyl-biphenyl-3-yl}-acetic acid (Compound 1-152)

(2'-Ethylaminomethyl-6-methoxy-4'-trifluoromethyl-biphenyl-3-yl)-acetic acid ethyl ester (0.170 g, 0.42 mmol) and triethylamine (0.12 mL, 0.86 mmol) were combined in $CH_2Cl_2$ (2 mL). 3,4-Dichlorobenzyl isocyanate (0.08 mL, 0.52 mmol) was added, and the reaction was stirred at room temperature for 15 minutes. After concentrating, the crude material was purified by silica gel chromatography (20-50% EtOAc in hexanes) to give {2'-[3-(3,4-dichloro-benzyl)-1-ethyl-ureidomethyl]-6-methoxy-4'-trifluoromethyl-biphenyl-3-yl}-acetic acid ethyl ester. The ethyl ester was hydrolyzed according to the procedure described in Example 23, Step 2.

[2'-(3-Benzyl-1-ethyl-ureidomethyl)-4'-fluoro-6-methoxy-biphenyl-3-yl]-acetic acid (Compound 1-187) was prepared by following the procedures of Example 24 and using (2'-ethylaminomethyl-4'-fluoro-6-methoxy-biphenyl-3-yl)-acetic acid ethyl ester and benzyl isocyanate.

Example 25

Synthesis of {2'-[3-(3,5-Dichloro-benzyl)-1-ethyl-ureidomethyl]-6-methoxy-4'-trifluoromethyl-biphenyl-3-yl}-acetic acid (Compound 1-165)

Step 1: {2'-[3-(3,5-Dichloro-benzyl)-1-ethyl-ureidomethyl]-6-methoxy-4'-trifluoromethyl-biphenyl-3-yl}-acetic acid ethyl ester To a solution of (2'-ethylaminomethyl-6-methoxy-4'-trifluoromethyl-biphenyl-3-yl)-acetic acid ethyl ester (0.170 g, 0.43 mmol) in $CH_2Cl_2$ (2 mL) at 0° C. was added diisopropylethylamine (0.19 mL, 1.08 mmol), followed by phosgene (20% in toluene; 0.34 mL, 0.64 mmol), and the mixture was stirred for 1.5 hours. 3,5-Dichlorobenzylamine (0.091 g, 0.52 mmol) was added, followed by triethylamine (0.12 mL, 0.86 mmol), and the reaction was warmed to room temperature and stirred for 45 minutes. Additional triethylamine (0.12 mL, 0.86 mmol) was added, and the reaction was stirred for 1.5 hours. Another portion of triethylamine (0.25 mL, 17.9 mmol) was added, and the reaction was stirred overnight at room temperature. The mixture was worked up with $CH_2Cl_2$ and $H_2O$, and the aqueous layer was extracted twice with $CH_2Cl_2$. The combined organic layers were dried and concentrated, and the residue was purified by silica gel chromatography (0-50% EtOAc in hexanes) to give the title compound.

Step 2: {2'-[3-(3,5-Dichloro-benzyl)-1-ethyl-ureidomethyl]-6-methoxy-4'-trifluoromethyl-biphenyl-3-yl}-acetic acid Prepared according to the procedure described in Example 23, Step 2, using the following starting material: {2'-[3-(3,5-dichloro-benzyl)-1-ethyl-ureidomethyl]-6-methoxy-4'-trifluoromethyl-biphenyl-3-yl}-acetic acid ethyl ester.

The following compounds were also prepared by the procedures of Example 25:

{2'-[1-Ethyl-3-(4-fluoro-benzyl)-ureidomethyl]-6-methoxy-4'-trifluoromethyl-biphenyl-3-yl}-acetic acid (Compound 1-176) was prepared by using 4-fluorobenzylamine.

{2'-[3-(3-Chloro-benzyl)-1-ethyl-ureidomethyl]-6-methoxy-4'-trifluoromethyl-biphenyl-3-yl}-acetic acid (Compound 1-177) was prepared by using 3-chlorobenzylamine.

{2'-[3-(3,5-Difluoro-benzyl)-1-ethyl-ureidomethyl]-6-methoxy-4'-trifluoromethyl-biphenyl-3-yl}-acetic acid (Compound 1-178) was prepared by using 3,5-difluorobenzylamine.

(2'-{3-[(R)-1-(4-Chloro-phenyl)-ethyl]-1-ethyl-ureidomethyl}-6-methoxy-4'-trifluoromethyl-biphenyl-3-yl)-acetic acid (Compound 1-179) was prepared by using (R)-(+)-1-(4-chlorophenyl)ethylamine.

(2'-{3-[(S)-1-(4-Chloro-phenyl)-ethyl]-1-ethyl-ureidomethyl}-6-methoxy-4'-trifluoromethyl-biphenyl-3-yl)-acetic acid (Compound 1-180) was prepared by using (S)-4-chloro-alpha-methylbenzylamine.

[2'-(1,3-Diethyl-ureidomethyl)-6-methoxy-4'-trifluoromethyl-biphenyl-3-yl]-acetic acid (Compound 1-181) was prepared by using ethylamine (2M in THF).

Example 26

Synthesis of {2'-[(Cyclopropanecarbonyl-ethyl-amino)-methyl]-4'-trifluoromethyl-biphenyl-3-yl}-acetic acid (Compound 1-244)

Step 1: (2'-Ethylaminomethyl-4'-trifluoromethyl-biphenyl-3-yl)-acetic acid

{2'-[(Benzyloxycarbonyl-ethyl-amino)-methyl]-4'-trifluoromethyl-biphenyl-3-yl}-acetic acid (0.16 g, 0.34 mmol) in EtOH (7 mL) was treated with 10% palladium on carbon (0.072 g), and the reaction was stirred under a balloon of $H_2$ for 3 hours to give the title compound.

Step 2: (2'-Ethylaminomethyl-4'-trifluoromethyl-biphenyl-3-yl)-acetic acid ethyl ester To a solution of (2'-ethylaminomethyl-4'-trifluoromethyl-biphenyl-3-yl)-acetic acid (0.34 mmol) in EtOH (7 mL) was added sulfuric acid (3-4 drops), and the reaction was stirred at 50° C. overnight. Once no starting material was seen by analytical LCMS, the mixture was filtered over a pad of Celite and rinsed with EtOH. The filtrate was concentrated to give the title compound.

Step 3: {2'-[(Cyclopropanecarbonyl-ethyl-amino)-methyl]-4'-trifluoromethyl-biphenyl-3-yl}-acetic acid ethyl ester Prepared according to the procedure described in Example 1, Step 6, using the following starting materials: (2'-ethylaminomethyl-4'-trifluoromethyl-biphenyl-3-yl)-acetic acid ethyl ester and cyclopropanecarbonyl chloride.

Step 4: {2'-[(Cyclopropanecarbonyl-ethyl-amino)-methyl]-4'-trifluoromethyl-biphenyl-3-yl}-acetic acid The ethyl ester from Step 3 was hydrolyzed according to the procedure described in Example 23, Step 2.

Example 27

Synthesis of [2'-(3-Benzyl-1-ethyl-ureidomethyl)-6-hydroxy-4'-trifluoromethyl-biphenyl-3-yl]-acetic acid ethyl ester Step 1: [4-Benzyloxy-3-(4,4,5,5-tetramethyl-[1,3,2]dioxaborolan-2-yl)-phenyl]-acetic acid ethyl ester Prepared according to the procedure described in Example 1, Step 2, using the following starting materials: (4-benzyloxy-3-bromo-phenyl)-acetic acid ethyl ester and bis(pinacolato)diboron.

Step 2: (6-Benzyloxy-2'-formyl-4'-trifluoromethyl-biphenyl-3-yl)-acetic acid ethyl ester Prepared according to the procedure described in Example 1, Step 4, using the following starting materials: [4-benzyloxy-3-(4,4,5,5-tetramethyl-[1,3,2]dioxaborolan-2-yl)-phenyl]-acetic acid ethyl ester and 2-bromo-5-(trifluoromethyl)benzaldehyde.

Step 3: (6-Benzyloxy-2'-ethylaminomethyl-4'-trifluoromethyl-biphenyl-3-yl)-acetic acid ethyl ester Prepared according to the procedure described in Example 1, Step 5, using the following starting materials: (6-benzyloxy-2'-formyl-4'-trifluoromethyl-biphenyl-3-yl)-acetic acid ethyl ester and ethylamine (2M in THF).

Step 4: [2'-(3-Benzyl-1-ethyl-ureidomethyl)-6-benzyloxy-4'-trifluoromethyl-biphenyl-3-yl]acetic acid ethyl ester Prepared according to the procedure described in Example 24, Step 1, using the following starting materials: (6-benzyloxy-2'-ethylaminomethyl-4'-trifluoromethyl-biphenyl-3-yl)-acetic acid ethyl ester and benzyl isocyanate.

Step 5: [2'-(3-Benzyl-1-ethyl-ureidomethyl)-6-hydroxy-4'-trifluoromethyl-biphenyl-3-yl]-acetic acid ethyl ester

[2'-(3-Benzyl-1-ethyl-ureidomethyl)-6-benzyloxy-4'-trifluoromethyl-biphenyl-3-yl]-acetic acid ethyl ester (0.580 g, 0.96 mmol) in EtOAc was treated with 10% palladium on carbon (catalytic) and stirred under a balloon of $H_2$ overnight. Analytical tlc indicated that some starting material was still present, so fresh palladium on carbon was added, and the reaction was stirred under a balloon of $H_2$ for an additional 24 hours. Once no starting material was seen by analytical tlc, the mixture was filtered over Celite, and the filtrate was concentrated and purified by silica gel chromatography to give the title compound.

Example 28

[2'-(3-Benzyl-1-ethyl-ureidomethyl)-6-hydroxy-4'-trifluoromethyl-biphenyl-3-yl]-acetic acid (Compound 1-220)

Hydrolysis of the ethyl ester of [2'-(3-benzyl-1-ethyl-ureidomethyl)-6-hydroxy-4'-trifluoromethyl-biphenyl-3-yl]-acetic acid ethyl ester provides the title compound.

Example 29

Synthesis of 2-[(Benzyloxycarbonyl-ethyl-amino)-methyl]-5'-carboxymethyl-2'-methoxy-biphenyl-4-carboxylic acid (Compound 1-226)

Step 1: 4-Bromo-3-methyl-benzoic acid ethyl ester

To 4-bromo-3-methylbenzoic acid (16.27 g, 75.7 mmol) in EtOH (500 mL) was added concentrated sulfuric acid (0.5 mL), and the reaction was stirred at 95° C. overnight. Additional sulfuric acid (2 mL) was added and then the mixture was quenched with the slow addition of sodium carbonate. The mixture was filtered and concentrated, and the residue was diluted and washed with $H_2O$ twice, saturated aqueous $NaHCO_3$, brine, and $H_2O$ to give the title compound.

Step 2: 4-Bromo-3-bromomethyl-benzoic acid ethyl ester

4-Bromo-3-methyl-benzoic acid ethyl ester (18.24 g, 75.4 mmol), N-bromosuccinimide (14.1 g, 79.2 mmol), and benzoyl peroxide (0.9 g, 3.77 mmol) were combined in $CCl_4$, and the reaction was heated to 80° C. and stirred with a halogen desk lamp shining on it for 6 hours. The mixture was concentrated and partitioned between $CH_2Cl_2$ and $H_2O$. The organic layer was separated and washed with $H_2O$ and brine, and then dried and concentrated. The residue was triturated with hexane (3×50 mL) and dried to give the title compound.

Step 3: Ethyl-carbamic acid benzyl ester

Ethylamine (1.3 mL, 20.0 mmol) and diisopropylethylamine (7 mL, 40.0 mmol) were combined in $CH_2Cl_2$ (200 mL) and cooled to 0° C. Benzyl chloroformate (2.86 mL, 20.0 mmol) was added dropwise, and the reaction was stirred at 0° C. for 30 minutes. Once no starting material was seen by analytical tlc, the mixture was warmed to room temperature and washed with $H_2O$, 0.1N aqueous HCl, and $H_2O$, and then dried and concentrated to give the title compound.

Step 4: 3-[(Benzyloxycarbonyl-ethyl-amino)-methyl]-4-bromo-benzoic acid ethyl ester 4-Bromo-3-bromomethyl-benzoic acid ethyl ester (2.95 g, 9.2 mmol) and ethyl-carbamic acid benzyl ester (3.30 g, 18.4 mmol) were combined in DMF (100 mL) and cooled to 0° C. Sodium hydride (60% in mineral oil; 0.772 g, 19.3 mmol) was added slowly, and the reaction was stirred at room temperature for 10 minutes. The mixture was quenched with $H_2O$ and 1N aqueous HCl (20 mL), and then extracted with 1:1 EtOAc: hexanes three times. The organic layer was washed with brine, and then dried and concentrated. The residue was purified by silica gel chromatography (0-100% EtOAc in hexanes) to give the title compound, as well as the hydrolyzed product, which was combined with the product from the next step.

Step 5: 3-[(Benzyloxycarbonyl-ethyl-amino)-methyl]-4-bromo-benzoic acid

3-[(Benzyloxycarbonyl-ethyl-amino)-methyl]-4-bromo-benzoic acid ethyl ester (3.62 g, 7.2 mmol) was dissolved in MeOH (40 mL) and cooled to 0° C. 1N Aqueous LiOH (22 mL, 22 mmol) was added, and the reaction was stirred at room temperature for 3 hours. The mixture was quenched with 1N aqueous HCl (22 mL) and extracted three times with EtOAc. The combined organic layers were washed with brine, dried, and concentrated to give the title compound, which was combined with the hydrolyzed product isolated in step 5.

Step 6:

Prepared according to the procedure described in Example 1, Step 4, using the following starting materials: 3-[(benzyloxycarbonyl-ethyl-amino)-methyl]-4-bromo-benzoic acid and [4-methoxy-3-(4,4,5,5-tetramethyl-[1,3,2]dioxaborolan-2-yl)-phenyl]-acetic acid ethyl ester. The ethyl ester was then hydrolyzed with 1N aqueous LiOH in THF at room temperature to give the title compound.

Example 30

Synthesis of [2'-(3-Benzyl-1,3-diethyl-ureidomethyl)-6-methoxy-4'-trifluoromethyl-biphenyl-3-yl]-acetic acid (Compound 1-94)

Step 1: N-Ethyl-N-benzylcarbamoyl Chloride

N-Ethylbenzylamine (0.56 mL, 3.8 mmol) and diisopropylethylamine (1 mL, 5.7 mmol) were combined in $CH_2Cl_2$ (12 mL) and cooled to 0° C. Phosgene (20% in toluene; 2.4 mL, 4.6 mmol) was added, and the reaction was stirred overnight at room temperature. The mixture was concentrated, and the residue was dissolved in $Et_2O$ and washed twice with $H_2O$. The organic layer was dried, filtered, and concentrated to give the title compound.

Step 2: (2'-Ethylaminomethyl-6-methoxy-4'-trifluoromethyl-biphenyl-3-yl)-acetic acid methyl ester (0.130 g, 0.34 mmol), N-ethyl-N-benzylcarbamoyl chloride (0.081 g, 0.41 mmol), 4-dimethylaminopyridine (0.010 g, 0.08 mmol), and triethylamine (0.12 mL, 0.85 mmol) were combined in $CH_2Cl_2$ (5 mL) and stirred at reflux overnight. The mixture was purified by silica gel chromatography (0-100% EtOAc in hexanes) to give [2'-(3-Benzyl-1,3-diethyl-ureidomethyl)-6-methoxy-4'-trifluoromethyl-biphenyl-3-yl]-acetic acid methyl ester. The ethyl ester was then hydrolyzed with 1N aqueous LiOH in THF at room temperature to give the title compound.

Example 31

Synthesis of {2'-[(Benzyloxycarbonyl-ethyl-amino)-methyl]-4'-fluoro-6-methoxy-biphenyl-3-yl}-acetic acid (Compound 1-183)

Step 1: (4'-Fluoro-2'-formyl-6-methoxy-biphenyl-3-yl)-acetic acid ethyl ester

Prepared according to the procedure described in Example 1, Step 4, using the following starting materials: 2-bromo-5-fluorobenzaldehyde and [4-methoxy-3-(4,4,5,5-tetramethyl-[1,3,2]dioxaborolan-2-yl)-phenyl]-acetic acid ethyl ester.

Step 2: (2'-Ethylaminomethyl-4'-fluoro-6-methoxy-biphenyl-3-yl)-acetic acid ethyl ester Prepared according to the procedure described in Example 1, Step 5, using the following starting materials: (4'-Fluoro-2'-formyl-6-methoxy-biphenyl-3-yl)-acetic acid ethyl ester and ethylamine (2M in THF).

Step 3: {2'-[(Benzyloxycarbonyl-ethyl-amino)-methyl]-4'-fluoro-6-methoxy-biphenyl-3-yl}-acetic acid (2'-Ethylaminomethyl-4'-fluoro-6-methoxy-biphenyl-3-yl)-acetic acid ethyl ester (0.172 g, 0.5 mmol) and diisopropylethylamine (0.18 mL, 1.0 mmol) were combined in CH$_2$Cl$_2$ (2.5 mL) and cooled to 0° C. Benzyl chloroformate (0.1 mL, 0.7 mmol) was added, and the reaction was stirred for 1 hour. The mixture was purified by silica gel chromatography, and then further purified by preparative HPLC to give {2'-[(benzyloxycarbonyl-ethyl-amino)-methyl]-4'-fluoro-6-methoxy-biphenyl-3-yl}-acetic acid ethyl ester. The ethyl ester was hydrolyzed to give the title compound.

{2'-[(Acetyl-ethyl-amino)-methyl]-4'-fluoro-6-methoxy-biphenyl-3-yl}-acetic acid (Compound 1-184) was prepared by reacting (2'-ethylaminomethyl-4'-fluoro-6-methoxy-biphenyl-3-yl)-acetic acid ethyl ester and acetyl chloride according to the procedure described in Example 1, Step 6 and then hydrolyzing the ester with aqueous LiOH in THF at room temperature.

{2'-[(Cyclopropanecarbonyl-ethyl-amino)-methyl]-4'-fluoro-6-methoxy-biphenyl-3-yl}-acetic acid (Compound 1-186) was prepared by reacting(2'-ethylaminomethyl-4'-fluoro-6-methoxy-biphenyl-3-yl)-acetic acid ethyl ester and cyclopropanecarbonyl chloride according to the procedure described in Example 1, Step 6 and then hydrolyzing the ester with aqueous LiOH in THF at room temperature Example 32

Synthesis of {2'-[3-(4-Chloro-benzyl)-1-ethyl-ureidomethyl]-4'-fluoro-6-methoxy-biphenyl-3-yl}-acetic acid (Compound 1-185)

(2'-Ethylaminomethyl-4'-fluoro-6-methoxy-biphenyl-3-yl)-acetic acid ethyl ester (0.172 g, 0.5 mmol) and diisopropylethylamine (0.43 mL, 2.5 mmol) were combined in CH$_2$Cl$_2$ (2.5 mL) and cooled to 0° C. Phosgene (20% in toluene; 0.40 mL, 0.75 mmol) was added, and the mixture was stirred for 1 hour. 4-Chlorobenzylamine (0.012 mL, 1.0 mmol) was added, and the reaction was stirred for 1 hour. The mixture was diluted with CH$_2$Cl$_2$ and washed with H$_2$O. The organic layer was dried, filtered, and concentrated, and the residue was purified by preparative HPLC to give {2'-[3-(4-chloro-benzyl)-1-ethyl-ureidomethyl]-4'-fluoro-6-methoxy-biphenyl-3-yl}-acetic acid ethyl ester. The ethyl ester was hydrolyzed with LiOH in THF at room temperature to provide the title compound.

Example 33

Synthesis of {2'-[(Benzyloxycarbonyl-ethyl-amino)-methyl]-4'-methanesulfonyl-6-methoxy-biphenyl-3-yl}-acetic acid (Compound 1-215)

Step 1: 2-Hydroxy-5-methanesulfonyl-benzaldehyde
5-Bromosalicylaldehyde (0.402 g, 2.0 mmol), sodium methanesulfinate (0.918 g, 9.0 mmol), and copper(I) iodide (1.71 g, 9.0 mmol) were combined in NMP (16 mL) and stirred under N$_2$ at 140° C. overnight. The mixture was diluted with 1:1 EtOAc:hexanes (150 mL) and filtered through a pad of Celite. The filtrate was washed three times with H$_2$O, and then dried, filtered, and concentrated. The residue was purified by silica gel chromatography (0-100% EtOAc in hexanes) to give the title compound.

Step 2: 2-Ethylaminomethyl-4-methanesulfonyl-phenol
2-Hydroxy-5-methanesulfonyl-benzaldehyde (0.200 g, 1.0 mmol), ethylamine (2M in THF; 0.75 mL, 1.5 mmol), and sodium cyanoborohydride (0.095 g, 1.5 mmol) were combined in MeOH (10 mL). 4Å Molecular sieves were added, followed by acetic acid (0.09 mL, 1.5 mmol), and the reaction was stirred for 1 hour. The mixture was filtered, and H$_2$O (0.5 mL) was added and the solution was concentrated. The residue was partitioned between EtOAc (100 mL) and brine (20 mL), and the mixture was neutralized with 1N aqueous HCl (1 mL) and extracted six times with EtOAc, until minimal product was seen in the aqueous layer by analytical tlc. The combined organic layers were dried, filtered, and concentrated to give the title compound.

Step 3: Ethyl-(2-Hydroxy-5-methanesulfonyl-benzyl)-carbamic acid benzyl ester
To 2-ethylaminomethyl-4-methanesulfonyl-phenol (0.229 g, 1.0 mmol) and diisopropylamine (0.94 mL, 2.5 mmol) in CH$_2$Cl$_2$ (10 mL) was added benzyl chloroformate (0.16 mL, 1.1 mmol). Some over-acylation product was observed, so additional benzyl chloroformate (0.21 mL) was added to convert all of the product to the diacylated product. After aqueous work-up, the organic layer was concentrated, and the residue was dissolved in MeOH (10 mL) and treated with 1N aqueous LiOH (4 mL). Once the hydrolysis was complete, the mixture was worked-up, and the residue was purified to give the title compound.

Step 4: Trifluoro-methanesulfonic acid 2-[(benzyloxycarbonyl-ethyl-amino)-methyl]-4-methanesulfonyl-phenyl ester
Ethyl-(2-hydroxy-5-methanesulfonyl-benzyl)-carbamic acid benzyl ester (0.200 g, 0.55 mmol) and diisopropylethylamine (0.24 mL, 1.38 mmol) were combined in CH$_2$Cl$_2$ (10 mL). Trifluoromethanesulfonic anhydride (0.11 mL, 0.65 mmol) was added, and the reaction was stirred for 5 minutes at room temperature. The mixture was quenched with H$_2$O and diluted with CH$_2$Cl$_2$. The organic layer was dried, filtered, and concentrated, and the residue was purified by silica gel chromatography (0-50% EtOAc in hexanes) to give the title compound.

Step 5: {2'-[(Benzyloxycarbonyl-ethyl-amino)-methyl]-4'-methanesulfonyl-6-methoxy-biphenyl-3-yl}-acetic acid ethyl ester
Trifluoro-methanesulfonic acid 2-[(benzyloxycarbonyl-ethyl-amino)-methyl]-4-methanesulfonyl-phenyl ester (1.3 g, 2.62 mmol), [4-methoxy-3-(4,4,5,5-tetramethyl-[1,3,2]dioxaborolan-2-yl)-phenyl]-acetic acid ethyl ester (1.26 g, 3.93 mmol), and cesium carbonate (2.55 g, 7.85 mmol) were combined in DMF. (1,1'-Bis(diphenylphosphino)ferrocene)-dichloropalladium(II) (0.213 g, 0.26 mmol) was added, and the reaction was immediately immersed in an oil bath preheated to 45° C. The reaction was stirred at 65° C. for 20 minutes, and then worked-up and purified to give the title compound, contaminated with a phenol by-product. The mixture was dissolved in CH$_2$Cl$_2$ (100 mL) and washed with 0.5N aqueous NaOH, and then concentrated to give the title compound.

Step 6: {2'-[(Benzyloxycarbonyl-ethyl-amino)-methyl]-4'-methanesulfonyl-6-methoxy-biphenyl-3-yl}-acetic acid
The ethyl ester was hydrolyzed according to the procedure described in Example 9, Step 2.

Example 34

Synthesis of [2'-[(Benzyloxycarbonyl-ethyl-amino)-methyl]-4'-(1-hydroxy-1-methyl-ethyl)-6-methoxy-Biphenyl-3-yl]acetic acid (Compound 1-216)

Step 1: 4-Bromo-3-methyl-benzoic acid ethyl ester
To 4-bromo-3-methylbenzoic acid (3 g, 14 mmol) in EtOH (200 mL) was added thionyl chloride (2 mL, 28 mmol), and the reaction was stirred for 10 minutes. Additional thionyl chloride (3 mL, 35 mmol) was added, and the reaction was stirred overnight at 50° C. After cooling to room temperature, the mixture was quenched with the slow addition of powdered Na$_2$CO$_3$, and then filtered and concentrated. The residue was partitioned between EtOAc and H$_2$O, and the organic layer was dried, filtered, and concentrated to give the title compound.

Step 2: 2-(4-Bromo-3-methyl-phenyl)-propan-2-ol

To 4-bromo-3-methyl-benzoic acid ethyl ester (0.968 g, 4.0 mmol) in THF (50 mL) at 0° C. was added methylmagnesium bromide (3M in Et$_2$O; 4 mL, 12 mmol), and the reaction was stirred at 1 hour at 0° C. and then warmed to room temperature. Additional methylmagnesium bromide (3M in Et$_2$O; 4 mL, 12 mmol) was added, and the reaction was stirred for 30 minutes. The mixture was quenched with saturated aqueous NH$_4$Cl and partitioned between EtOAc and H$_2$O. The organic layer was dried, filtered, and concentrated to give the title compound.

Step 3: 2-(4-Bromo-3-bromomethyl-phenyl)-propan-2-ol 2-(4-Bromo-3-methyl-phenyl)-propan-2-ol (0.916 g, 4.0 mmol) in CCl$_4$ (30 mL) was treated with N-bromosuccinimide (0.750 g, 4.2 mmol) and benzoyl peroxide (0.050 g, 0.2 mmol), and the reaction was refluxed under a halogen lamp for 2 hours. After cooling to room temperature, the mixture was partitioned between CH$_2$Cl$_2$ and H$_2$O, and the organic layer was dried, filtered, and concentrated. The residue was purified by silica gel chromatography to give the title compound.

Step 4: [2-Bromo-5-(1-hydroxy-1-methyl-ethyl)-benzyl]-ethyl-carbamic acid benzyl ester To 2-(4-bromo-3-bromomethyl-phenyl)-propan-2-ol (0.255 g, 0.83 mmol) and ethyl-carbamic acid benzyl ester (0.446 g, 2.49 mmol) in DMF (15 mL) was added sodium hydride (60% in mineral oil; 0.103 g, 2.57 mmol), and the reaction was stirred for 30 minutes. The mixture was quenched with H$_2$O and worked-up. The residue was purified by silica gel chromatography (0-40% EtOAc in hexanes) to give the title compound.

Step 5: [2'-[(Benzyloxycarbonyl-ethyl-amino)-methyl]-4'-(1-hydroxy-1-methyl-ethyl)-6-methoxy-biphenyl-3-yl]-acetic acid ethyl ester Prepared according to the procedure described in Example 1, Step 4, using the following starting materials: [2-bromo-5-(1-hydroxy-1-methyl-ethyl)-benzyl]-ethyl-carbamic acid benzyl ester and [4-methoxy-3-(4,4,5,5-tetramethyl-[1,3,2]dioxaborolan-2-yl)-phenyl]-acetic acid ethyl ester.

Step 6: [2'-[(Benzyloxycarbonyl-ethyl-amino)-methyl]-4'-(1-hydroxy-1-methyl-ethyl)-6-methoxy-biphenyl-3-yl]-acetic acid The ethyl ester was hydrolyzed according to the procedure described in Example 9, Step 2.

Example 35

Synthesis of {2'-[(Cyclopropanecarbonyl-ethyl-amino)-methyl]-6-methoxy-4'-methylsulfanyl-biphenyl-3-yl}-acetic acid (Compound 1-241)

Step 1: {2'-[(Cyclopropanecarbonyl-ethyl-amino)-methyl]-4'-fluoro-6-methoxy-biphenyl-3-yl}-acetic acid ethyl ester Prepared according to the procedure described in Example 1, Step 6, using the following starting materials: (2'-ethylaminomethyl-4'-fluoro-6-methoxy-biphenyl-3-yl)-acetic acid ethyl ester and cyclopropanecarbonyl chloride.

Step 2: {2'-[(Cyclopropanecarbonyl-ethyl-amino)-methyl]-6-methoxy-4'-methylsulfanyl-biphenyl-3-yl}-acetic acid To {2'-[(cyclopropanecarbonyl-ethyl-amino)-methyl]-4'-fluoro-6-methoxy-biphenyl-3-yl}-acetic acid ethyl ester 0.186 g, 0.45 mmol) in DMF (0.5 mL) was added sodium thiomethoxide (0.035 g, 0.50 mmol), and the reaction was stirred at 85° C. for 2 hours. Additional sodium thiomethoxide (0.070 g, 1.0 mmol) was added, and the reaction was stirred at 85° C. for another 2 hours. An aqueous work-up was performed, and the residue was purified by preparative HPLC to give the title compound.

Mass spectrometric data for select compounds are displayed in Table 1.

Example 36

CRTH2 Assays

Example 36a

DP$_2$/CRTH2 Binding Assay

The ability of a compound to bind to the human DP$_2$ receptor is assessed via a radioligand binding assay using [$^3$H]PGD$_2$. HEK293 cells stably expressing recombinant human DP$_2$ are resuspended in 10 mM Hepes, 7.4 containing 1 mM DTT, lysed and centrifuged at 75,000×g to pellet the membranes. The membranes are resuspended in 10 mM Hepes, 7.4 containing 1 mM DTT and 10% glycerol to approximately 5 mg protein/ml. Membranes (2-10 μg protein/well) are incubated in 96-well plates with 1 nM [$^3$H] PGD$_2$ and test compound in Assay Buffer (50 mM Hepes, 10 mM MnCl$_2$, 1 mM EDTA, plus or minus 0.2% human serum albumin, pH 7.4) for 60 minutes at room temperature. The reactions are terminated by rapid filtration through Whatman GF/C glass fibre filter plates. The filter plates were pre-soaked in 0.33% polyethylenimine for 30 minutes at room temperature then washed in Wash Buffer (50 mM Hepes, 0.5 M NaCl pH 7.4) prior to harvesting. After harvesting, the filter plates are washed 3 times with 1 ml cold Wash Buffer then dried. Scintillant is then added to the plates and the radioactivity retained on the filters is determined on a Packard TopCount (Perkin Elmer). Specific binding is determined as total radioactive binding minus non-specific binding in the presence of 10 μM PGD$_2$. IC$_{50}$s were determined using GraphPad prism analysis of drug titration curves. Compounds tested had an IC$_{50}$ of less than 20 micromolar in this assay.

Example 36b

GTPγS Binding Assay

The ability of a compound to inhibit binding of GTP to DP$_2$ is assessed via a membrane GTPγS assay. CHO cells stably expressing the recombinant human CRTH2 receptor are resuspended in 10 mM Hepes, 7.4 containing 1 mM DTT, lysed and centrifuged at 75,000×g to pellet the membranes. The membranes are resuspended in 10 mM Hepes, 7.4 containing 1 mM DTT and 10% glycerol. Membranes (~12.5 μg per well) are incubated in 96-well plates with 0.05 nM [$^{35}$S]-GTPγS, 80 nM PGD$_2$, 5 μM GDP, and test compound in Assay Buffer (50 mM Hepes, pH 7.4, 100 mM NaCl, 5 mM MgCl$_2$ and 0.2% human serum albumin) for 60 minutes at 30° C. The reactions are terminated by rapid filtration through Whatman GF/B glass fibre filter plates. The filter plates are washed 3 times with 1 ml cold Assay Buffer and dried. Scintillant is then added to the plates and the radioactivity retained on the filters is determined on a Packard TopCount (Perkin Elmer). Specific binding is determined as total radioactive binding minus non-specific binding in the absence of the ligand (80 nM PGD$_2$). IC$_{50}$s were determined using Graphpad prism analysis of drug titration curves.

Example 36c

Whole Blood Esoinophil Shape Change Assay

Blood is drawn from consenting human volunteers in EDTA vacutainer tubes and used within 1 hr of draw. A 98 μl aliquot of blood is mixed with 2 μl of test compound (in 50% DMSO) in 1.2 ml polypropylene tubes. The blood is vortexed and incubated at 37° C. for 15 minutes. 5 μM of 1 μM PGD$_2$ in PBS is added for a final concentration of 50 nM and the tubes briefly vortexed. The reactions are incubated for exactly 5 minutes at 37° C. and then terminated by placing the tubes on ice and immediately adding 250 μl of ice-cold 1:4 diluted Cytofix (BD Biosciences). The reactions are transferred to 12×75 mM polystyrene round bottom tubes and the red blood cells lysed by the addition of 3 ml ammonium chloride lysing solution (150 mM NH$_4$Cl, 10 mM KHCO$_3$, 0.1 mM EDTA disodium salt) and incubation at room temperature for 15 minutes. The cells are pelleted by spinning at 1300 rpm for 5 minutes at 4° C. and washed once with 3 ml ice-cold PBS. The cells are resuspended in 0.2 ml of ice-cold 1:4 diluted Cytofix (BD Biosciences) and analyzed on a FACSCalibur (BD Biosciences) within 2 hours. Eosinophils were gated on the basis of autofluorescence in the FL2 channel and shape change on 500 eosinophils was assayed by forward scatter and side scatter analysis. The specific change in shape induced by PGD$_2$ was calculated as the difference between the percentage of high forward scatter eosinophils in the presence and absence of PGD$_2$. IC$_{50}$s were determined using Graphpad Prism® analysis of drug titration curves.

Example 36d

DP$_1$ Binding Assay

The ability of a compound to bind to the human DP1 receptor was evaluated via a radioligand membrane binding assay using the DP$_1$ selective synthetic ligand [$^3$H] BWA868C. Packed human platelets (Biological Specialty Corporation), were resuspended in 6 volumes of Hepes/HBSS buffer (10 mM Hepes, 1 mM DTT in Hanks Balanced Salt Solution (HBSS)), lysed and centrifuged at 75,000×g to pellet the membranes. Membranes were resuspended in Hepes/HBSS buffer to approximately 12 mg protein/ml. Membranes (20 μg protein/well) are incubated in 96-well plates with 2 nM [$^3$H]BWA868C and test compound in Assay Buffer (50 mM Hepes, 10 mM MnCl$_2$, 1 mM EDTA, plus or minus 0.2% human serum albumin, pH 7.4) for 60 minutes at room temperature. The reactions are terminated by rapid filtration through Whatman GF/C glass fibre filter plates. The filter plates were pre-soaked in 0.33% polethylenimine for 30 minutes at room temperature then washed in Wash Buffer (50 mM Hepes, 0.5 M NaCl pH 7.4) prior to harvesting. After harvesting, the filter plates are washed 3 times with 1 ml cold Wash Buffer then dried. Scintillant is then added to the plates and the radioactivity retained on the filters is determined on a Packard TopCount (Perkin Elmer). Specific binding is determined as total radioactive binding minus non-specific binding in the presence of 10 μM BW A868C. IC$_{50}$s were determined using GraphPad prism analysis of drug titration curves.

Example 37

Mouse Allergic Rhinitis Model

The compounds ability to inhibit allergen-induced sneezing and nasal rubbing is assessed using a mouse model of allergic rhinitis. Methods were adapted from those detailed in Nakaya, M., et al.. 2006, *Laboratory Investigation*, 86:917-926. Female BALB/c mice (20-25 g) are immunized by an intraperitoneal injection (i.p.) of 2 μg ovalbumin (OVA) complexed with alum in a volume 0.2 ml on days 0 and 14. Seven days later (day 21) mice are challenged intranasally with 20 μl of a 10 mg/ml solution of OVA. The challenge period occurs daily from days 21 to day 25. Mice (5-7/group) are randomly assigned to receive either compound or vehicle and are treated by oral gavage 1-2 hour prior to each OVA challenge. The number of sneezes and nasal rubs are counted by an independent blind observe during a period of 8 minutes immediately following OVA challenge on days 21, 23 and 25. A significant increase in allergen-induced sneezing and nasal rubbing occurs over the 5-day challenge period. Inhibition of this effect by select compounds is determined statistically using Graphpad prism.

Example 38

Guinea Pig IV-DKPGD2-Induced Peripheral Blood Leukocyte Influx

The compounds ability to inhibit leukocyte migration in vivo was assessed using intravenous injection of 13,14-dihydro-15-keto-prostaglandin D2 (DK-PGD2). Methods were adapted from those detailed Shichijo et al., 2003, *Journal of Pharmacology and Experimental Therapeutics*, 307:518-525. Male Hartley guinea pigs were immunized with ovalbumin (OVA) on day 0 by intraperitoneal (IP) injection of 1 ml of a 100 μg/ml solution in Imject Alum. They were then used in the DK-PGD2 procedure between days 14 and 21. Subjects were randomly assigned to receive either vehicle (0.5% methyl cellulose, 4 ml/kg, oral (PO)) or one of three to four doses of test compound. Two hours or eighteen hours after dosing, animals were anesthetized with ketamine and challenged with DK-PGD2 (1 mg/kg, IV). Thirty minutes after IV administration, blood was collected via the marginal ear vein into EDTA tubes for cell analysis. 10 μl blood was lysed in 190 μl water followed by a further 20-fold dilution in PBS. A 10 μl fraction was mixed with equal parts trypan blue and loaded on a hemocytometer. Cells were visualized at a magnification of 40× using a LabPro light microscope and totals counted and recorded. Cells are expressed as total cells×10$^8$ per ml of blood. Inhibition of this effect by select compounds is determined statistically using Graphpad prism.

The compounds that were tested in Table 1 had IC$_{50}$ below 20 μM in the CRTH2 binding assay.

TABLE 4

Representative Biological Data

| Compound # | hDP2 μM | hDP1 μM | hDP2 GTPγS μM (+HSA) |
|---|---|---|---|
| 1-1 | A | C | A |
| 1-2 | A | C | A |
| 1-4 | A | C | A |
| 1-10 | A | C | A |
| 1-11 | A | C | A |
| 1-12 | A | C | A |
| 1-23 | A | C | A |
| 1-27 | A | C | A |
| 1-28 | A | C | A |
| 1-29 | A | C | A |
| 1-30 | A | C | A |
| 1-31 | A | C | A |
| 1-32 | A | C | A |
| 1-33 | A | C | A |
| 1-34 | A | C | A |
| 1-35 | A | B | A |
| 1-36 | A | C | A |
| 1-37 | C | C | — |
| 1-38 | A | C | A |
| 1-39 | A | C | A |
| 1-40 | A | C | A |
| 1-41 | A | C | A |

TABLE 4-continued

Representative Biological Data

| Compound # | hDP2 µM | hDP1 µM | hDP2 GTPγS µM (+HSA) |
|---|---|---|---|
| 1-42 | A | C | A |
| 1-43 | A | C | A |
| 1-44 | A | C | A |
| 1-45 | A | C | A |
| 1-46 | A | C | A |
| 1-48 | A | C | A |
| 1-49 | C | C | — |
| 1-92 | A | C | A |
| 1-93 | A | C | A |
| 1-94 | A | C | A |
| 1-96 | A | C | A |
| 1-110 | A | C | A |
| 1-118 | A | C | A |
| 1-129 | A | C | A |
| 1-143 | A | B | — |
| 1-152 | A | C | — |
| 1-153 | A | C | — |
| 1-155 | A | C | — |
| 1-165 | A | C | — |
| 1-176 | A | C | — |
| 1-177 | A | C | — |
| 1-178 | A | C | — |
| 1-179 | A | C | — |
| 1-180 | A | C | — |
| 1-181 | A | C | — |
| 1-183 | A | C | — |
| 1-184 | A | C | — |
| 1-185 | A | C | — |
| 1-186 | A | C | A |
| 1-187 | A | C | — |
| 1-206 | A | — | — |
| 1-215 | A | — | — |
| 1-216 | A | — | — |
| 1-220 | A | — | A |
| 1-226 | A | — | — |
| 1-241 | A | — | — |
| 1-244 | A | — | — |
| 1-245 | C | — | — |
| 1-246 | A | — | A |
| 1-247 | A | — | — |
| 1-252 | A | — | — |
| 1-253 | A | — | — |
| 1-257 | A | — | — |
| Ramatroban | B | C | B |

A = less than 0.3 µM;
B = greater than 0.3 µm and less than 1 µM;
C = greater than 1 µM.

Example 39

Clinical Trials in Humans

Study 1: Clinical Trial Evaluating Effect of Compound of Formula (I) on Ex Vivo PGD2-Induced Blood Eosinophil Shape Change In this double-blind, randomized, placebo-controlled, single ascending dose study of Compound of Formula (I) in healthy volunteers the inhibition of ex vivo PGD2-induced blood eosinophil shape change is determined to show proof of biochemical mechanism of DP2 receptor antagonism. Eight subjects (6 active, 2 placebo) per dose level are used. Pre dose blood is drawn and challenged with PGD2 to determine baseline shape change as described above in Example 36. At varying times after dosing blood is drawn for both pharmacokinetic analyses of drug concentration in blood, and also for PGD2 challenge and eosinophil shape change determination. The extent of receptor blockage is determined from the relationship between drug blood concentration and percentage inhibition of eosinophil shape change.

Study 2: Clinical Trial Evaluating Effect of Compound of Formula (I) on Allergen-Induced Nasal Symptoms and Inflammatory and Allergic Biomarkers In this double-blind, randomized, placebo-controlled study of Compound of Formula (I) in individuals with allergic rhinitis the inhibition of nasal symptoms and allergic biomarkers is determined following nasal challenge with appropriate allergen. Fifteen subjects (10 active, 5 placebo) are used. Subjects are dosed for 7 days with either placebo or an amount of compound of formula (I) that results in complete DP2 receptor block in an ex vivo PGD2-induced blood eosinophil shape change pharmacodynamic study as described above. On day 7 subjects undergo nasal allergen challenge (2 hours post-dose) and early allergic response (0.25-1.0 hr) and late allergic response (4-24 hr) are evaluated as an increase from baseline for treated vs placebo. In addition changes in inflammatory cell differentials, TH2 cytokines and other inflammatory markers are determined as increase from baseline for treated vs placebo.

Compound of Formula (I) Assay

The plasma concentrations of compound of Formula (I) are determined by gas chromatography, giving a detection limit of 1 ng·ml-1 (Ritter W. Determination of BAY u 3405, a novel thromboxane antagonist, in plasma and urine by HPLC and GC. In: Reid E, Wilson ID, eds. Bioanalytical Approaches for Drugs, Including Anti-asthmatics and Metabolites. Methodological Surveys in Biochemistry and Analysis, 1992; 22: 211-216).

Example 40a

Parenteral Composition

To prepare a parenteral pharmaceutical composition suitable for administration by injection, 100 mg of a water-soluble salt of a compound of Formula (I) is dissolved in DMSO and then mixed with 10 mL of 0.9% sterile saline. The mixture is incorporated into a dosage unit form suitable for administration by injection.

Example 40b

Oral Composition

To prepare a pharmaceutical composition for oral delivery, 100 mg of a compound of Formula (I) is mixed with 750 mg of starch. The mixture is incorporated into an oral dosage unit for, such as a hard gelatin capsule, which is suitable for oral administration.

Example 40c

Sublingual (Hard Lozenge) Composition

To prepare a pharmaceutical composition for buccal delivery, such as a hard lozenge, mix 100 mg of a compound of Formula (I) with 420 mg of powdered sugar mixed, with 1.6 mL of light corn syrup, 2.4 mL distilled water, and 0.42 mL mint extract. The mixture is gently blended and poured into a mold to form a lozenge suitable for buccal administration.

Example 40d

Fast-Disintegrating Sublingual Tablet

A fast-disintegrating sublingual tablet is prepared by mixing 48.5% by weigh of a compound of Formula (I), 44.5% by weight of microcrystalline cellulose (KG-802), 5% by weight of low-substituted hydroxypropyl cellulose (50 µm), and 2% by weight of magnesium stearate. Tablets are prepared by direct compression (*AAPS PharmSciTech*. 2006;7(2):E41). The total weight of the compressed tablets is maintained at 150 mg. The formulation is prepared by mixing the amount of compound of Formula (I) with the total quantity of microcrystalline cellulose (MCC) and two-thirds of the quantity of low-substituted hydroxypropyl celluose (L-HPC) by using a three dimensional manual mixer (Inversina®, Bioengineering AG, Switzerland) for 4.5 minutes. All of the magnesium stearate (MS) and the remaining one-third of the quantity of L-HPC are added 30 seconds before the end of mixing.

Example 40e

Inhalation Composition

To prepare a pharmaceutical composition for inhalation delivery, 20 mg of a compound of Formula (I) is mixed with 50 mg of anhydrous citric acid and 100 mL of 0.9% sodium chloride solution. The mixture is incorporated into an inhalation delivery unit, such as a nebulizer, which is suitable for inhalation administration.

Example 40f

Rectal Gel Composition

To prepare a pharmaceutical composition for rectal delivery, 100 mg of a compound of Formula (I) is mixed with 2.5 g of methylceluose (1500 mPa), 100 mg of methylparapen, 5 g of glycerin and 100 mL of purified water. The resulting gel mixture is then incorporated into rectal delivery units, such as syringes, which are suitable for rectal administration.

Example 40g

Topical Gel Composition

To prepare a pharmaceutical topical gel composition, 100 mg of a compound of Formula (I) is mixed with 1.75 g of hydroxypropyl celluose, 10 mL of propylene glycol, 10 mL of isopropyl myristate and 100 mL of purified alcohol USP. The resulting gel mixture is then incorporated into containers, such as tubes, which are suitable for topicl administration.

Example 40h

Ophthalmic Solution Composition

To prepare a pharmaceutical opthalmic solution composition, 100 mg of a compound of Formula (I) is mixed with 0.9 g of NaCl in 100 mL of purified water and filterd using a 0.2 micron filter. The resulting isotonic solution is then incorporated into ophthalmic delivery units, such as eye drop containers, which are suitable for ophthalmic administration.

Example 40i

Nasal Spray Solution

To prepare a pharmaceutical nasal spray solution, 10 g of a compound of Formula (I) is mixed with 30 mL of a 0.05M phosphate buffer solution (pH 4.4). The solution is placed in a nasal administrator designed to deliver 100 µl of spray for each application.

The examples and embodiments described herein are for illustrative purposes only and various modifications or changes suggested to persons skilled in the art are to be included within the spirit and purview of this application and scope of the appended claims.

What is claimed is:

1. A method for treating atopic dermatitis in a mammal comprising administering to the mammal a therapeutically effective amount of a compound having the following structure:

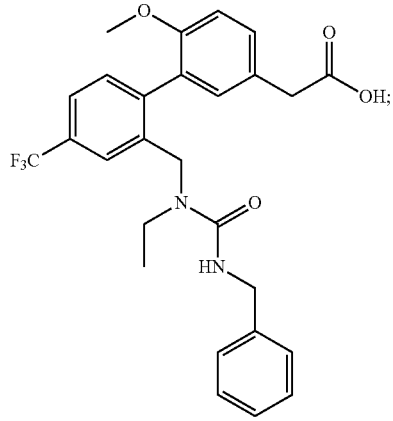

or a pharmaceutically acceptable salt thereof.

2. The method of claim 1, wherein the pharmaceutically acceptable salt is a sodium salt.

3. The method of claim 1, wherein the mammal is a human and the therapeutically effective amount of the compound, or a pharmaceutically acceptable salt thereof, is orally administered to the human.

4. The method of claim 1, wherein the mammal is a human and the therapeutically effective amount of the compound, or a pharmaceutically acceptable salt thereof, is orally administered to the human in the form of a tablet, a pill, a capsule, or a liquid.

5. The method of claim 1, wherein the mammal is a human and the therapeutically effective amount of the compound, or a pharmaceutically acceptable salt thereof, is topically administered to the human.

6. The method of claim 1, wherein the mammal is a human and the therapeutically effective amount of the compound, or a pharmaceutically acceptable salt thereof, is topically administered to the human in the form of a solution, suspension, lotion, gel, paste, medicated stick, balm, cream or ointment.

7. A method for treating eosinophilic esophagitis in a mammal comprising administering to the mammal a therapeutically effective amount of a compound having the following structure:

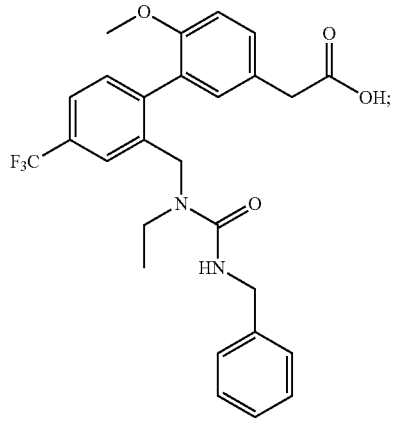

or a pharmaceutically acceptable salt thereof.

8. The method of claim 7, wherein the pharmaceutically acceptable salt is a sodium salt.

9. The method of claim 7, wherein the mammal is a human and the therapeutically effective amount of the compound, or a pharmaceutically acceptable salt thereof, is orally administered to the human.

10. The method of claim 7, wherein the mammal is a human and the therapeutically effective amount of the compound, or a pharmaceutically acceptable salt thereof, is orally administered to the human in the form of a tablet, a pill, a capsule, or a liquid.

* * * * *